US 8,198,405 B2

Jun. 12, 2012

(12) United States Patent
Walensky et al.

(54) STABILIZED ALPHA HELICAL PEPTIDES AND USES THEREOF

(75) Inventors: Loren D. Walensky, Chestnut Hill, MA (US); Stanley J. Korsmeyer, Weston, MA (US); Susan Korsmeyer, legal representative, Weston, MA (US); Gregory Verdine, Newton, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/182,673

(22) Filed: Jul. 30, 2008

(65) Prior Publication Data

US 2009/0176964 A1    Jul. 9, 2009

Related U.S. Application Data

(63) Continuation of application No. 10/981,873, filed on Nov. 5, 2004, now Pat. No. 7,723,469.

(60) Provisional application No. 60/517,848, filed on Nov. 5, 2003, provisional application No. 60/591,548, filed on Jul. 27, 2004.

(51) Int. Cl.
    *C07K 14/00*    (2006.01)
(52) U.S. Cl. .......... 530/324; 530/323; 530/317; 514/1.1; 514/18.9
(58) Field of Classification Search .......... 514/2; 530/324, 530/317, 323
    See application file for complete search history.

(56) References Cited

U.S. PATENT DOCUMENTS

| | | | |
|---|---|---|---|
| 5,364,851 A | 11/1994 | Joran | |
| 5,446,128 A | 8/1995 | Kahn et al. | |
| 5,622,852 A | 4/1997 | Korsmeyer | |
| 5,663,316 A | 9/1997 | Xudong | |
| 5,672,584 A | 9/1997 | Borchardt et al. | |
| 5,708,136 A | 1/1998 | Burrell et al. | 530/324 |
| 5,811,515 A | 9/1998 | Grubbs et al. | |
| 5,824,483 A | 10/1998 | Houston, Jr. et al. | |
| 5,834,209 A | 11/1998 | Korsmeyer | |
| 5,856,445 A | 1/1999 | Korsmeyer | |
| 5,874,529 A | 2/1999 | Gilon et al. | 530/317 |
| 5,922,863 A | 7/1999 | Grubbs et al. | |
| 5,955,593 A | 9/1999 | Korsmeyer | |
| 5,965,703 A | 10/1999 | Horne et al. | |
| 5,998,583 A | 12/1999 | Korsmeyer | |
| 6,030,997 A | 2/2000 | Eilat et al. | |
| 6,153,391 A | 11/2000 | Picksley et al. | 435/7.1 |
| 6,271,198 B1 | 8/2001 | Braisted et al. | |
| 6,326,354 B1 | 12/2001 | Gross et al. | |
| 6,610,657 B1 | 8/2003 | Goueli | |
| 6,613,874 B1 | 9/2003 | Mazur et al. | |
| 6,703,382 B2 | 3/2004 | Wang et al. | |
| 6,713,280 B1 | 3/2004 | Huang et al. | |
| 7,064,193 B1 * | 6/2006 | Cory et al. | 536/23.1 |
| 7,083,983 B2 | 8/2006 | Lane et al. | 436/501 |
| 7,084,244 B2 | 8/2006 | Gilon et al. | 530/317 |
| 7,192,713 B1 | 3/2007 | Verdine et al. | |
| 7,202,332 B2 | 4/2007 | Arora et al. | 530/333 |
| 7,247,700 B2 | 7/2007 | Korsmeyer | 530/300 |
| 7,538,190 B2 * | 5/2009 | Robinson et al. | 530/333 |
| 7,705,118 B2 | 4/2010 | Arora et al. | |
| 7,723,469 B2 | 5/2010 | Walensky et al. | |
| 7,745,573 B2 * | 6/2010 | Robinson et al. | 530/317 |
| 7,786,072 B2 | 8/2010 | Verdine et al. | |
| 7,981,999 B2 * | 7/2011 | Nash | 530/333 |
| 8,071,541 B2 * | 12/2011 | Arora et al. | 514/2.9 |
| 2004/0115135 A1 | 6/2004 | Quay | |
| 2004/0171809 A1 * | 9/2004 | Korsmeyer et al. | 530/350 |
| 2004/0235746 A1 | 11/2004 | Hawiger et al. | |
| 2005/0250680 A1 | 11/2005 | Walensky et al. | |
| 2006/0008848 A1 | 1/2006 | Verdine et al. | |
| 2006/0014675 A1 | 1/2006 | Arora et al. | |
| 2008/0262200 A1 | 10/2008 | Nash | |
| 2009/0047711 A1 | 2/2009 | Nash | |
| 2009/0088553 A1 | 4/2009 | Nash | |
| 2009/0149630 A1 | 6/2009 | Walensky et al. | |
| 2009/0326192 A1 | 12/2009 | Nash et al. | |
| 2010/0184628 A1 | 7/2010 | Nash | |
| 2010/0184645 A1 | 7/2010 | Verdine et al. | |
| 2010/0216688 A1 * | 8/2010 | Nash et al. | 514/2 |
| 2010/0234563 A1 | 9/2010 | Arora et al. | |
| 2010/0298201 A1 | 11/2010 | Nash et al. | |
| 2011/0028753 A1 | 2/2011 | Verdine et al. | |
| 2011/0144303 A1 | 6/2011 | Nash et al. | |
| 2011/0223149 A1 * | 9/2011 | Nash et al. | 424/94.63 |

(Continued)

FOREIGN PATENT DOCUMENTS

JP    2002-524391    8/2002

(Continued)

OTHER PUBLICATIONS

Bernal et al., J. of Am. Chem. Soc., 129:2456-2457 (2007).
Boguslavsky et al., J. Peptide Res., 61:287-297 (2003).
Kwon et al., Chem. Biol., 14:671-677 (2007).
Viallet et al., Lung Cancer, 15:367-373 (1996).
Non-Final Office Action dated Dec. 5, 2008 from U.S. Appl. No. 10/981,873.
Blackwell, et al. Highly Efficient Synthesis of Covalently Cross-Linked Peptide Helices by Ring-Closing Metathesis. Angewandte Chemie International Edition. 1998; 37(23):3281-3284.
Blackwell, et al. Ring-closing metathesis of olefinic peptides: design, synthesis, and structural characterization of macrocyclic helical peptides. J Org Chem. Aug. 10, 2001;66(16):5291-302.
European search report dated Nov. 7, 2008 for Application No. 8016651.5.
European search report dated Aug. 22, 2008 for Application No. 4811198.3.

(Continued)

*Primary Examiner* — David Lukton
(74) *Attorney, Agent, or Firm* — Wilson Sonsini Goodrich & Rosati

(57) ABSTRACT

Novel polypeptides and methods of making and using the same are described herein. The polypeptides include cross-linking ("hydrocarbon stapling") moieties to provide a tether between two amino acid moieties, which constrains the secondary structure of the polypeptide. The polypeptides described herein can be used to treat diseases characterized by excessive or inadequate cellular death.

19 Claims, 43 Drawing Sheets

U.S. PATENT DOCUMENTS

2011/0263815 A1* 10/2011 Nash .................... 530/317
2012/0082636 A1  4/2012 Walensky et al.

FOREIGN PATENT DOCUMENTS

| | | |
|---|---|---|
| WO | WO 00/06187 A2 | 2/2000 |
| WO | WO 00/06187 A3 | 5/2000 |
| WO | WO 02/064790 A2 | 8/2002 |
| WO | WO 02/064790 A3 | 5/2003 |
| WO | WO 03/106491 A2 | 12/2003 |
| WO | WO2004/058804 | 7/2004 |
| WO | WO2004058804 A1 | 7/2004 |
| WO | WO 03/106491 A3 | 12/2004 |
| WO | WO2005/040202 | 5/2005 |
| WO | WO 2005/040202 | 5/2005 |
| WO | WO 2005/044839 A2 | 5/2005 |
| WO | WO 2005/044839 A3 | 7/2005 |
| WO | WO 2005/090388 | 9/2005 |
| WO | WO 2005/090388 A1 | 9/2005 |
| WO | WO 2005/118634 A2 | 12/2005 |
| WO | WO 2005/118634 A3 | 5/2006 |
| WO | WO 2006/103666 A2 | 10/2006 |
| WO | WO 2006/103666 A3 | 3/2007 |

OTHER PUBLICATIONS

International search report dated May 18, 2005 for PCT Application No. US2004/38403.

European search report and search opinion dated May 6, 2011 for Application No. 10195495.6.

European search report and search opinion dated May 9, 2011 for Application No. 10195490.7.

Wei, et al. tBID, a membrane-targeted death ligand, oligomerizes BAK to release cytochrome c. Genes Dev. Aug. 15, 2000;14(16):2060-71.

Schafmeister CE, Po J, Verdine GL. J Am Chem Soc. 2000; 122:5891-5892.

Titus, *J. Immunol.* 139(9):3153-3158 (1987).

Walensky, L.D., Kung, A.L., Escher, I., Malia, T.J., Barbuto, S., Wright, R., Wagner, G., Verdine, G.L., Korsmeyer, S.J. Science 2004; 305:1466-1470.

Williams, R. M.; Im, M-N., J. Am. Chem. Soc. 1991; 113: 9276-9286.

Andrews et al., "Forming Stable Helical Peptide Using Natural and Artificial Amino Acids" Tetrahedron 55 (1999), pp. 11711-11743.

Baell, J.B., "Prospects for Targeting the Bcl-2 Family of Proteins to Develop . . . "Biochem Pharm 64 (2002), pp. 851-863.

Jackson et al., "General Approach to the Synthesis of Short α-Helical Peptides" J. Am. Chem. Soc. (1991) vol. 113: 9391-9392.

Mai et al., "A Proapoptotic Peptide for the Treatment of Solid Tumors" Cancer Res. 61 (2001), pp. 7709-7712.

McNamara et al, "Peptides Constrained by an Aliphatic Linkage Between two . . . " J. Org. Chem. (2001) vol. 66:4585-4595.

Mustapa, et al., "Synthesis of a Cyclic Peptide Containing Norlanthionine: . . . " J. Org. Chem. (2003), vol. 68:8193-8198.

Schmiedeberg et al., "Reversible Backbone Protection Enables Combinatorial Solid-Phase . . . " Organic Letters (2002), vol. 4(1):59-62.

Tyndall et al., "Macrocycles Mimic the Extended Peptide Conformation Recognized by Aspartic . . . " Currently Medicinal Chem. (2001), vol. 8:893-907.

Wang et al., "Enhances Metabolic Stability and Protein-Binding Properties . . . " Angew Chem Int Ed 44 (2005), pp. 6525-6529.

Wang et al., "Cell Permeable Bcl-2 Binding Peptides: . . . " Cancer Res. (2000), vol. 60:1498-1502.

Yang et al., "Synthesis and Helical Structure of Lactam Bridged BH3 . . . " Bioorg. Med. Chem Lett. (2004), vol. 14:1403-1406.

Zamzami et al., "The thiol cross linking agent diamide overcomes the apoptosis-inhibitory effect of Bcl-2 by enforcing mitochondrial permeability transition," Oncogene, 16:1055-1063 (1998).

Ruffolo and Shore, BCL-2 Selectively Interacts with the BID-Induced Open Conformer of BAK, Inhibiting BAK Auto-Oligomerization, J. Biol. Chem., 278(27):25039-25045, 2003.

Lee, et al. A novel BH3 ligand that selectively targets Mcl-1 reveals that apoptosis can proceed without Mcl-1 degradation. J Cell Biol. Jan. 28, 2008;180(2):341-355.

Sanchez-Garcia, et al. Tumorigenic activity of the BCR-ABL oncogenes is mediated by BCL2. Proc Natl Acad Sci U S A. Jun. 6, 1995;92(12):5287-91.

Office action dated Dec. 29, 2011 for U.S. Appl. No. 12/233,555.

Berendsen, H.J. A glimpse of the Holy Grail? Science. Oct. 23, 1998;282(5389):642-3.

Bradley, et al. Limits of cooperativity in a structurally modular protein: response of the Notch ankyrin domain to analogous alanine substitutions in each repeat. J Mol Biol. Nov. 22, 2002;324(2):373-86.

Designing Custom Peptide. from SIGMA Genosys, pp. 1-2. Accessed Dec. 16, 2004.

International search report dated Nov. 30, 2009 for PCT Application No. US2009/02225.

Leduc, et al. Helix-stabilized cyclic peptides as selective inhibitors of steroid receptor-coactivator interactions. Proc Natl Acad Sci U S A. Sep. 30, 2003;100(20):11273-8.

Ngo, et al. Computational complexity, protein structure predictioni, and the levinthal paradox. In The Protein Folding Problem and Tertiary Structure Prediction. K. Merc Jr, et al. Eds. 1994; 491-495.

Office action dated Feb. 9, 2012 for U.S. Appl. No. 12/420,816.

Office action dated Feb. 17, 2011 for U.S. Appl. No. 12/796,212.

Office action dated Oct. 18, 2011 for U.S. Appl. No. 12/796,212.

Rudinger, J. Characteristics of the amino acids as components of a peptide hormone sequence. In Peptide Hormones. J. A. Parsons, ed. University Park Press. Jun. 1976; pp. 1-7.

Schinzel, et al. The phosphate recognition site of *Escherichia Coli* maltodextrin phosphorylase. FEBS Lett. Jul. 29, 1991;286(1-2):125-8.

Tanaka, M. Design and synthesis of non-proteinogenic amino acids and secondary structures of their peptides. Yakugaku Zasshi. Oct. 2006;126(10):931-44.

Voet, et al. Biochemistry, Second Edition. John Wiley & Sons, Inc. 1995; pp. 235-241.

* cited by examiner

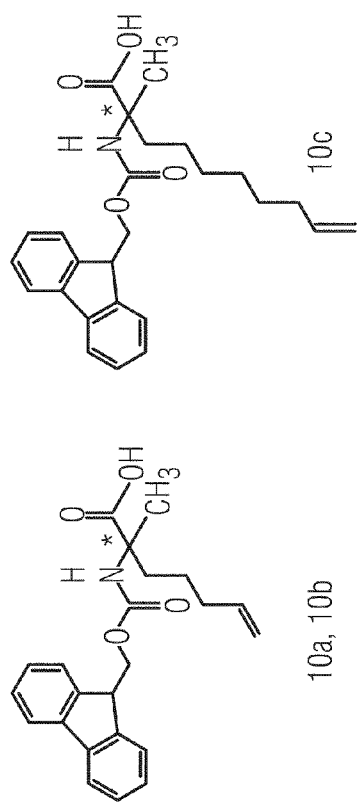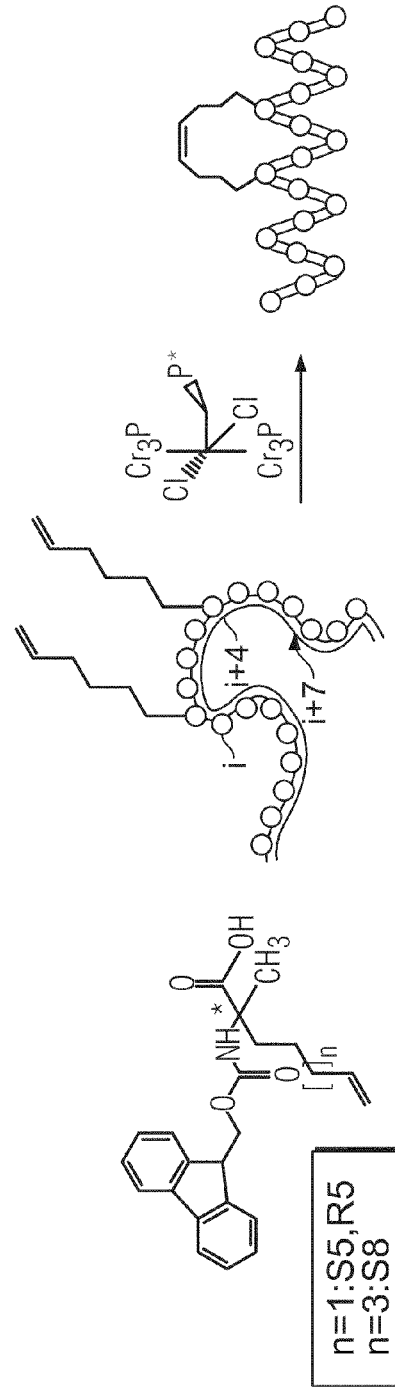
FIG. 4A
FIG. 4B

| Compound | Sequence | HRMS | |
|---|---|---|---|
| SAHB3$_{BID}$A | E D I I R N I A R H L A * V G D * N$_L$ D R S I W | 2752.8 | |
| SAHB3$_{BID(-E,W)}$A | D I I R N I A R H L A * V G D * N$_L$ D R S I | 2436.6 | |
| SAHB3$_{BID(G \rightarrow E)}$A | E D I I R N I A R H L A * V E D * N$_L$ D R S I W | 2824.8 | |
| SAHB3$_{BID(-E,W,G \rightarrow E)}$A | D I I R N I A R H L A * V E D * N$_L$ D R S I | 2507 | |
| SAHB3$_{BID(G \rightarrow S)}$A | D I I R N I A R H L A * V S D * N$_L$ D R S I W | 2654.7 | |
| FITC-SAHB3$_{BID}$A | FITC-A$_\beta$-E D I I R N I A R H L A * V G D * N$_L$ D R S I W | 3169.6 | |
| FITC-SAHB3$_{BID(G \rightarrow E)}$A | FITC-A$_\beta$-E D I I R N I A R H L A * V E D * N$_L$ D R S I W | 3242.8 | * = 10a |
| Biot-SAHB3$_{BID}$A | K(Biot)- D I I R N I A R H L A * V G D * N$_L$ D R S I W | 3108.9 | # = 10b |
| Biot-SAHB3$_{BID(G \rightarrow E)}$A | K(Biot)- D I I R N I A R H L A * V E D * N$_L$ D R S I W | 3179.1 | ^ = 10c |
| SAHB3$_{BID}$B | E D I I R N I * R H L * Q V G D S N$_L$ D R S I W | 2825.7 | |
| SAHB3$_{BID(-E,W)}$B | D I I R N I * R H L * Q V G D S N$_L$ D R S I | 2511.6 | |
| SAHB3$_{BID(tr)}$B | R N I * R H L * Q V G D S N$_L$ D R W | 2155.8 | |
| SAHB3$_{BID(G \rightarrow E)}$B | E D I I R N I * R H L * Q V E D S N$_L$ D R S I W | 2710.8 | |
| Biot-SAHB3$_{BID}$B | K(Biot)- D I I R N I * R H L * Q V G D S N$_L$ D R S I W | 3179.73 | |
| Biot-SAHB3$_{BID(G \rightarrow E)}$B | K(Biot)- D I I R N I * R H L * Q V E D S N$_L$ D R S I | 3066.7 | |
| SAHB3$_{BID}$C | E D I I R N I A * H L A * V G D S N$_L$ D R S I W | 2683.5 | |
| SAHB3$_{BID}$D | E D I I R N I A R # L A Q V G D ^ N$_L$ D R S I W | 2785.8 | |
| SAHB3$_{BID}$E | E D I I # N I A # H L A * V G D * N$_L$ D R S I W | 2691.8 | |
| SAHB3$_{BAD}$A | N L W A A Q R Y G R F I R * N$_L$ S D * F V D S F K K | 3090.8 | |
| FITC-SAHB3$_{BID(-EW)}$A | FITC-A$_\beta$ D I I R N I A R H L A * V G D * N$_L$ D R S I | 2855.4 | |
| FITC-SAHB3$_{BID(-EW,G \rightarrow E)}$A | FITC-A$_\beta$ D I I R N I A R H L A * V E D * N$_L$ D R S I | 2927.5 | |
| SAHB3$_{BID(-EW,L \rightarrow A,D \rightarrow A)}$A | D I I R N I A R H A A * V G A * N$_L$ D R S I | 2352.4 | |
| SAHB3$_{BIM}$A | I W I A Q E L R * I G D * F N A Y Y A R R | 2645.4 | |
| FITC-SAHB3$_{BIM}$A | FITC-A$_\beta$ I W I A Q E L R * I G D * F N A Y Y A R R | 3063.5 | |
| FITC-SAHB3$_{BAD}$A | FITC-A$_\beta$ N L W A A Q R Y G R E L R * N$_L$ S D * F V D S F K K | 3507.7 | |

FIG. 5A

| Compound | Sequence |
|---|---|
| BID BH3 | EDIIRNIARHLAQVGDSN$_L$DRSIW |
| SAHB$_A$ | EDIIRNIARHLA*VGD*N$_L$DRSIW |
| SAHB$_{A(G \rightarrow E)}$ | EDIIRNIARHLA*VED*N$_L$DRSIW |
| SAHB$_B$ | EDIIRNI*RHL*QVGDSN$_L$DRSIW |
| SAHB$_C$ | EDIIRNIA*HLA*VGDSN$_L$DRSIW |
| SAHB$_D$ | EDIIRNIAR⊗LAQVGD*N$_L$DRSIW |

*=S5, ⊗=R5, *=S8

SAHB3a

SAHB3aG-->E

BID BH3

BID 6

SAHB3a

Tom20

Overlay

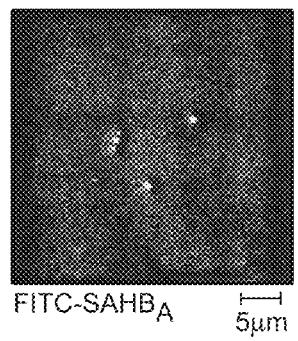
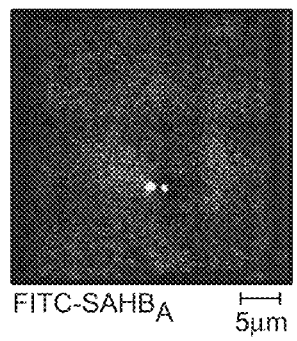
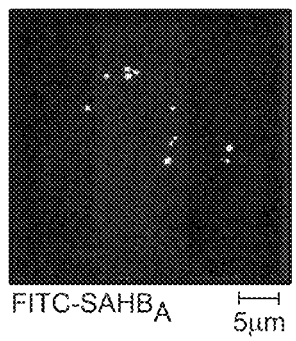
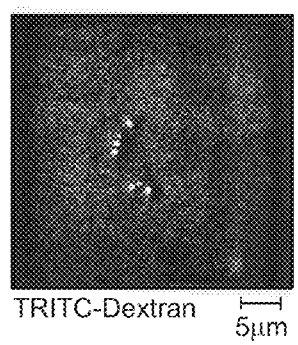
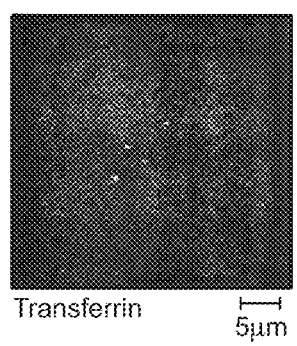
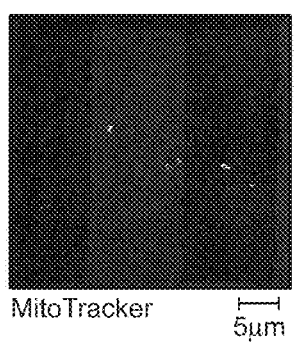
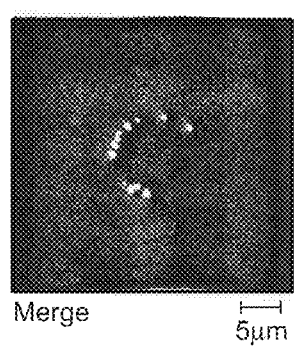
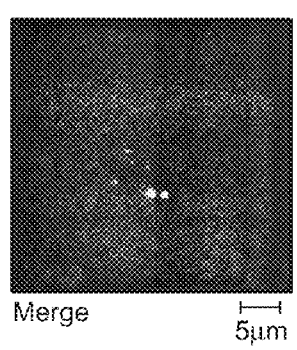
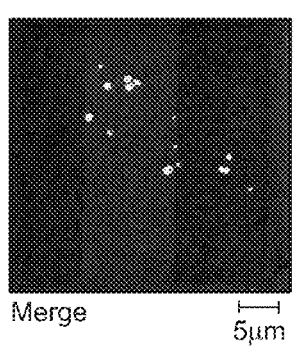
FIG. 21A     FIG. 21B     FIG. 21C

```
h8bc3    MARARQEGSSPEPVEGLARDGPRPFPLGRLVPSAVSCGLCSPGLAAAPAA      50
m8bc3    MARARQEGSSPEPVEGLARDSPRPFPLGRLMPSAVSCSLCSPGLPAAPAA      50 h8bc3    PTLLPAAYLCAPTAPPAVTAALGGSRWPGGPRSRPRGPRPDGPQPSLSLA     100
m8bc3    PALLPAAYLCAPTAPPAVTAALGGPRWPGGHRSRPRGPRPDGPQPSLSPA     100 h8bc3    EQHLESPVPSAPGALAGGPTQAAPGVRGEEEQWAREIGAQLRRMADDLNA     150
m8bc3    QQHLESPVPSAPEALAGGPTQAAPGVRVEEEEWAREIGAQLRRMADDLNA     150
                                            BH3
h8bc3    QYERRRQEEQQRHRPSPWRVLYNLIMQLLPLPRGHRAPEMEPN            193
m8bc3    QYERRRQEEQHRHRPSPWRVMYNLFMQLLPLPRQPGAPEMEPN            193
```

FIG. 28A-1

```
                       BH3
Bbc3   133   WAREIGAQLRRMADDLNAQY
EgI-1   50   IGYEIGSKLAAMCDDFDAQM
Bsd    106   AAQRYGRELRRMSDEFVDSF
BIm     84   PEIWIAQELRRIGDEFNAYY
BId     82   IIRNIARHLAQVGDSMDRSI
BIk     53   GSDALALRLACIGDEMDVSL
Hrk     29   AAQLTAARLKALGDELHQRT
```

FIG. 28A-2

```
BIK    56    ALALRLACIGDEMDVSLR
Bim1   87    WIAQELRRIGDEFNAYYA
Noxa   24    ECATQLRRFGDKLNFRQK
Bid    85    NIARHLAQVGDSMDRSIP
Bad   109    RYGRELRRMSDEFVDSFK
EGL-1  53    EIGSKLAAMCDDFDAQMM
```
FIG. 28B-1
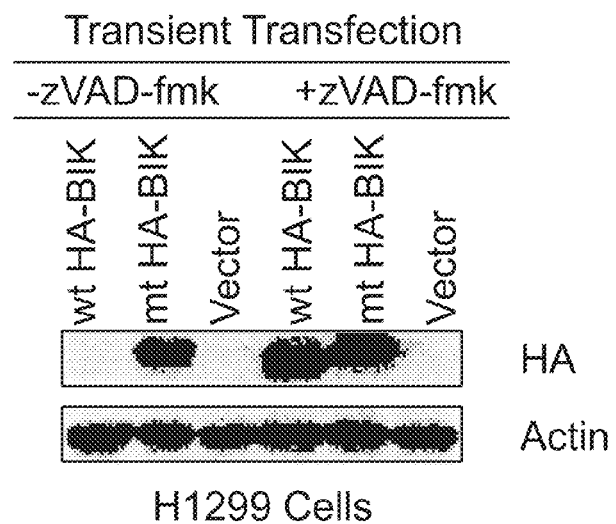
FIG. 28B-2
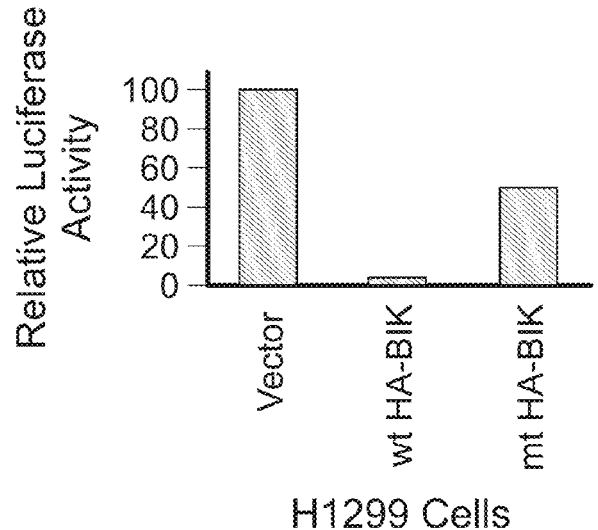
FIG. 28B-3

```
hBid    37   LDALGHELP    45  } BH3-B
mBid    35   LEVLGRELP    43 hBid    90   LAQVGDSMD    98
mBid    90   LAQIGDEMD    98
hBik    61   LACIGDEMD    69
hBimL   92   LRRIGDEFN   100
hHrk    37   LKALGDELH    45  } BH3
hBad   113   LRRMSDEFV   121
hBak    78   LAIIGDDIN    86
hBax    63   LKRIGDELD    71
mMtd    71   LLRLGDELE    79
```

```
  1   MTLRLLEDWCRGMDMNPRKALLIAGISQSCSVAEIEEAL    hMAP-1
  1   MTLRLLEDWCRGMDMNPRKALLVAGIPPTCGVADIEEAL    mMAP-1
  1   MAMTLLEDWCRGMDVNSQRALLVWGIPVNCDEAEIEETL    hMa1
  1   MALALLEDWCRIMSVDEQKSLMVTGIPADFEEAEIQEVL    hMa2

40   QAGLAPLGEYRLLGRMFRRDENRKVALVGLTAETSHALV    hMAP-1
 40   QAGLAPLGEHRLLGRMFRRDENKNVALIGLTVETGSALV    mMAP-1
 40   QAAMPQVS-YRMLGRMFWREENAKAALLELTGAVDYAAI    hMa1
 40   QETLKSLGRYRLLGKIFRRQENANAVLLELLEDTDVSAI    hMa2
                                    B26▶
 79   PKEIPGKGGIWRVIFKPPDPDNTFLSRLNEFLAGEGMTV    hMAP-1
 79   PKEIPAKGGVWRVIFKPPDTDSDFLCRLNEFLKGEGMTM    mMAP-1
 78   PREMPGKGGVWKVLFKPPTSDAEFLERLHLFLAREGWTV    hMa1
 79   PSEVQGKGGVWKVIFKTPNQDTEFLERLNLFLEKEGQTV    hMa2
     B100▶
118   GELSRALGHENGSLDPEQG-MIPEMWAPMLAQAL-EALQ    hMAP-1
118   CELTRVLGNRNDPLGLDPGIMIPEIRAPMLAQALNEALK    mMAP-1
117   QDVARVLGFQNPT--PTPG---PEMPAEMLNYILDNVIQ    hMa1
118   SGMFRALGQEGVSPAVPCI-SPELLAHLLGQAMAHAPQ     hMa2

155   PALQCLKYKKLRVFSGRISPEPGEEEFGRWMFHTTQMIK    hMAP-1
157   PTLQYLRYKKLSVFSGRDPPGPGEEEFESWMFHTSQVMK    mMAP-1
151   PLVESIWYKRLTLFSGKGHPRAWRGNFDPWLEHTMEVLE    hMa1
156   PLLP-MRYRKLRVFSGSAVPAPEEESFEVWLEQATEIVK    hMa2

194   AWQVPDVEKRRRLLESLRGPALDIRVLKINNPLITVDC    hMAP-1
196   TWQVSDVEKRRRLIESLRGPAFEIIRVLKINNPFITVAE    mMAP-1
190   EWQVSDVEKRRRLMESLRGPAADVIRILKSNNPAITTAE    hMa1
194   EWPVTEAEKKRWLAESLRGPALDLMHIVQADNPSISVEE    hMa2

233   CLQALDCVFGVTDNPRELQVKYLTTYIKDCEKLSAYVLR    hMAP-1
235   CLKTLETIFGIIDNPRALQVKYLTTYQKTDEKLSAYVLR    mMAP-1
229   CLKALEQVFGSVESSRDAQIKFLNTYQNPGEKLSAYVIR    hMa1
233   CLEAFKQVFGSLESRRTAQVRYLKTYQEEGEKVSAYVLR    hMa2

272   LEPLLQKLVQRGAIERDAVNQARLDQVIAGAVHKT-IRR    hMAP-1
274   LEPLLQKLVQKGAIEKEVVNQARLDQVIAGAVHKS-VRR    mMAP-1
268   LEPLLQKVVEKGAIDKDNVNQARLEQVIAGANHSGAIRR    hMa1
272   LETLLRRAVEKRAIPRRIADQVRLEQVMAGATLNQMLWC    hMa2

310   CLN-LPCDGPAPGFLQLLVLIKDYCAAC---CCCALLQA    hMAP-1
312   ELG-LPEGSPAPGLLQLLTLIKDKEA-E---EEEVLLQA    mMAP-1
307   QLW-LTGAGEGPGPKPL---------------------    hMa1
311   RLRELKDQGPPPSFLELMKVIREEEEEEASFENESIEEP    hMa2

345   ILEGNFT                                    hMAP-1
346   ELEGYCT                                    mMAP-1
323   SVAGADP                                    hMa1
350   EERDGYGRWNHEGDD                            hMa2
```

FIG. 28D-1

```
                      BH3-like
MAP-1  1 ☐━━━━━━━━━━━━┿━┿━━━━━━━━━━┐351 hMAP-1  120  L S RALGH E  127
mMAP-1  120  L T RVLGN R  127
hBid     37  L - DALGH E   43 ⎫
mBid     35  L - EVLGR E   41 ⎭ BH3-B
hHrk     37  L - KALGD E   43 ⎫
hBid     90  L - AQVGD S   96 ⎪
hBax     63  L - KRIGD E   69 ⎬ BH3
hBimL    92  L - RRIGD E   98 ⎪
hBik     61  L - AQIGD E   67 ⎭
```

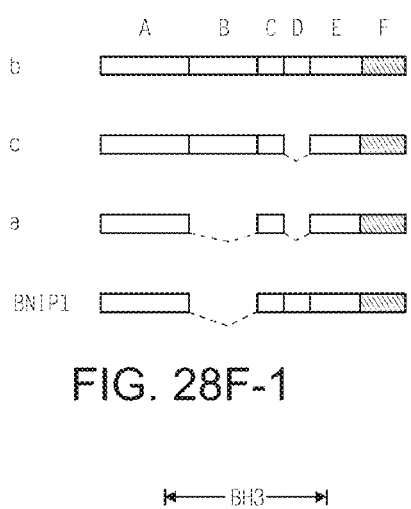

FIG. 28F-1

```
              |←——BH3——→|
BNIP1b   154  KAELLQGGDLLRQR   167
BIK       56  ALRLACIGDEMDVS    69
BLK       52  ALRLACIGDEMDLC    65
BID       87  ARHLAQVGDSMDRS   100
BAK       75  GRQLAIIGDDINRR    88
HRK       34  AARLKALCDELHQR    47
BAX       60  SECLRRIGDELDSN    73
BIML      89  AQELRRIGDEFNAY   102
BOK       68  CTVLLRLGDELEQI    81
BCL2L1    87  KQALREAGDEFELR   100
BCL2      94  HLTLRQAGDDFSRR   107
MCL1     210  LETLRRVGDGVQRN   223
                   *   **
```

FIG. 28F-3

-1.35kb

FIG. 28F-4

```
MAAPQDVNVRICNQZIVKTDLEVKALIQDI         30

RDCSGPLSALTRLNTKVKRKTQQLRNRIQP         60
                             |-

VLYQRATINZASTITTXLYYELTDFSSTQN         90
-- Present only in BNIP1b & BNIP1e --

QFNSPTYFVTFSQLZQLAKZQDKXSEKQLL        120
------------|

LQXVENRKKQNLKNQASWRKANLTCKLAID        150
|------ Present only in

|-----BH3-----|
NIRKANLLQQQDLLAQRXTYKKSLAQYSST        180
BNIP1 & BNIP1b---|

|--------- ANK1 ----------
ITKSLNGISROKAQQVQQSEEANQSLVTSS        210

----------| |----------- ANK2 --
RTTLDAKEETXSNSQTTQLQRKLTTKYMRR        240

----| |----------- TM ---------
ZLTDKLLIFLALRLTLATVLYIVKKRLFPF        271
-|
L*
```

FIG. 28F-2

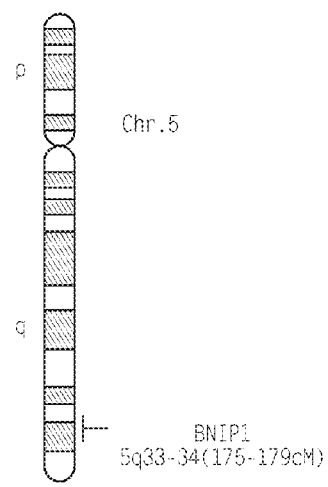

FIG. 28F-5

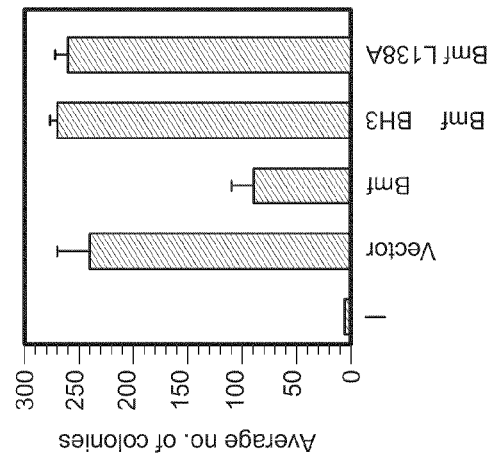
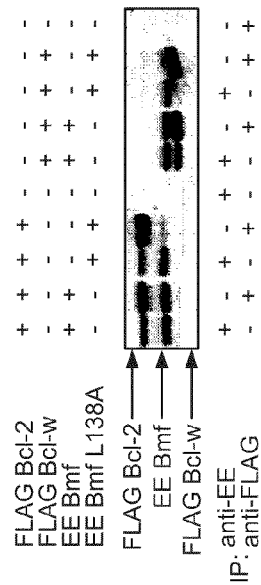
FIG. 28G-2
FIG. 28G-5
FIG. 28G-1
FIG. 28G-4
FIG. 28G-3

US 8,198,405 B2

STABILIZED ALPHA HELICAL PEPTIDES AND USES THEREOF

CLAIM OF PRIORITY

This application is a continuation of and claims priority from U.S. application Ser. No. 10/981,873, filed Nov. 5, 2004, now U.S. Pat. No. 7,723,469, which claims the benefit of U.S. Provisional Application Ser. No. 60/517,848, filed on Nov. 5, 2003, and U.S. Provisional Application Ser. No. 60/591,548, filed on Jul. 27, 2004. The contents of these prior applications are hereby incorporated by reference in their entirety for all purposes.

STATEMENT AS TO FEDERALLY SPONSORED RESEARCH

This invention was made with government support under NIH funding R01 CA050239 and K08 HL074049. The government has certain rights in the invention.

BACKGROUND

Apoptosis, or programmed cell death, plays a critical role in the development and maintenance of homeostasis in all multicellular organisms. Susceptibility to apoptosis varies markedly among cells and is influenced by both external and internal cellular events. Positive and negative regulator proteins that mediate cell fate have been defined, and dysregulation of these protein signaling networks has been documented in the pathogenesis of a wide spectrum of human diseases, including a variety of cancers. BCL-2 is the founding member of this family of apoptotic proteins and was first identified at the chromosomal breakpoint of t(14;18)(q32;q21) lymphomas (Bakhashi et al. 1985 *Cell* 41:899; Cleary et al. 1985 *Proc. Nat'l. Acad. Sci. USA* 82:7439).

Gene rearrangement places BCL-2 under the transcriptional control of the immunoglobulin heavy chain locus, generating inappropriately high levels of BCL-2 and resultant pathologic cell survival. Such aberrations in apoptosis have been identified in lymphocytic and myelogenous leukemias and a host of other malignancies, and have been linked to tumor progression and acquired resistance to chemotherapy-induced apoptosis. The BCL-2 family of proteins has expanded significantly and includes both pro- and anti-apoptotic molecules that provide the checks and balances that govern susceptibility to cell death (FIG. 1). Not surprisingly, apoptotic proteins have become key targets for the development of therapeutics to both prevent precipitous cell death in diseases of cell loss and activate cell death pathways in malignancy.

The BCL-2 family is defined by the presence of up to four conserved "BCL-2 homology" (BH) domains designated BH1, BH2, BH3, and BH4, all of which include α-helical segments (Chittenden et al. 1995 *EMBO* 14:5589; Wang et al. 1996 *Genes Dev.* 10:2859). Anti-apoptotic proteins, such as BCL-2 and BCL-$X_L$, display sequence conservation in all BH domains. Pro-apoptotic proteins are divided into "multidomain" members (e.g. BAK, BAX), which possess homology in the BH1, BH2, and BH3 domains, and the "BH3-domain only" members (e.g. BID, BAD, BIM, BIK, NOXA, PUMA), that contain sequence homology exclusively in the BH3 amphipathic α-helical segment. BCL-2 family members have the capacity to form homo- and heterodimers, suggesting that competitive binding and the ratio between pro- and anti-apoptotic protein levels dictates susceptibility to death stimuli. Anti-apoptotic proteins function to protect cells from pro-apoptotic excess, i.e., excessive programmed cell death. Additional "security" measures include regulating transcription of pro-apoptotic proteins and maintaining them as inactive conformers, requiring either proteolytic activation, dephosphorylation, or ligand-induced conformational change to activate pro-death functions. In certain cell types, death signals received at the plasma membrane trigger apoptosis via a mitochondrial pathway (FIG. 2). The mitochondria can serve as a gatekeeper of cell death by sequestering cytochrome c, a critical component of a cytosolic complex which activates caspase 9, leading to fatal downstream proteolytic events. Multidomain proteins such as BCL-2/BCL-$X_L$ and BAK/BAX play dueling roles of guardian and executioner at the mitochondrial membrane, with their activities further regulated by upstream BH3-only members of the BCL-2 family. For example, BID is a member of the "BH3-domain only" subset of pro-apoptotic proteins, and transmits death signals received at the plasma membrane to effector pro-apoptotic proteins at the mitochondrial membrane. BID has the unique capability of interacting with both pro- and anti-apoptotic proteins, and upon activation by caspase 8, triggers cytochrome c release and mitochondrial apoptosis. Deletion and mutagenesis studies determined that the amphipathic α-helical BH3 segment of pro-apoptotic family members functions as a death domain and thus represents a critical structural motif for interacting with multidomain apoptotic proteins. Structural studies have demonstrated that the BH3 helix interacts with anti-apoptotic proteins by inserting into a hydrophobic groove formed by the interface of BH1, 2 and 3 domains. Activated BID can be bound and sequestered by anti-apoptotic proteins (e.g., BCL-2 and BCL-$X_L$) and can trigger activation of the pro-apoptotic proteins BAX and BAK, leading to cytochrome c release and a mitochondrial apoptosis program.

BAD is also a "BH3-domain only" pro-apoptotic family member whose expression likewise triggers the activation of BAX/BAK. In contrast to BID, however, BAD displays preferential binding to anti-apoptotic members, BCL-2 and BCL-$X_L$. Whereas the BAD BH3 domain exhibits high affinity binding to BCL-2, BAD BH3 peptide is unable to activate cytochrome c release from mitochondria in vitro, suggesting that BAD is not a direct activator of BAX/BAK. Mitochondria that overexpress BCL-2 are resistant to BID-induced cytochrome c release, but co-treatment with BAD can restore BID sensitivity. Induction of mitochondrial apoptosis by BAD appears to result from either: (1) displacement of BAX/BAK activators, such as BID and BID-like proteins, from the BCL-2/BCL-$X_L$ binding pocket, or (2) selective occupation of the BCL-2/BCL-$X_L$ binding pocket by BAD to prevent sequestration of BID-like proteins by anti-apoptotic proteins. Thus, two classes of "BH3-domain only" proteins have emerged, BID-like proteins that directly activate mitochondrial apoptosis, and BAD-like proteins, that have the capacity to sensitize mitochondria to BID-like pro-apoptotics by occupying the binding pockets of multidomain anti-apoptotic proteins.

The objective of identifying or generating small molecules to probe apoptotic protein functions in vitro and specifically manipulate apoptotic pathways in vivo has been challenging. High throughput screening has identified several molecules that inhibit the interaction of the BAK BH3 domain with BCL-$X_L$ at micromolar affinities. In addition to the potential drawback of identifying low affinity compounds, the technique is limited in its ability to generate panels of compounds tailored to the subtle binding specificities of individual members of protein families. Alternate approaches to manipulating apoptosis pathways have derived from peptide engineering, a technique that uses non-specific peptide sequence to generate compounds with desired three-dimensional structures. One application of this technique involved the generation of "pro-apoptotic" α-helices comprised of nonspecific peptide sequence used to induce cell death by disrupting mitochondrial membranes.

The alpha-helix is one of the major structural components of proteins and is often found at the interface of protein contacts, participating in a wide variety of intermolecular biological recognition events. Theoretically, helical peptides, such as the BH3 helix, could be used to selectively interfere with or stabilize protein-protein interactions, and thereby manipulate physiologic processes. However, biologically active helical motifs within proteins typically have little structure when taken out of the context of the full-length protein and placed in solution. Thus, the efficacy of peptide fragments of proteins as in vivo reagents has been compromised by loss of helical secondary structure, susceptibility to proteolytic degradation, and inability to penetrate intact cells. Whereas several approaches to covalent helix stabilization have been reported, most methodologies involve polar and/or labile crosslinks (Phelan et al. 1997 *J. Am. Chem. Soc.* 119: 455; Leuc et al. 2003 *Proc. Nat'l. Acad. Sci. USA* 100:11273; Bracken et al., 1994 *J. Am. Chem. Soc.* 116:6432; Yan et al. 2004 *Bioorg. Med. Chem.* 14:1403). Subsequently, Verdine and colleagues developed an alternate metathesis-based approach, which employed α,α-disubstituted non-natural amino acids containing alkyl tethers (Schafineister et al., 2000 *J. Am. Chem. Soc.* 122:5891; Blackwell et al. 1994 *Angew Chem. Int. Ed.* 37:3281).

SUMMARY

This invention is based, in part, on the discovery that stably cross-linking a polypeptide having at least two modified amino acids (a process termed "hydrocarbon stapling") can help to conformationally bestow the native secondary structure of that polypeptide. For example, cross-linking a polypeptide predisposed to have an alpha-helical secondary structure can constrain the polypeptide to its native alpha-helical conformation. The constrained secondary structure can increase resistance of the polypeptide to proteolytic cleavage and also increase hydrophobicity. Surprisingly, in some instances, the polypeptides can penetrate the cell membrane (e.g., through an energy-dependent transport mechanism, e.g., pinocytosis). Accordingly, the crosslinked polypeptides described herein can have improved biological activity relative to a corresponding uncrosslinked polypeptide. For example the cross-linked polypeptide can include an alpha-helical domain of a BCL-2 family member polypeptide (e.g., BID-BH3 domain), which can bind to BAK/BAX and/or BCL-2/BCL-$X_L$ to promote apoptosis in a subject. In some instances, the crosslinked polypeptide can be used to inhibit apoptosis. The cross-linked polypeptides described herein can be used therapeutically, e.g., to treat cancer in a subject.

In one aspect, the invention features polypeptide of formula (I),

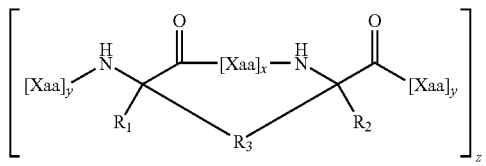

formula (I)

wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4$—K—$R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

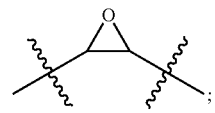

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid.

In some instances, the polypeptide binds to a BCL-2 family protein. The polypeptide can bind to an anti-apoptotic protein. The polypeptide can bind to a pro-apoptotic protein. The polypeptide can bind and activate BAX or BAK. In some instances, the polypeptide binds to a BH1, BH2 and/or BH3 domain.

In some instances, the polypeptide activates cell death, for example the polypeptide can trigger cytochrome c release and activate mitochondrial cell death.

In other instances, the polypeptide can inhibit cell death.

In some instances, the polypeptide includes a BH3 domain.

In some instances, x is 2, 3, or 6.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.

In some instances, $R_3$ is $C_{11}$ alkyl and x is 6.

In some instances, $R_3$ is alkenyl (e.g., $C_8$ alkenyl) and x is 3.

In some instances x is 6 and $R_3$ is $C_{11}$ alkenyl.

In some instances, $R_3$ is a straight chain alkyl, alkenyl, or alkynyl.

In some instances $R_3$ is —$CH_2$—$CH_2$—$CH_2$—CH=CH—$CH_2$—$CH_2$—$CH_2$—.

In certain embodiments the two alpha, alpha disubstituted stereocenters are both in the R configuration or S configuration (e.g., i, i+4 cross-link), or one stereocenter is R and the other is S (e.g., i, i+7 cross-link). Thus, where formula I is depicted as

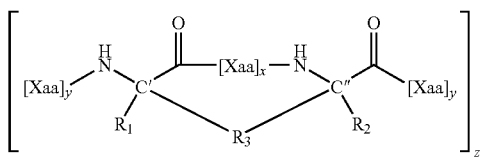
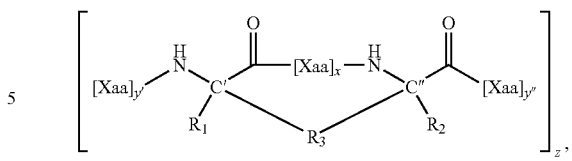

the C' and C" disubstituted stereocenters can both be in the R configuration or they can both be in the S configuration, for example when X is 3. When x is 6, the C' disubstituted stereocenter is in the R configuration and the C" disubstituted stereocenter is in the S configuration. The $R_3$ double bond may be in the E or Z stereochemical configuration.

In some instances $R_3$ is $[R_4—K—R_4]_n$; and $R_4$ is a straight chain alkyl, alkenyl, or alkynyl.

In some instances, the polypeptide includes an amino acid sequence which is at least about 60% (70%, 80%, 85%, 90%, 95% or 98%) identical to the amino acid sequence of EDIIRNI*RHL*QVGDSN$_L$DRSIW (SEQ ID NO: 99), wherein * is a tethered amino acid. For example, there can be 1, 2, 3, 4, 5 or more amino acid changes, e.g., conservative changes.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). In some instances, the polypeptide can include an amino acid sequence which is at least about 60% (70%, 80%, 85%, 90%, 95% or 98%) identical to the amino acid sequence of EDIIRNIARHLA*VGD*N$_L$DRSIW (SEQ ID NO: 92), wherein * is a tethered amino acid. For example, there can be 1, 2, 3, 4, 5 or more amino acid changes, e.g., conservative changes. In some instances, the polypeptide is transported through the cell membrane (e.g., through an active transport or endocytotic mechanism or by passive transport).

In some embodiments the polypeptide comprises at least 5, 6, 7, 8, 9, 10, 11, 12, 13, 14, 15, 16, 17, 18, 19, 20, 25, 50, or more contiguous amino acids of a BCL-2 or BCL-2 like domain, e.g., a BH3 domain or BH3-like domain, e.g., a polypeptide depicted in any of FIGS. 5a, 5b, and 28a-28h. Each $[Xaa]_y$ is a peptide that can independently comprise at least 5, 6, 7, 8, 9, 10, 11, 12, 13, 14, 15, 16, 17, 18, 19, 20, 25 or more contiguous amino acids of a BCL-2 or BCL-2 like domain, e.g., a BH3 domain or BH3-like domain, e.g., a polypeptide depicted in any of FIGS. 5a, 5b, and 28a-28h. $[Xaa]_x$ is a peptide that can comprise 3 or 6 contiguous amino acids of acids of a BCL-2 or BCL-2 like domain, e.g., a BH3 domain or BH3-like domain, e.g., a polypeptide depicted in any of FIGS. 5a, 5b, and 28a-28h.

The polypeptide can comprise 8, 9, 10, 11, 12, 13, 14, 15, 16, 17, 18, 19, 20, 25, 30, 35, 40, 45, 50 contiguous amino acids of acids of a BCL-2 or BCL-2 like domain, e.g., a BH3 domain or BH3-like domain, e.g., a polypeptide depicted in any of FIGS. 5a, 5b, and 28a-28h (SEQ ID Nos: 1-118) wherein two amino acids that are separated by three amino acids (or six amino acids) are replaced by amino acid substitutes that are linked via $R_3$. Thus, at least two amino acids can be replaced by tethered amino acids or tethered amino acid substitutes. Thus, where formula I is depicted as $[Xaa]_y$ and $[Xaa]_{y'}$ can each comprise contiguous polypeptide sequences from the same or different BCL-2 or BCL-2 like domains.

The invention features cross-linked polypeptides comprising 10 (11, 12, 13, 14, 15, 16, 17, 18, 19, 20, 21, 22, 23, 24, 25, 30, 35, 40, 45, 50 or more) contiguous amino acids of a BCL-2 or BCL-2 like domain, e.g., a BH3 domain or BH3-like domain, e.g., a polypeptide depicted in any of FIGS. 5a, 5b, and 28a-28h (SEQ ID Nos: 1-118) wherein the alpha carbons of two amino acids that are separated by three amino acids (or six amino acids) are linked via $R_3$, one of the two alpha carbons is substituted by $R_1$ and the other is substituted by $R_2$ and each is linked via peptide bonds to additional amino acids.

In some embodiments the polypeptide has apoptotic activity.

In some instances, the polypeptide also includes a fluorescent moiety or radioisotope.

In some instances, the polypeptide includes 23 amino acids; $R_1$ and $R_2$ are methyl; $R_3$ is $C_8$ alkyl, $C_{11}$ alkyl, $C_8$ alkenyl, $C_{11}$ alkenyl, $C_8$ alkynyl, or $C_{11}$ alkynyl; and x is 2, 3, or 6.

In some instances, the polypeptide includes an affinity label, a targeting moiety, and/or a biotin moiety.

In some instances, the polypeptide is a polypeptide selected from the group consisting of the polypeptides depicted in and of FIGS. 28a-h and 5a-b (SEQ ID NOS: 1-118). In another aspect, the invention features a method of making a polypeptide of formula (III), including providing a polypeptide of formula (II); and formula (II)

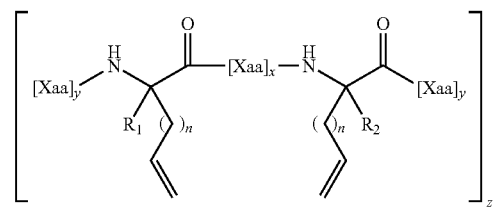

treating the compound of formula (II) with a catalyst to promote a ring closing metathesis, thereby providing a compound of formula (III)

formula (III)

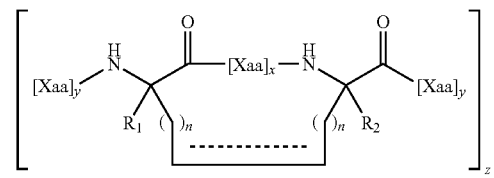

wherein each $R_1$ and $R_2$ are independently H, alkyl, alkenyl, alkynyl, arylalkyl, cycloalkylalkyl; heteroarylalkyl; or heterocyclylalkyl;

each n is independently an integer from 1-15;

x is 2, 3, or 6 each y is independently an integer from 0-100;

z is an integer from 1-10 (e.g., 1, 2, 3, 4, 5, 6, 7, 8, 9, 10); and each Xaa is independently an amino acid;

In some instances, the polypeptide binds to a BCL-2 family member protein.

In some instances, the catalyst is a ruthenium catalyst.

In some instances, the method also includes providing a reducing or oxidizing agent subsequent to the ring closing metathesis.

In some instances, the reducing agent is $H_2$ or the oxidizing agent is osmium tetroxide In some instances, the invention features a method of treating a subject including administering to the subject any of the compounds described herein. In some instances, the method also includes administering an additional therapeutic agent.

In some instances, the invention features a method of treating cancer in a subject including administering to the subject any of the compounds described herein. In some instances, the method also includes administering an additional therapeutic agent.

In some instances, the invention features a library of the compounds described herein.

In some instances, the invention features a method of identifying a candidate compound for the promotion of apoptosis, including;

providing mitochondria;

contacting the mitochondria with any of the compounds described herein;

measuring cytochrome c release; and comparing the cytochrome c release in the presence of the compound to the cytochrome c release in the absence of the compound, wherein an increase in cytochrome c release in the presence of the compound of formula 1 identifies the compound as a candidate compound for the promotion of apoptosis.

In some instances, the invention features a polypeptide of the formula (IV),

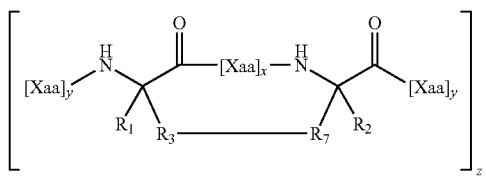

wherein;

each $R_1$ and $R_2$ are independently H, alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$ or a naturally occurring amino acid side chain; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

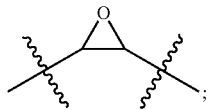

$R_6$ is H, alkyl, or a therapeutic agent;

$R_7$ is alkyl, alkenyl, alkynyl; $[R_4—K—R_4]_n$ or an naturally occurring amino acid side chain; each of which is substituted with 0-6 $R_5$;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid;

In some instances, the invention features a polypeptide of formula (I)

formula (I)

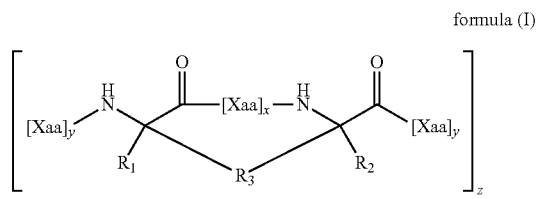

wherein;

each $R_1$ and $R_2$ are independently H, alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkynyl, or alkynyl;

$R_5$ is halo, alkyl, $OR_6$, $N(R_6)_2$, $SP_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

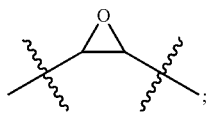

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid;

wherein the polypeptide has at least 5% alpha helicity in aqueous solution as determined by circular dichroism.

In some instances, polypeptide has at least 15%, at least 35%, at least 50%, at least 60%, at least 70%, at least 80% or at least 90% alpha helicity as determined by circular dichroism.

In some instances, the invention features a polypeptide of formula (I), formula (I)

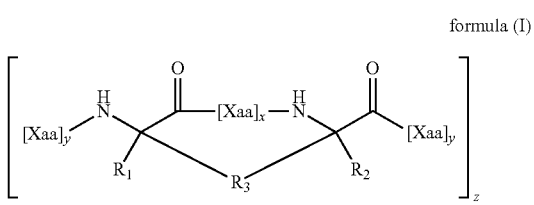

wherein;

each $R_1$ and $R_2$ are independently H, alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkynyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

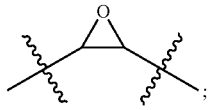

$R_6$ is H, alkyl, or a therapeutic agent;

n is an integer from 1-4;

x is an integer from 2-10;

each y is independently an integer from 0-100;

z is an integer from 1-10 (e.g., 1, 2, 3, 4, 5, 6, 7, 8, 9, 10); and each Xaa is independently an amino acid;

wherein the polypeptide has at least a 1.25-fold increase in alpha helicity as determined by circular dichroism compared to the polypeptide of formula (IV)

formula (IV)

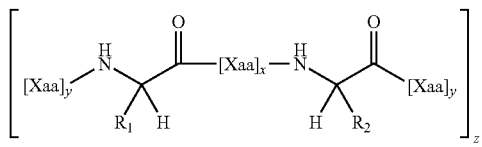

wherein $R_1$, $R_2$, Xaa, x, y, and z are all as defined for formula (I) above.

In some instances, the polypeptide has at least a 1.5-fold, at least 1.75 fold, at least 2.0-fold, at least 2.5-fold, at least 3-fold, or at least 4-fold increase in alpha helicity as determined by circular dichroism compared to the polypeptide of formula (IV).

In some instances, the invention features a method of identifying a candidate compound for the inhibition of apoptosis, including;

providing mitochondria;
contacting the mitochondria with a compound described herein;
measuring cytochrome c release; and
comparing the cytochrome c release in the presence the compound described herein to the cytochrome c release in the absence of the compound described herein, wherein a decrease in cytochrome c release in the presence of the compound described herein identifies the compound described herein as a candidate compound for the inhibition of apoptosis.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject or generation of reagents to study or discover a biological pathway either in vitro or in vivo).

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes.

A "non-essential" amino acid residue is a residue that can be altered from the wild-type sequence of a polypeptide (e.g., a BH3 domain) without abolishing or substantially altering its activity. An "essential" amino acid residue is a residue that, when altered from the wild-type sequence of the polypeptide, results in abolishing or substantially abolishing the polypeptide activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BH3 polypeptide, for example, is preferably replaced with another amino acid residue from the same side chain family.

The symbol "⸻" when used as part of a molecular structure refers to a single bond or a trans or cis double bond.

The term "amino acid side chain" refers to a moiety attached to the α-carbon in an amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., a amide bond). Polypeptides as described herein include full length proteins (e.g., fully processed proteins) as well as shorter amino acids sequences (e.g., fragments of naturally occurring proteins or synthetic polypeptide fragments).

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like.

The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 4a depicts chemical structures of certain non-natural amino acids.

FIG. 4b depicts the crosslinking of synthetic amino acids at positions i and i+4 and i and i+7 by olefin metathesis.

FIG. 5a depicts SAHB3 compounds generated by non-natural amino acid substitution and olefin metathesis (SEQ ID NOs 92-96, 118, 119, 97-108, 120, 121, 110, 111, 122, and 123, respectively).

FIG. 17a shows that FITC-BID BH3 did not label the cells at either temperature, and FITC-SAHB3$_{BID}$A labeled the cells at 37° C. but not 4° C. FIG. 17b shows that FITC-BID helix 6 labels but also permeabilizes the cells in a temperature-independent manner. However, in contrast, FITC-SAHB3$_{BID}$A only labels the cells at 37° C. and does so without cellular permeabilization, consistent with active transport of SAHB3$_{BID}$A via an endocytic pathway.

FIG. 21a and FIG. 21b depicts the results of a study showing that FITC-SAHB3$_{BID}$A colocalizes in live BCL-2 overexpressing Jurkat T-cells with dextran-labeled endosomes but not transferring-labeled endosomes, indicating that FITC-SAHB3$_{BID}$A is imported into cells by fluid-phase pinocytosis.

FIG. 21c depicts the results of a study showing that by 24 hours after treatment, FITC-SAHB3$_{BID}$A colocalizes in the live cells with mitochondria labeled by MitoTracker.

FIG. 27a and FIG. 27b depicts the results of a study showing that SAHB3$_{BID}$A blunts the progression of SEMK2 leukemia relative to vehicle in NOD-SCID mice. A dose responsive effect is noted in FIG. 27a.

Figures 28E-1, 28E-2:
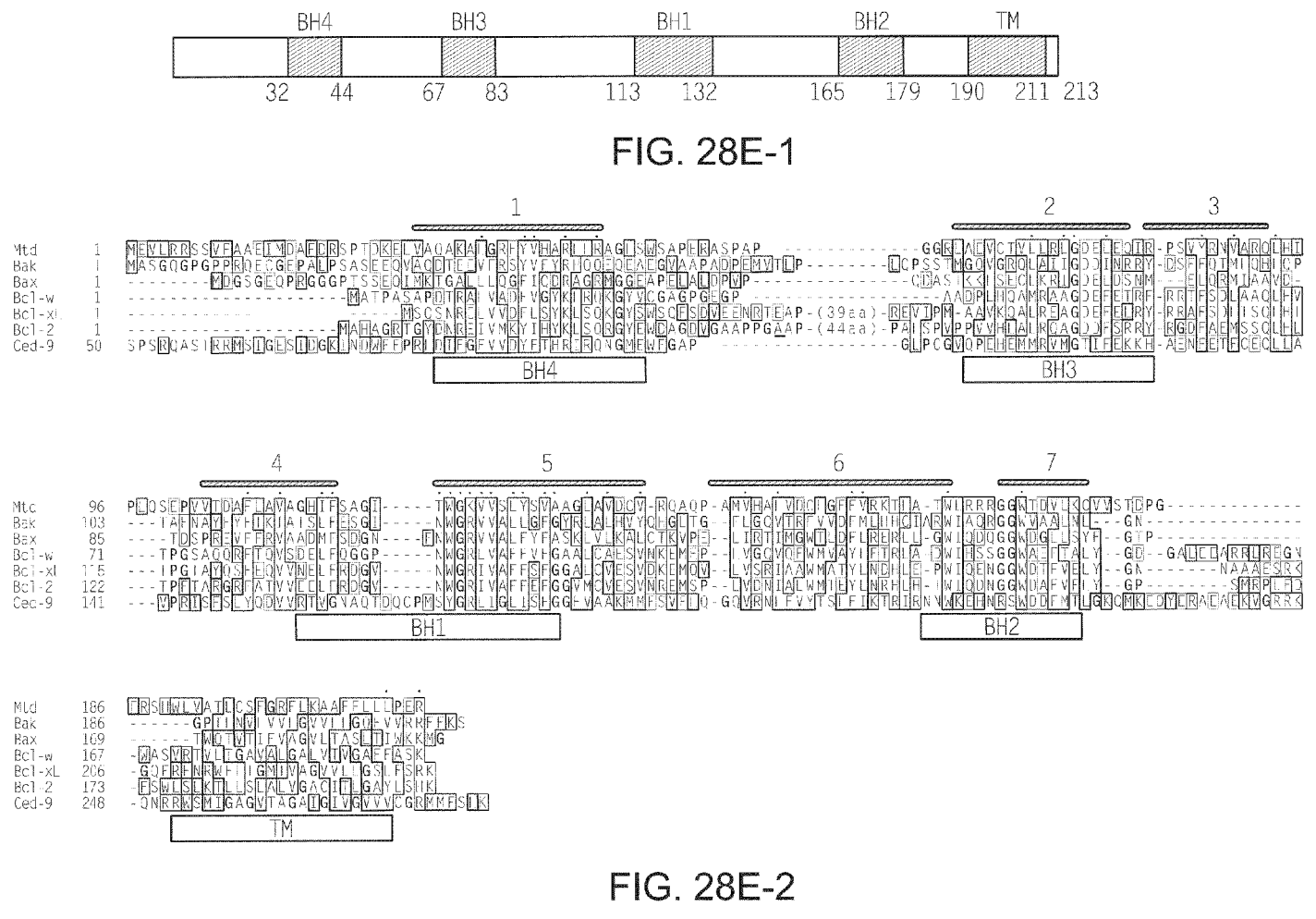

FIG. 28 (B-2) is an image of a Western blot showing BIK expression in H1299 cells. Actin is shown as a loading control.

FIG. 28 (B-3) is a bar graph showing relative luciferase expression in the presence of wild type (wt) or mutant (mt) BIK.

FIG. 28 (C-1) is a schematic showing the BH3 domains of three Bid constructs.

FIG. 28 (C-2) shows the BH3 and BH3-B domains of Bid, Bik, BimL, Hrk, Bad, Bak, Bax, and Mtd (SEQ ID NOs: 16-26).

FIG. 28 (D-1) shows human (h) and murine (m) MAP-1 sequences, Ma1, and Ma2 (SEQ ID NOs: 27-30, respectively).

FIG. 28 (D-2) shows BH3-like sequences of various BCL-2 family member proteins (SEQ ID NOs: 31-39).

FIG. 28 (D-3) shows an image of a Western blot showing MAP-1 expression in various tissues. Actin is shown as control.

FIG. 28 (E-1) is a schematic showing the location of BH4, BH3, BH1, BH2, and TM domains of the sequences shown in FIG. 28 (E-2).

FIG. 28 (E-2) shows various BCL-2 family member protein sequences (SEQ ID NOs: 40-46).

FIG. 28 (F-1) shows schematics of various BNIP1 constructs.

FIG. 28 (F-2) shows SEQ ID NO:47.

FIG. 28 (F-3) shows the BH3 domain sequences of various BCL-2 family member protein sequences (SEQ ID NO: 48-59).

FIG. 28 (F-4) is an image of a gel showing BNIP expression and the molecular weight of BNIP.

FIG. 28 (F-5) is a schematic depicting the chromosomal location of BNIP1.

FIG. 28 (G-1) shows SEQ ID NO: 61 (mouse) and SEQ ID NO: 62 (human).

FIG. 28 (G-2) shows various BCL-2 family member protein sequences (SEQ ID NOs: 62-70).

FIG. 28 (G-3) is an image of a Western blot showing the expression of various BCL-2 family members.

FIG. 28 (G-4) is an image of a Western blot showing Bcl-2 and Bmf immunoprecipitations (IP). Immunoprecipitations was performed using control a control antibody not directed against Bcl-2 and a Bcl-2 specific antibody. Western blots were performed using anti-Bcl-2 and anti-Bmf antibodies.

FIG. 28 (G-5) is a bar graph showing the average number of colonies of cells expressing Bmf, Bmf and Bh3, and Bmf L138A.

FIG. 28 (H) shows an alignment of BH3 domains of select BCL-2 family members (SEQ ID NOs: 71-92).

DETAILED DESCRIPTION

The invention is based, in part, on the discovery that cross-linked alpha helical domain polypeptides of BCL-2 family proteins have improved pharmacological properties over their uncrosslinked counterparts (e.g., increased hydrophobicity, resistance to proteolytic cleavage, binding affinity, in vitro and in vivo biological activity). Moreover, it has been surprisingly discovered that the cross-linked polypeptides can penetrate the cell membrane via a temperature- and energy-dependent transport mechanism (e.g., endocytosis, specifically fluid-phase pinocytosis). The polypeptides include a tether between two non-natural amino acids, which tether significantly enhances the alpha helical secondary structure of the polypeptide. Generally, the tether extends across the length of one or two helical turns (i.e., about 3.4 or about 7 amino acids). Accordingly, amino acids positioned at i and i+3; i and i+4; or i and i+7 are ideal candidates for chemical modification and crosslinking. Thus, for example, where a peptide has the sequence . . . . Xaa$_1$, Xaa$_2$, Xaa$_3$, Xaa$_4$, Xaa$_5$, Xaa$_6$, Xaa$_7$, Xaa$_8$, Xaa$_9$ . . . , crosslinks between Xaa$_1$ and Xaa$_4$, or between Xaa$_1$ and Xaa$_5$, or between Xaa$_1$ and Xaa$_8$ are useful as are crosslinks between Xaa$_2$ and Xaa$_5$, or between Xaa$_2$ and Xaa$_6$, or between Xaa$_2$ and Xaa$_9$, etc. In addition, a model polypeptide was prepared incorporating two sets of crosslinks with one located between Xaa$_1$ and Xaa$_5$ and another between Xaa$_9$ and Xaa$_{13}$. The double crosslink was achieved by careful stereochemical control of the double bond metathesis reactions. Thus, the invention encompasses the incorporation of more than one crosslink within the polypeptide sequence to either further stabilize the sequence or facilitate the stabilization of longer polypeptide stretches. If the polypeptides are too long to be readily synthesized in one part, independently synthesized crosslinked peptides can be conjoined by a technique called native chemical ligation (Bang, et al., *J. Am. Chem. Soc.* 126:1377).

The novel cross-linked polypeptides are useful, for example, to mimic or study proteins or polypeptides having one or more alpha-helical domains. One family of proteins where family members have at least one alpha helical domain is the BCL-2 family of proteins. These proteins are involved in cellular apoptotic pathways. Some BCL-2 family members have a pro-apoptotic function, others have an anti-apoptotic function, and still others change functions with a change in cellular conditions. Accordingly, it is desirable to make stabilized polypeptides that would mimic one or more motifs of the BCL-2 family members, thus modulating a variety of BCL-2 related activities.

Figure 1:
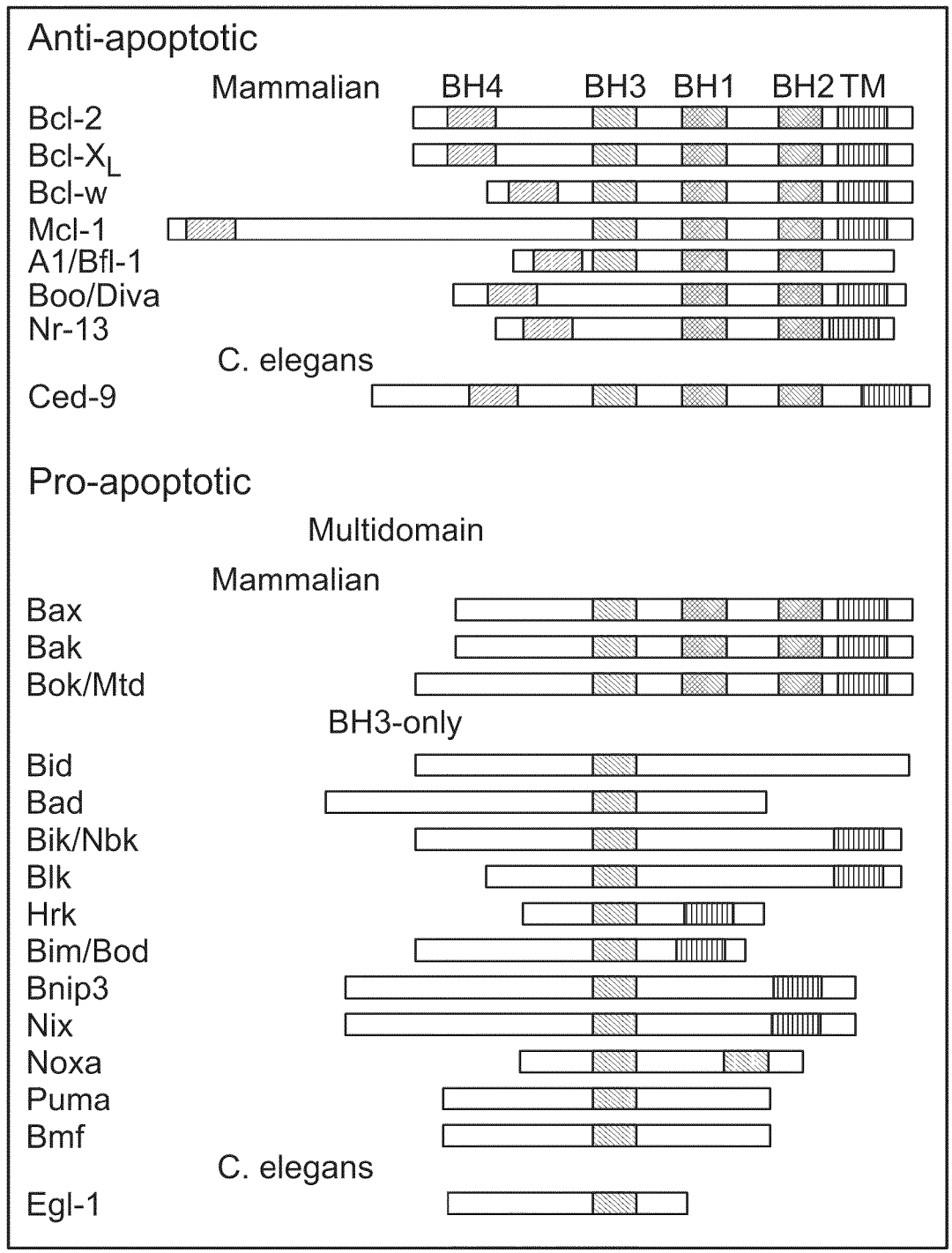
FIG. 1 depicts BCL-2 family members having one or more conserved BCL-2 homology (BH) domains.
Figure 2:
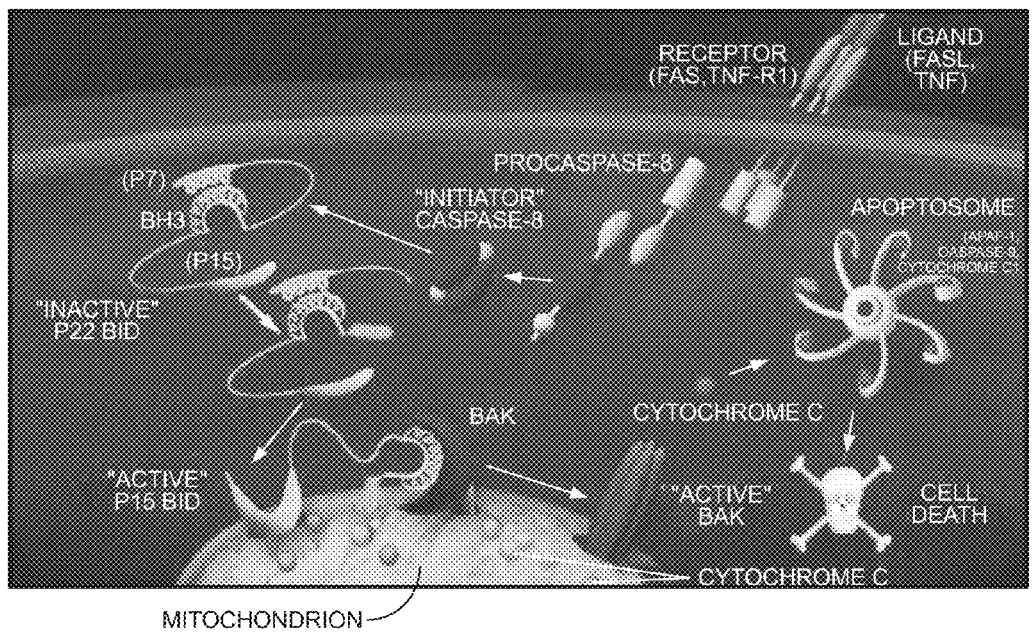
FIG. 2 depicts a model of BID-mediated mitochondrial apoptosis. TNF-RI/Fas induces cleavage of BID, which translocates to the mitochondria and trigger apoptosis.
Figure 3:
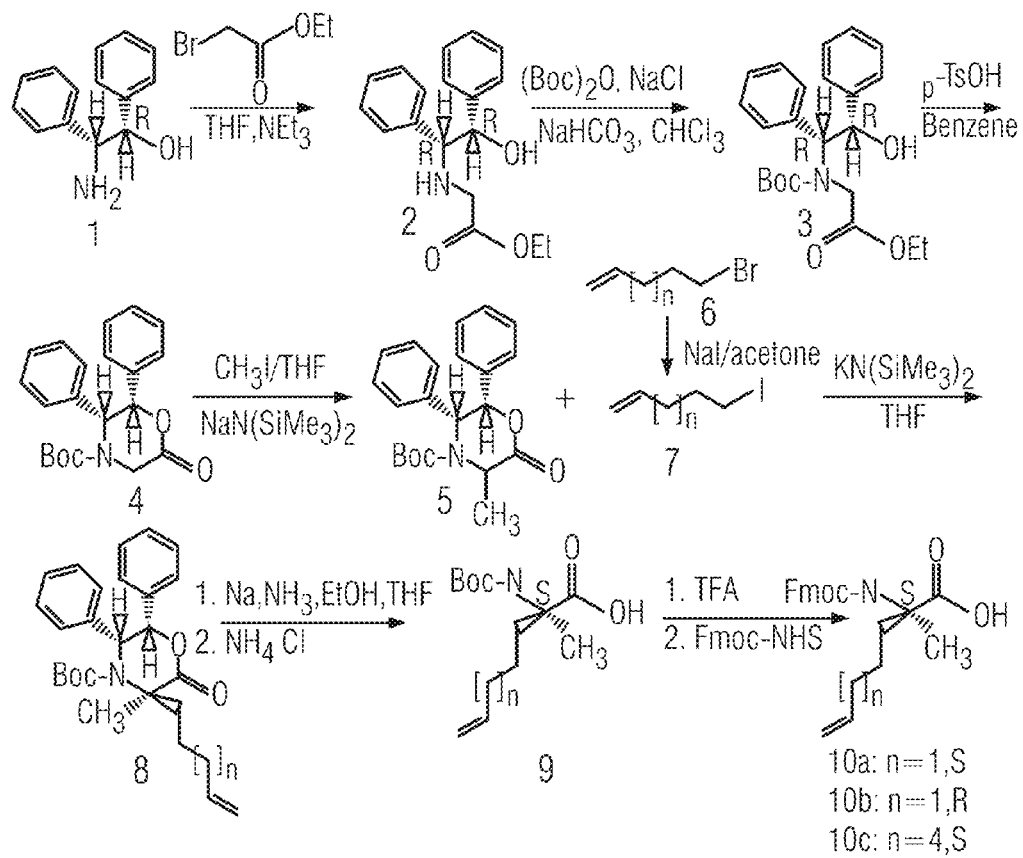
FIG. 3 depicts a synthetic strategy for the generation of chiral α,α-disubstituted non-natural amino acids containing olefinic side chains.

Chemical Synthesis of a Panel of SAHB3$_{BID}$ Compounds

α,α-Disubstituted non-natural amino acids containing olefinic side chains of varying length were synthesized according to the schema in FIG. 3 (Williams et al. 1991 *J. Am. Chem. Soc.* 113:9276; Schafmeister et al. 2000 J. Am. Chem. Soc. 122:5891). Chemically crosslinked BID BH3 peptides were designed by replacing two or four naturally occurring amino acids with the corresponding synthetic amino acids (FIG. 4a). Substitutions were made at discrete locations, namely the "i, and i+4 positions" or the "i, and i+7 positions", which facilitate crosslinking chemistry by placing reactive residues on the same face of the α-helix (FIG. 4b). Highly conserved amino acids among apoptotic proteins, in addition to those sequences found to be important in protein-protein interactions based on X-ray crystallographic and NMR studies (Muchmore et al. 1996 *Nature* 381:335; Sattler et al. 1997 *Science* 275:983), were specifically not replaced in certain circimstances, conserved amino acids could be replaced by other amino acids (e.g., synthetic non-naturally occurring amino acids) to enhance activity (this effect can be seen in the SAHB3$_{BID}$ mutants described herein). SAHB3$_{BID}$ compounds were generated by solid phase peptide synthesis followed by olefin metathesis-based crosslinking of the synthetic amino acids via their olefin-containing side chains. The variations of SAHB3$_{BID}$ compounds generated are illustrated in FIG. 5a. SAHB3$_{BID}$ (SAHB$_A$) variants incorporating specific mutations known to alter BID function (Wang et al. 1996 *Genes Dev.* 10:2859) were also constructed to serve as negative controls in biological experiments (FIG. 5a). The amino termini of selected compounds were further derivatized with fluorescein isothiocyanate (FITC) or biotin conjugated-lysine to generate labeled SAHB3$_{BID}$ compounds for cell permeability studies and biochemical assays, respectively (FIG. 5a). In several syntheses, a C-terminal tryptophan was added to the sequence to serve as a UV label for purification and concentration determination purposes; the N-terminal glutamic acid was eliminated in several peptides in order to increase the overall pI of the compound to potentially facilitate cell penetration (see below). The metathesis approach was readily applied to the generation of alternate SAHB3s, including SAHB3$_{BAD}$ and SAHB3$_{BIM}$ (FIG. 5a).

The non-natural amino acids (R and S enantiomers of the 5-carbon olefinic amino acid and the S enantiomer of the 8-carbon olefinic amino acid) were characterized by nuclear magnetic resonance (NMR) spectroscopy (Varian Mercury 400) and mass spectrometry (Micromass LCT). Peptide synthesis was performed either manually or on an automated peptide synthesizer (Applied Biosystems, model 433A), using solid phase conditions, rink amide AM resin (Novabiochem), and Fmoc main-chain protecting group chemistry. For the coupling of natural Fmoc-protected amino acids (Novabiochem), 10 equivalents of amino acid and a 1:1:2 molar ratio of coupling reagents HBTU/HOBt (Novabiochem)/DIEA were employed. Non-natural amino acids (4 equiv) were coupled with a 1:1:2 molar ratio of HATU (Applied Biosystems)/HOBt/DIEA. Olefin metathesis was performed in the solid phase using 10 mM Grubbs catalyst (Blackewell et al. 1994 supra) (Strem Chemicals) dissolved in degassed dichloromethane and reacted for 2 hours at room temperature. The amino termini of selected compounds were further derivatized with b-alanine and fluorescein isothiocyanate (FITC [Sigma]/DMF/DIEA) to generate fluorescently labeled compounds. A C-terminal tryptophan was incorporated to serve as a UV label for purification and concentration determination purposes; SAHBA compounds were also synthesized without the C-terminal tryptophan and N-terminal glutamic acid, the latter modification performed to increase the overall pI of the molecules. Isolation of metathesized compounds was achieved by trifluoroacetic acid-mediated deprotection and cleavage, ether precipitation to yield the crude product, and high performance liquid chromatography (HPLC) (Varian ProStar) on a reverse phase C18 column (Varian) to yield the pure compounds. Chemical composition of the pure products was confirmed by LC/MS mass spectrometry (Micromass LCT interfaced with Agilent 1100 HPLC system) and amino acid analysis (Applied Biosystems, model 420A).

Figures 5B, 6A:
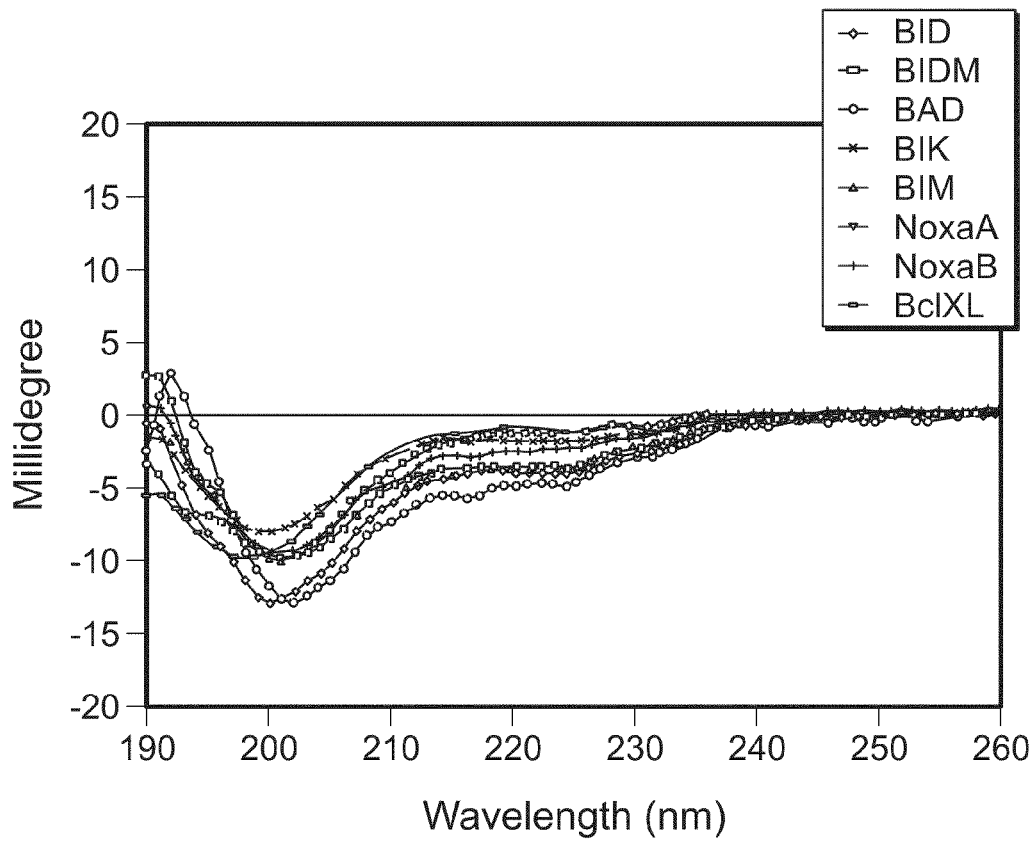
FIG. 5b depicts certain crosslinked peptides used in the studies described herein (SEQ ID NOs 112-117, respectively).

FIG. 5b schematically depicts a subset of the peptides in FIG. 5a, including the stereochemistry of the olefinic amino acids (R and S enantiomers of the 5-carbon olefinic amino acid and the S enantiomer of the 8-carbon olefinic amino acid).

SAHB3$_{BID}$ Compounds Display Enhanced α-Helicity

Figure 6B:
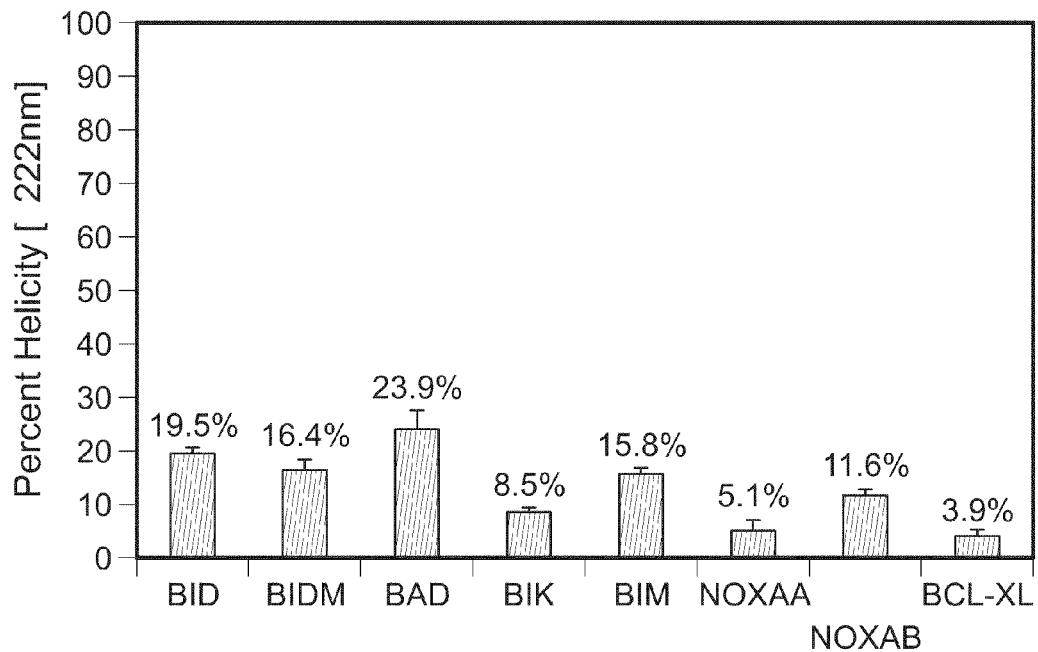
FIG. 6 depicts the results of a study showing the degree of α-helicity of BH3 domains of selected BCL-2 family members.

We examined the percent helicity of pro-apoptotic BH3 domains, and found that these unmodified peptides were predominantly random coils in solution, with α-helical content all under 25% (FIG. 6). Briefly, compounds were dissolved in aqueous 50 mM potassium phosphate solution pH 7 to concentrations of 25-50 mM. CD spectra were obtained on a Jasco J-710 spectropolarimeter at 20° C. using the following standard measurement parameters: wavelength, 190-260 nm; step resolution, 0.5 nm; speed, 20 nm/sec; accumulations, 10; response, 1 sec; bandwidth, 1 nm; path length, 0.1 cm. The α-helical content of each peptide was calculated by dividing the mean residue ellipticity [φ]222obs by the reported [φ]222obs for a model helical decapeptide (Yang et al. 1986 *Methods Enzymol.* 130:208)).

Figure 7A:
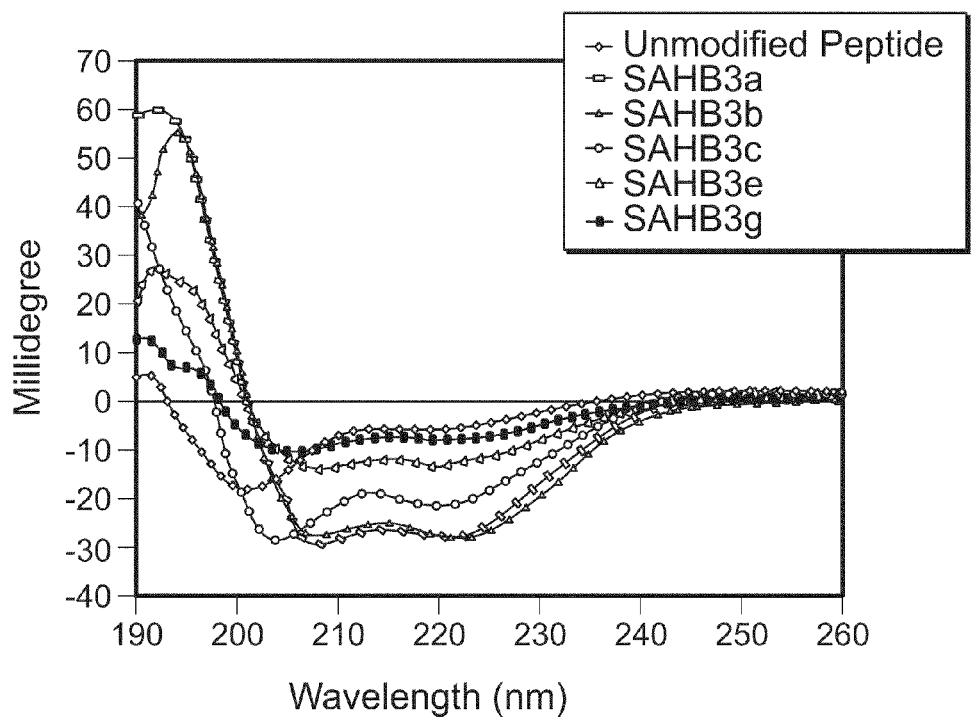
FIG. 7 depicts the results of a study showing that chemical crosslinking enhances the alpha helicity of SAHB3$_{BID}$ compounds compared to the unmodified BID BH3 peptide.
Figure 7B:
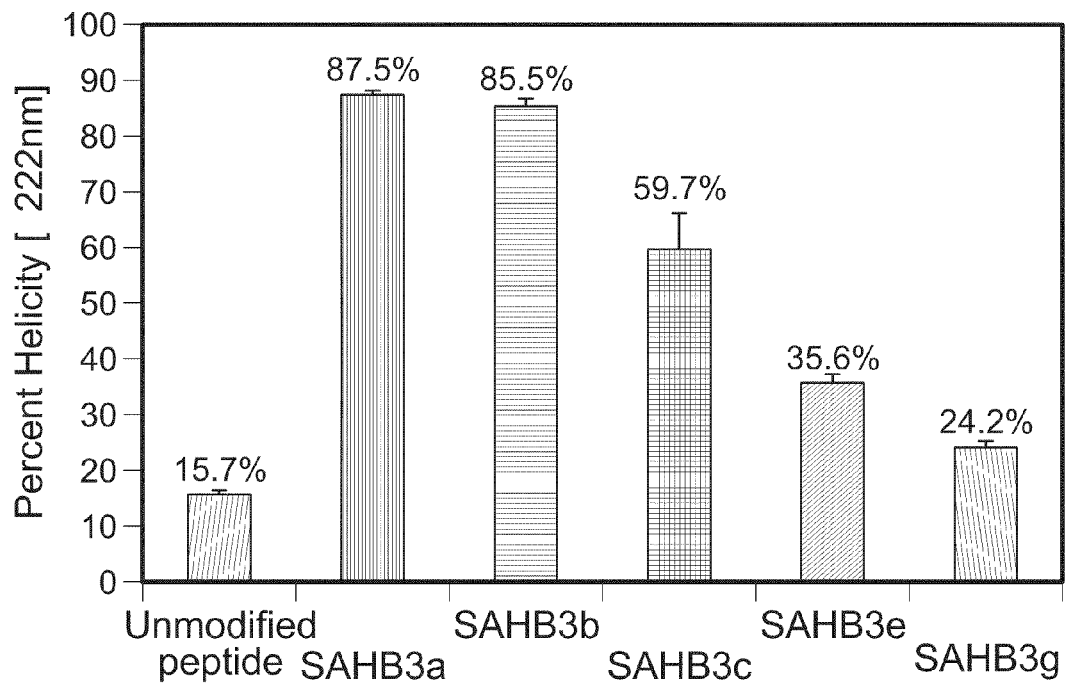
Figure 8A:
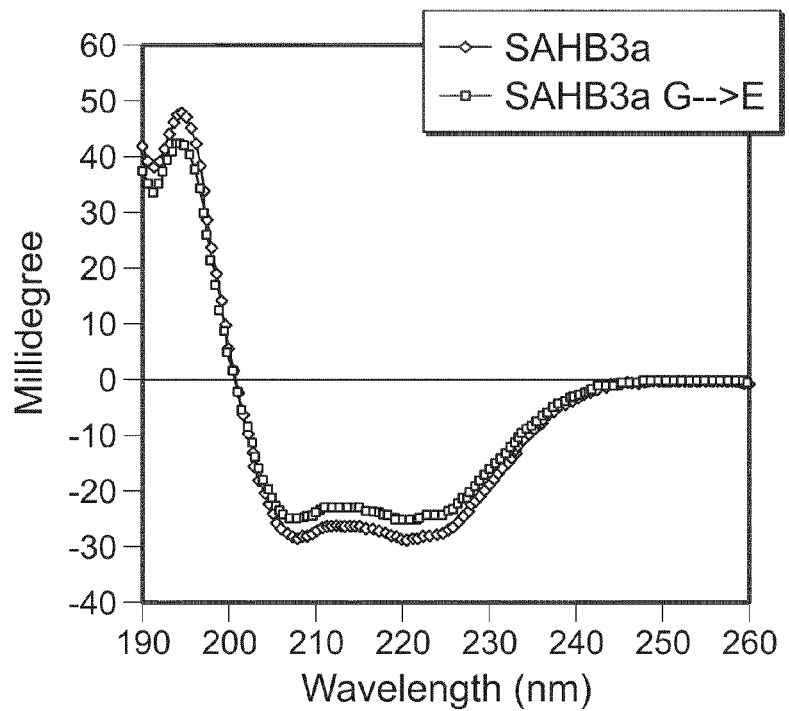
FIG. 8 depicts the results of a study showing that a gly→glu mutant of SAHB3$_{BID}$A polypeptide displays similar helical contact to the corresponding gly containing polypeptide.
Figure 8B:
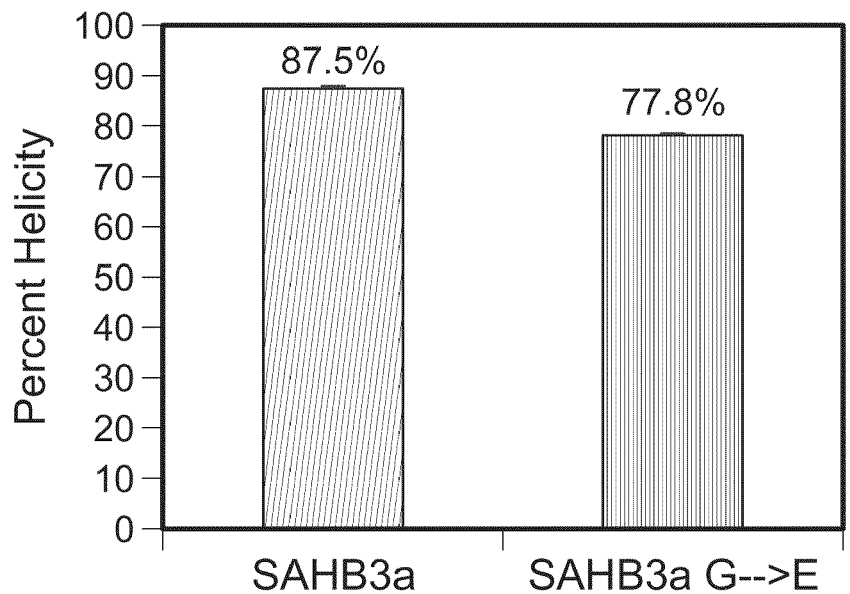
Figure 9:
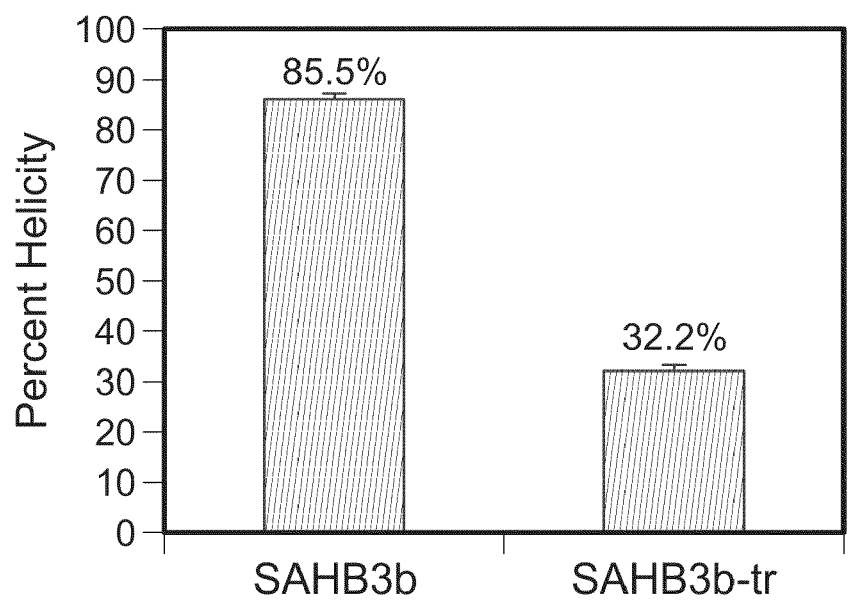
FIG. 9 depicts the results of a study showing that truncation of the 23-mer SABH3$_{BID}$B ("SAHB3b") to a 16-mer results in loss of α-helicity.

In each case, the chemical crosslink(s) increased the percent α-helicity of BID's BH3 domain, with SAHB3$_{BID}$A and B achieving more than 5-fold enhancement (FIG. 7). SAHB3$_{BID(G \rightarrow E)}$A, a negative control Gly to Glu point mutant of SAHB3$_{BID}$A, displays similar helical content to SAHB3$_{BID}$A (FIG. 8). Thus, the all-hydrocarbon crosslink can transform an apoptotic peptide that is essentially a random coil in aqueous solution into one that is predominantly α-helical in structure. Interestingly, the importance of the fourth helical turn in stabilizing BID BH3 peptides is underscored by the decrease in helicity observed when the SAHB3$_{BID}$B 23-mer is truncated to the 16-mer, SAHB3$_{BID(tr)}$B (FIG. 9).

Figure 10A:
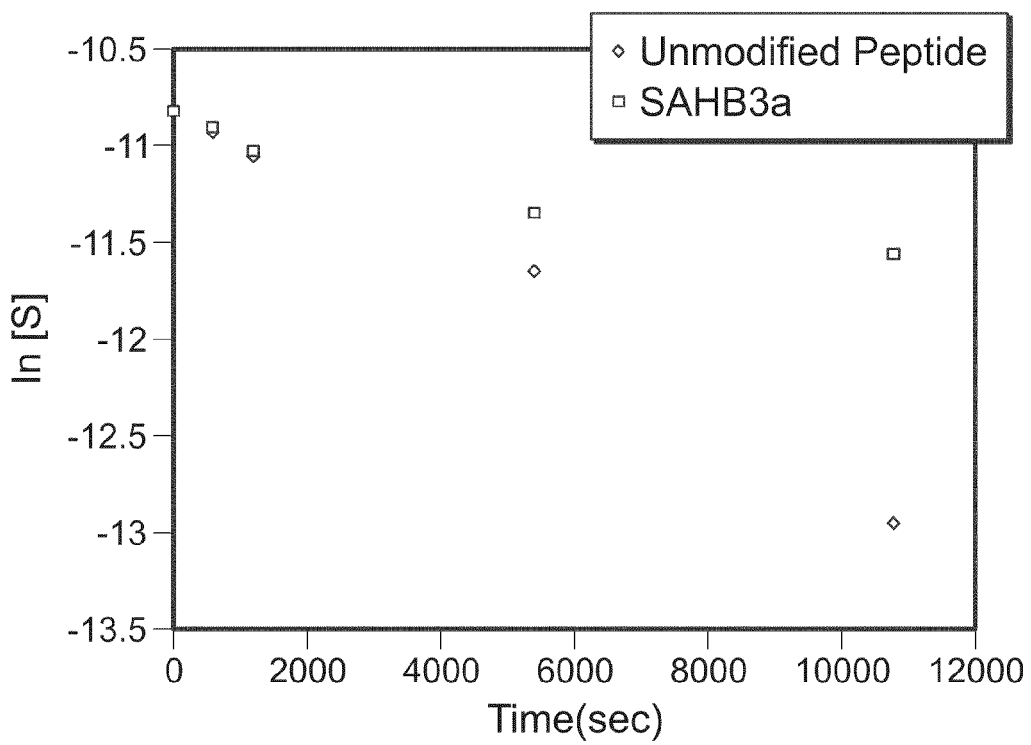
FIG. 10a depicts the results of a study showing that the kinetics of in vitro trypsin proteolysis is retarded 3.5-fold by the SABH3$_{BID}$A crosslink.

The All-Hydrocarbon Crosslink Increases Protease Resistance of SAHB3$_{BID}$ Compounds The amide bond of the peptide backbone is susceptible to hydrolysis by proteases, thereby rendering peptidic compounds vulnerable to rapid degradation in vivo. Peptide helix formation, however, buries the amide backbone and therefore shields it from proteolytic cleavage. SAHB3$_{BID}$A was subjected to in vitro trypsin proteolysis to assess for any change in degradation rate compared to the unmodified BID BH3 peptide. SAHB3$_{BID}$A and unmodified peptide were incubated with trypsin agarose and the reactions quenched at various time points by centrifugation and subsequent HPLC injection to quantitate the residual substrate by ultraviolet absorption at 280 nm. Briefly, BID BH3 and SAHB3$_{BID}$A compounds (5 mcg) were incubated with trypsin agarose (Pierce) (S/E~125) for 0, 10, 20, 90, and 180 minutes. Reactions were quenched by tabletop centrifugation at high speed; remaining substrate in the isolated supernatant was quantified by HPLC-based peak detection at 220 nm. The proteolytic reaction displayed first order kinetics and the rate constant, k, determined from a plot of ln [S] versus time (k=−1×slope) (FIG. 10a). The experiment, performed in triplicate, demonstrated a 3.5-fold enhancement in trypsin resistance of SAHB3$_{BID}$A compared to the unmodified peptide. Thus, enhanced protection of trypsin-sensitive amide bonds by burying them at the core of the α-helix affords a more stable peptidic compound, and may therefore render such compounds particularly stable in serum.

Figure 10B:
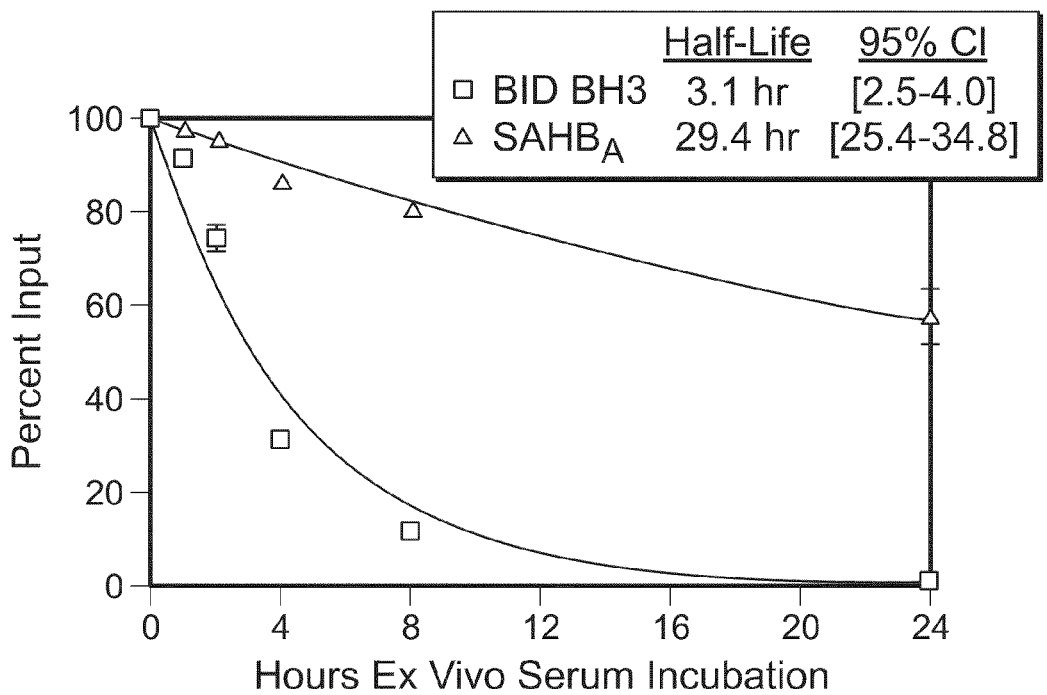
FIG. 10b depicts the results of a study of ex vivo serum stability of peptides, demonstrating a 10-fold increase in half-life of the cross-linked peptide compared to the unmodified peptide.

For ex vivo serum stability studies, FITC-conjugated peptides BID BH3 and SAHB3$_{BID}$A (2.5 mcg) were incubated with fresh mouse serum (20 mL) at 37° C. for 0, 1, 2, 4, 8, and 24 hours. The level of intact FITC-compound was determined by flash freezing the serum specimens in liquid nitrogen, lyophilization, extraction in 50:50 acetonitrile/water containing 0.1% trifluoroacetic acid, followed by HPLC-based quantitation using fluorescence detection at excitation/emission settings of 495/530 nm. The results of this analysis are shown in FIG. 10b.

Figure 10C:
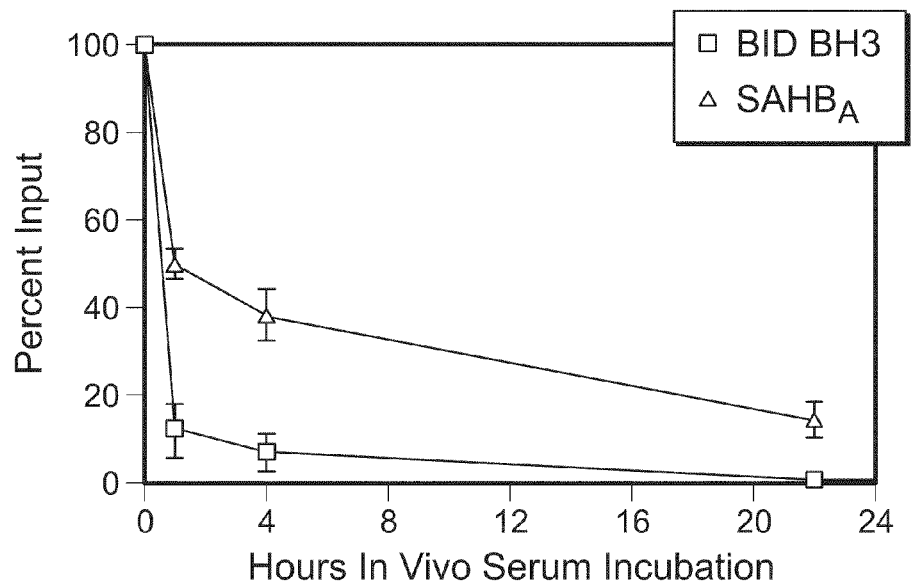
FIG. 10c depicts the results of an in vivo study showing that SAHB3$_{BID}$A is maintained at higher serum concentrations over time compared to BID BH3 peptide.

To investigate the in vivo stability of SAHB3$_{BID}$A, 10 mg/kg of FITC-conjugated BID BH3 peptide and SAHB3$_{BID}$A were injected into NOD-SCID mice and blood specimens withdrawn at 0, 1, 4 and 22 hours post-injection. Levels of intact FITC-compound in 25 μL of fresh serum were then measured. The results of this analysis, depicted in FIG. 10c, show that SAHB3$_{BID}$A was readily detectable over a 22 hour period, with 13% of the input still measurable a 22 hours. In contrast, only 12% of BID BH3 was detectable one hour after injection.

SAHB3$_{BID}$ Compounds Retain High Affinity Anti-Apoptotic Binding

Figure 11A:
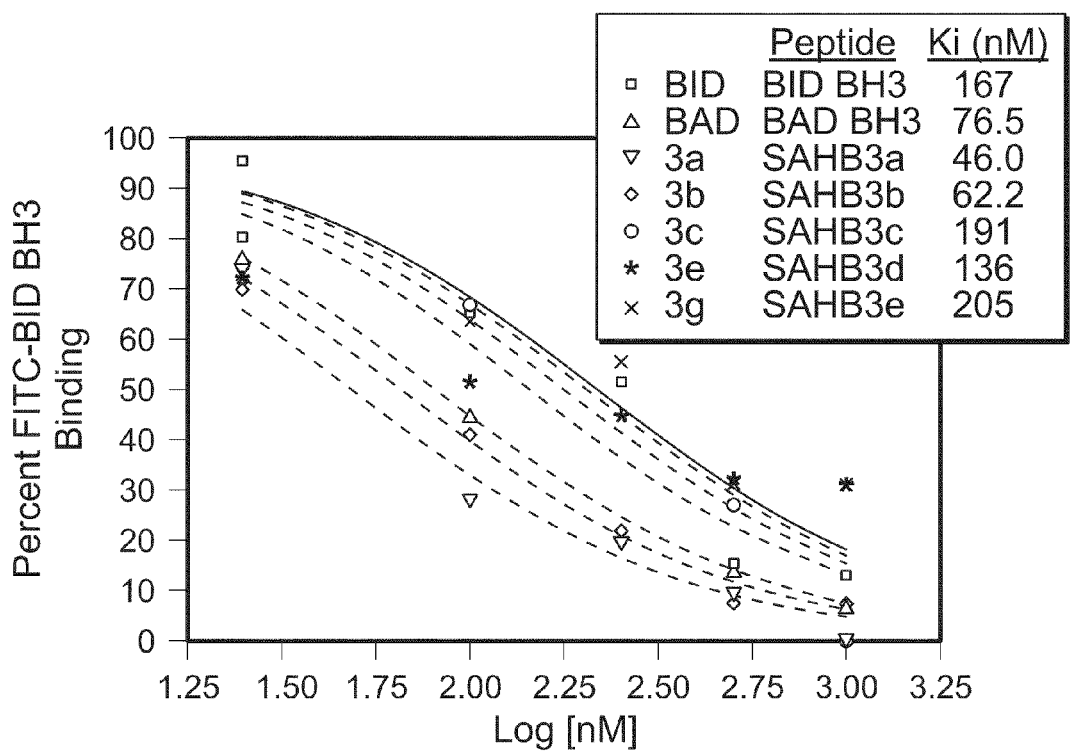
FIG. 11a depicts the results of a study showing that SAHB3 BID peptides display high affinity binding to GST-BCL2 in a fluorescence polarization competitive binding assay.
Figure 11B:
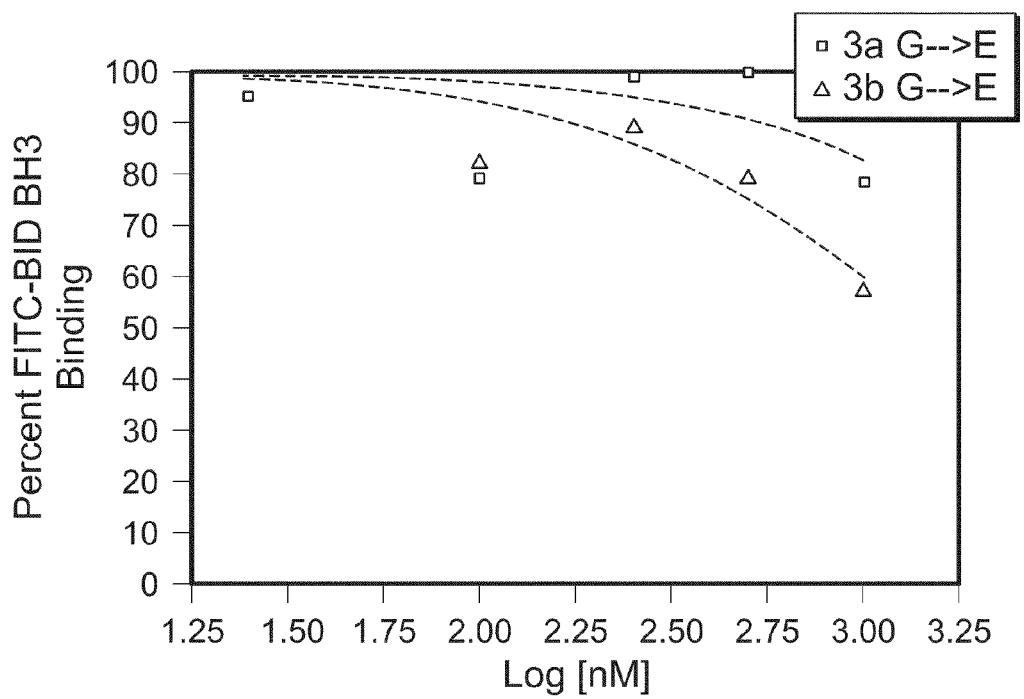
FIG. 11b depicts the results of a study showing that the negative control Gly to Glu point mutants of SAHB3$_{BID}$A and B are relatively poor binders.
Figure 11C:
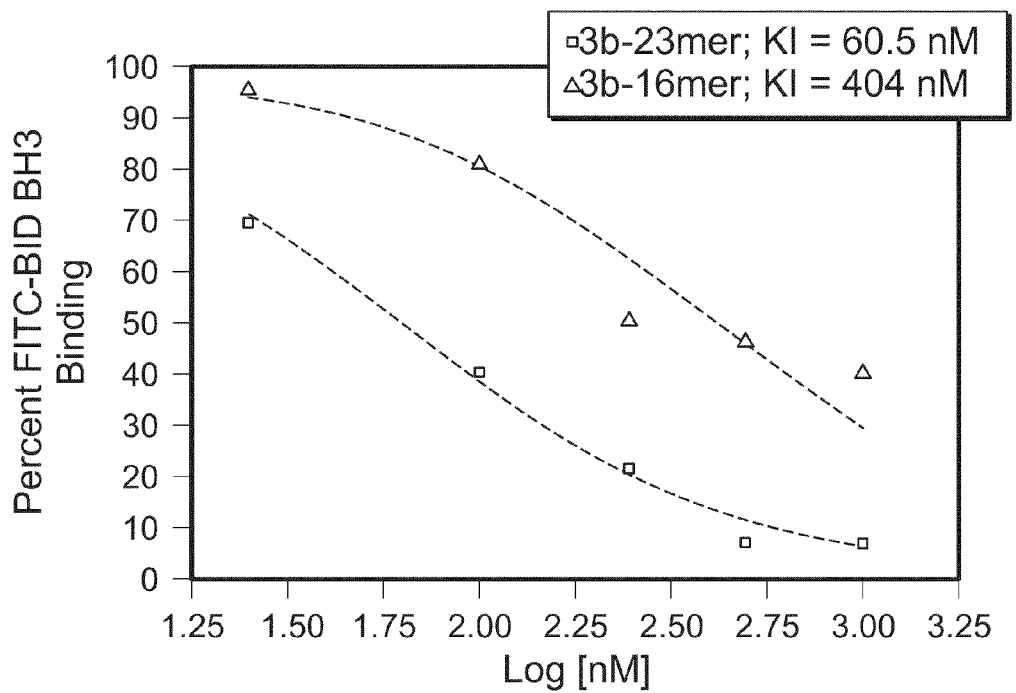
FIG. 11c depicts the results of a study showing that truncation of SAHB3$_{BID}$B from a 23-mer to a 16-mer results in a more than 6-fold drop in $K_i$, coincident with a significant decrease in percent helicity of the truncated compound.

The all-hydrocarbon crosslinks were selectively placed on the charged face of the BID BH3 amphipathic helix in order to avoid interference with critical interactions between the binding pocket of multidomain apoptotic proteins and the hydrophobic residues of the BID BH3 helix. Fluorescence polarization competitive binding experiments were performed to evaluate the efficacy of SAHB3$_{BID}$ compounds in competing with FITC-labeled unmodified BID BH3 peptide for GST-BCL-2 binding. All SAHB3$_{BID}$ compounds demonstrate high affinity binding to GST-BCL2, with SAHB3$_{BID}$A and B, the two compounds with the greatest percent helicity, likewise displaying the highest affinity binding (FIG. 11a). Of note, Gly to Glu mutation of SAHB3$_{BID}$A and B eliminates high affinity binding, as would be predicted from previous studies (FIG. 11b). We additionally determined that Gly to Ser mutation of SAHB3$_{BID}$A abolishes BCL-2 binding in this assay (data not shown). Truncation of the 23-mer SAHB3$_{BID}$B to a 16-mer results in loss of BCL-2 binding affinity, coincident with the decrement in α-helicity described above (FIG. 11c).

FITC-labeled BID BH3 peptide binds to BCL-2 with a K$_D$ of 220 nM, and once bound, displacement of this interaction by unlabeled BID BH3 occurs at an IC$_{50}$ of 838 nM. This supports a model whereby BH3 binding to BCL-2 triggers an overall conformational change favoring the interaction, resulting in the need for excess amounts of unlabeled peptide to displace prebound FITC-labeled BID BH3. We have further shown that the BAD BH3 domain has an enhanced K$_D$ of 41 nM for BCL-2 binding, and that it can displace prebound FITC-BID BH3 with an IC$_{50}$ of 173 nM. In a similar experiment, SAHB3$_{BID}$A was found to displace FITC-BID BH3 from BCL-2 with an IC$_{50}$ of 62 nM, reflecting a more than 13-fold increase in displacement potency compared to unmodified BID BH3 peptide. These data confirm that SAHB3$_{BID}$A binds with enhanced affinity to BCL-2 compared to unmodified BH3 peptides, and suggest that preorganization of α-helical structure by chemical crosslinking provides a kinetic advantage for target binding.

Figure 11D:
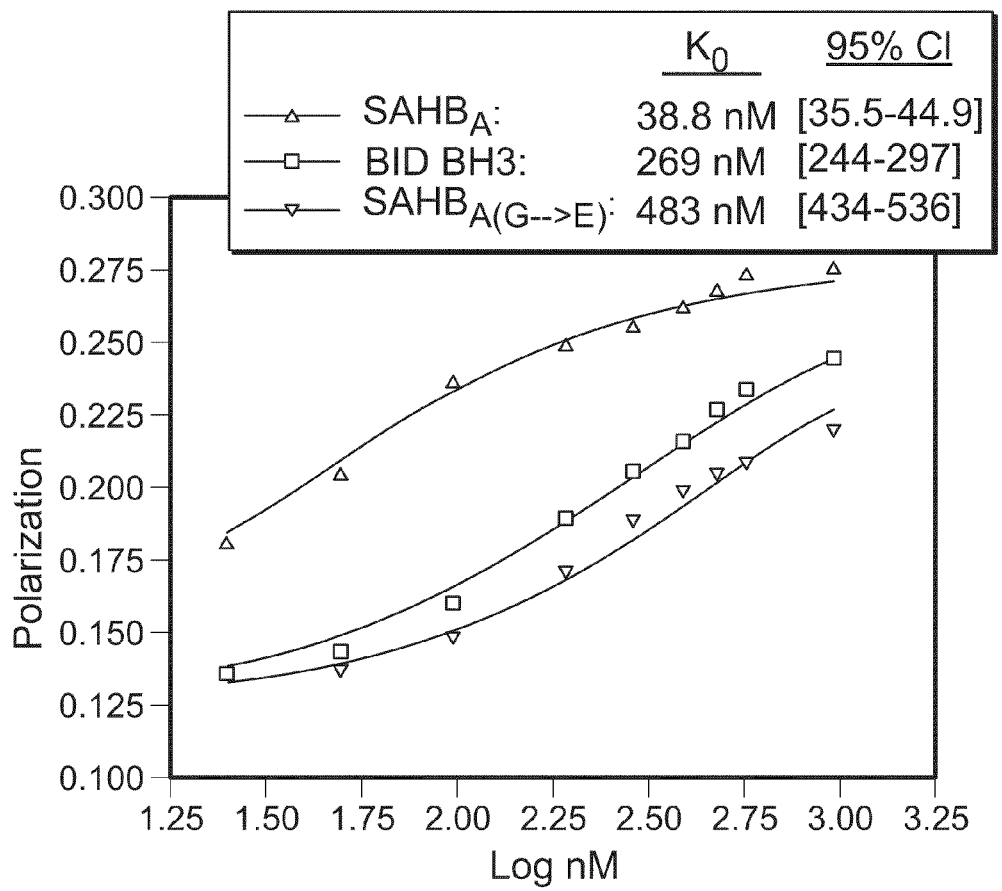
FIG. 11d depicts the results of a BCL-2 fluorescence polarization direct binding assay demonstrating a more than 6-fold enhancement in binding affinity of SAHB3$_{BID}$A compared to unmodified BID BH3.
Figure 11E:
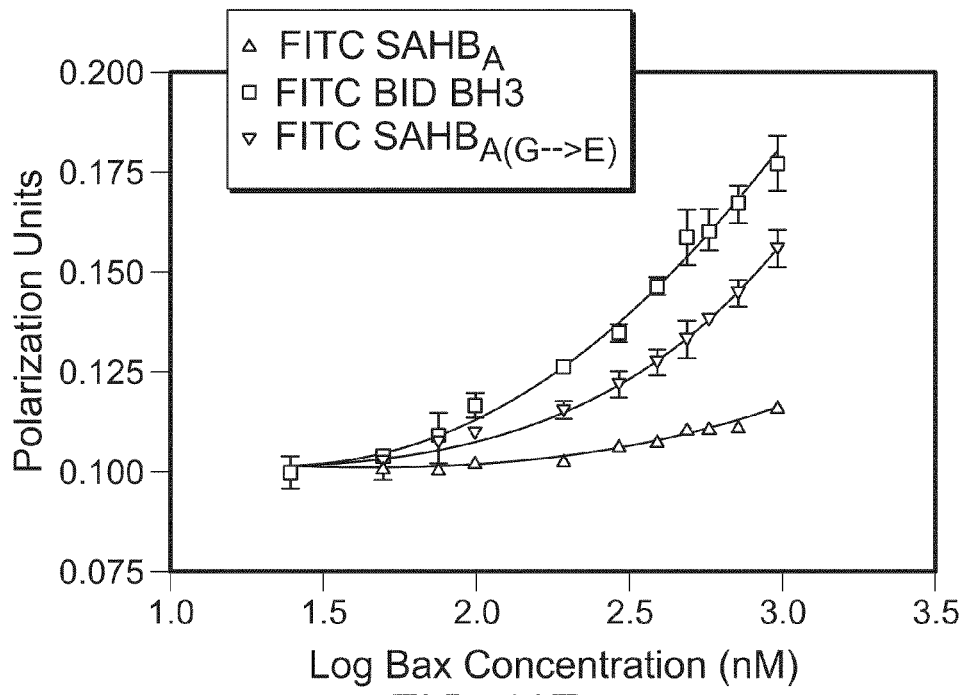
FIG. 11e depicts the results of a BAX fluorescence polarization direct binding assay demonstrating that incorporation of a crosslink results in measurable binding of SAHB3$_{BID}$A and SAHB3$_{BID(G \to E)}$A to a multidomain pro-apoptotic BCL-2 family member. The unmodified BID BH3 peptide shows no binding.

Direct binding assays by fluorescence polarization demonstrated that incorporation of the crosslink into BID BH3 peptide resulted in enhanced binding affinity of SAHB3$_{BID}$A for both BCL-2, an anti-apoptotic multidomain protein, and BAX, a pro-apoptotic multidomain protein, compared to unmodified BID BH3 peptide (FIGS. 11d and 11e). A direct BCL-2 fluorescence polarization binding assay demonstrated a 6-fold enhancement in BCL-2 binding affinity of SAHB3$_{BID}$A (K$_D$, 38.8 nm) compared to unmodified BID BH3 peptide (K$_D$, 269 nM) (FIG. 11d). A Gly to Glu mutation, SAHB$_{A(G \rightarrow E)}$ (K$_D$, 483 nM), eliminates high affinity binding and serves as a useful control (FIG. 11d). Briefly, *Escherichia coli* BL21 (DE3) containing the plasmid encoding C-terminal deleted GST-BCL-2 were cultured in ampicillin-containing Luria Broth and induced with 0.1 mM IPTG. The bacterial pellets were resuspended in lysis buffer (1 mg/ml lysozyme, 1% Triton X-100, 0.1 mg/ml PMSF, 2 µg/ml aprotinin, 2 µg/ml leupeptine, 1 µg/ml pepstatin A in PBS) and sonicated. After centrifugation at 20,000×g for 20 min, the supernatant was applied to a column of glutathione-agarose beads (Sigma). The beads were washed with PBS and treated with 50 mM glutathione, 50 mM Tris-HCl (pH 8.0) to elute the protein, which was then dialyzed against binding assay buffer (140 mM NaCl, 50 mM Tris-HCl [pH 7.4]). Fluorescinated compounds (25 nM) were incubated with GST-BCL2 (25 nM-1000 nM) in binding buffer at room temperature. Binding activity was measured by fluorescence polarization on a Perkin-Elmer LS50B luminescence spectrophotometer. KD values were determined by nonlinear regression analysis using Prism software (Graphpad). Full-length BAX protein was prepared as previously described (Suzuki et al, *Cell*, 103:645) and fluorescence polarization assay performed as described above.

SAHB3$_{BID}$A Binds to BCL-X$_L$

To determine if SAHB3$_{BID}$A specifically interacts with the defined binding groove of an anti-apoptotic multidomain protein, a two-dimensional $^{15}$N/$^1$H heteronuclear single-quantum correlation (HSQC) spectrum of $^{15}$N-labeled BCL-X$_L$ before and after the addition of SAHB3$_{BID}$A was recorded and compared with the corresponding BID BH3/$^{15}$N-BCL-X$_L$ spectrum. Briefly, *Escherichia coli* BL21 (DE3) containing the plasmid encoding C-terminal deleted BCL-X$_L$ were cultured in M9-minimal medium containing $^{15}$NH$_4$Cl (Cambridge Isotope Laboratories) to generate uniformly $^{15}$N-labeled protein. Recombinant proteins were isolated from bacteria. Unlabeled SAHB3$_{BID}$A and BID BH3 peptides were generated and purified as described above. The following 1:1 complexes were prepared at 0.1 mM in 50 mM potassium phosphate (pH 7), 50 mM sodium chloride, 5% DMSO in D$_2$O or H$_2$O/D$_2$O (95:5): $^{15}$N-BCL-X$_L$/unlabeled BID BH3, $^{15}$N-BCL-X$_L$/unlabeled SAHB3$_{BID}$A. Two dimensional $^{15}$N/$^1$H heteronuclear single-quantum spectra were recorded for the two complexes and analyzed for changes in resonance upon ligand binding.

Figure 11F:
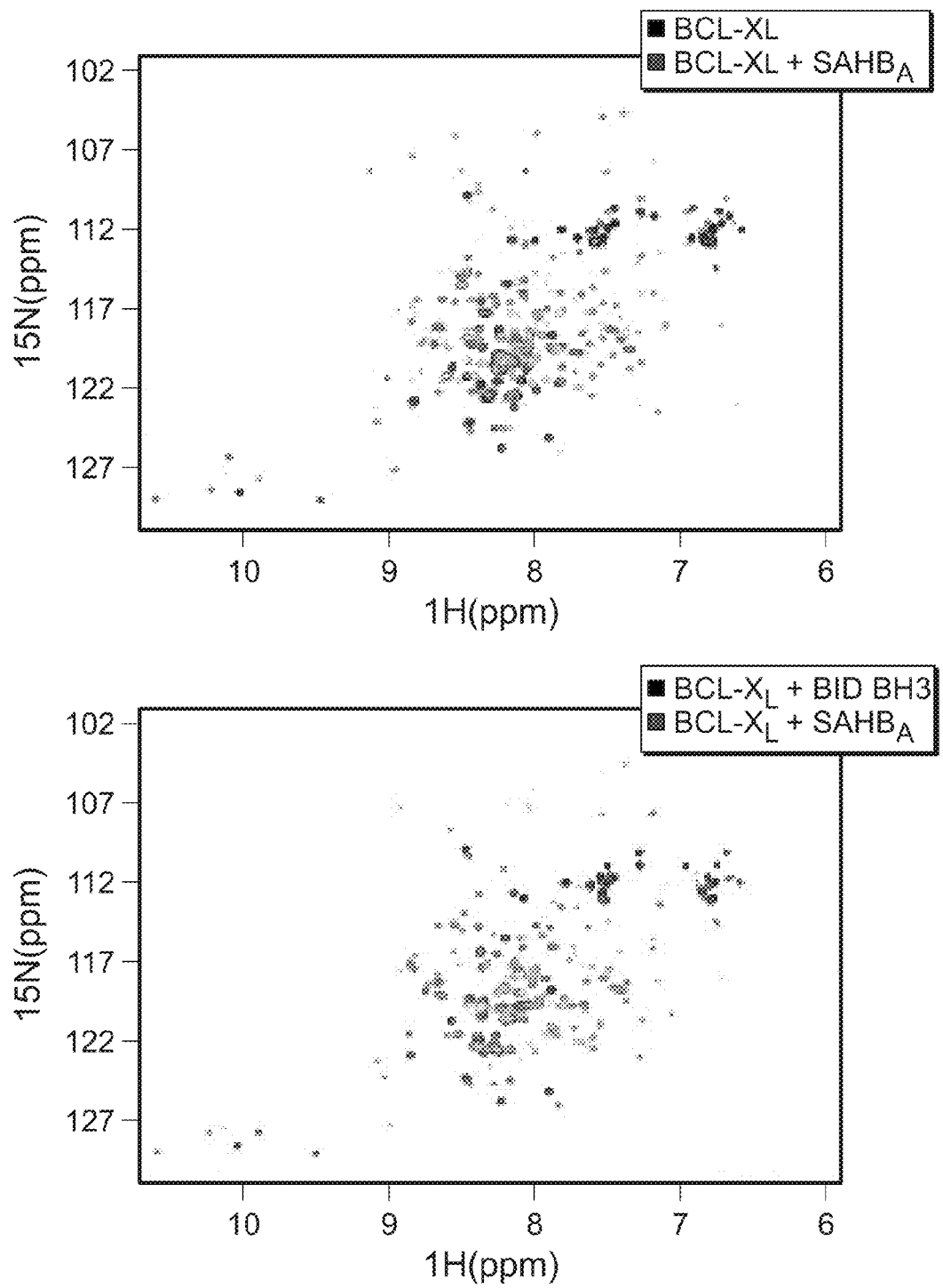
FIG. 11f depicts HSQC spectra that demonstrate a conformational change in $^{15}$N-labeled BCL-X$_L$ upon SAHB3$_{BID}$A binding, which is similar to that seen upon BID BH3 binding, confirming that SAHB3$_{BID}$A binds to the defined hydrophobic pocket of BCL-X$_L$.

The overall similarity of the HSQC spectra indicates that the structural changes occurring in BCL-X$_L$ after addition of SAHB3$_{BID}$A are nearly identical to those observed with BID BH3 peptide (FIG. 11f).

Figure 12A:
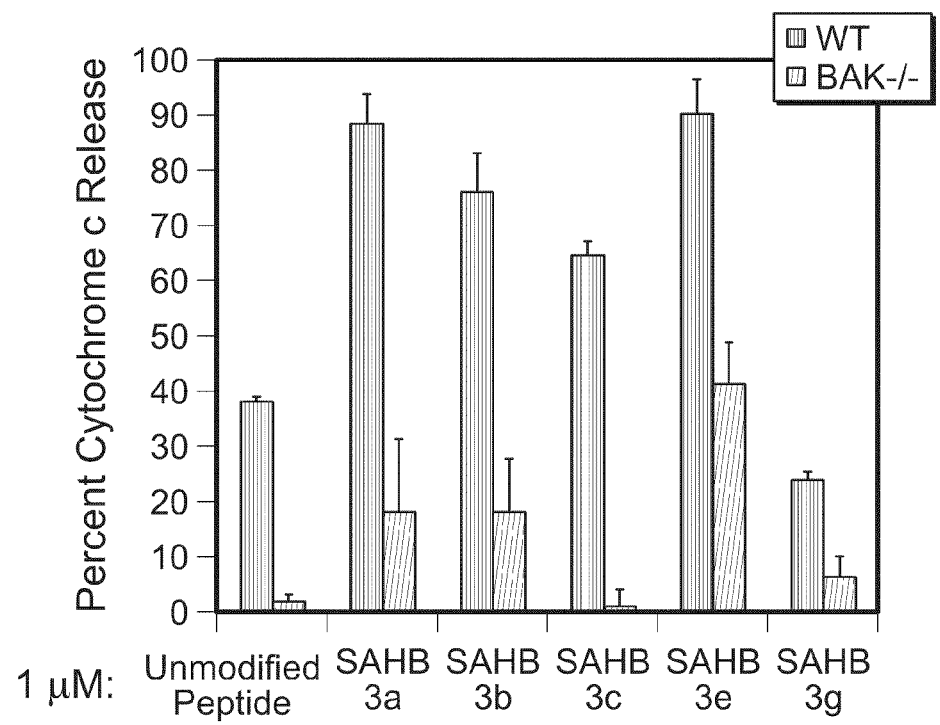
FIGS. 12a and 12b depict the results of studies showing the percent of cytochrome c released by SAHB3$_{BID}$ compounds from purified mouse liver mitochondria.
Figure 12B:
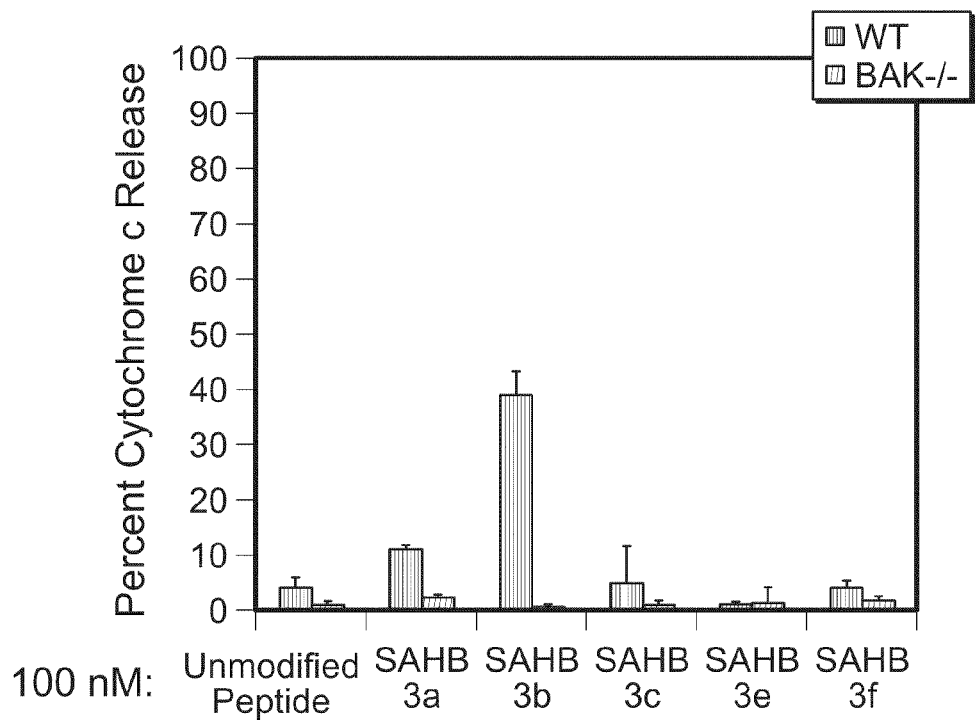

SAHB3BID Compounds Trigger Rapid and Specific Release of Mitochondrial Cytochrome C In order to assess the biological activity of SAHB3$_{BID}$ compounds in vitro, cytochrome c release assays were performed using purified mouse liver mitochondria. Mitochondria (0.5 mg/mL) were incubated for 40 minutes with 1 µM and 100 nM of SAHB3$_{BID}$ compounds and then supernatants and mitochondrial fractions isolated and subjected to cytochrome c ELISA assay. Background cytochrome c release (10-15%) was subtracted from total release for each sample, and the percent actual cytochrome c release was determined (FIG. 12). The identical experiment was performed concurrently on mouse liver mitochondria isolated from Bak−/− mice, which do not release mitochondrial cytochrome c in response to BID-BH3 activation; data from the BAK−/− mitochondria therefore serve as a negative control for BAK-mediated cytochrome c release in response to SAHB3$_{BID}$ treatments. In each case, except for the double cross-linked SAHB3$_{BID}$E (which may lack critical amino acids for biological activity or, in this case, be overly constrained by the dual cross-links), there is approximately a doubling of cytochrome c release in response to 1 µM SAHB3$_{BID}$ compounds compared to the unmodified peptide (FIG. 12a). BAK-independent cytochrome c release is observed at this dose with SAHB3$_{BID}$A, B, and, in particular, D. Whereas this cytochrome c release may represent a nonspecific membrane perturbing effect of the α-helices, the role of a SAHB3$_{BID}$-induced, BAK-independent component of cytochrome c release is worthy of further exploration. Interestingly, the SAHB3$_{BID}$ compound that induces the most significant level of BAK-independent cytochrome c release, SAHB3$_{BID}$D, is also the most hydrophobic of the SAHB3$_{BID}$ compounds; SAHB3$_{BID}$D elutes from the reverse phase C18 column at 95% acetonitrile/5% water, compared to the other SAHB3$_{BID}$ compounds that elute at 50-75% acetonitrile. BID mutants with defective BH3 domains can promote BAK-independent cytochrome c mobilization (Scorrano et al, *Dev Cell*, 2:55), and the highly hydrophobic BID helix 6 has been implicated in this activity (L. Scorrano, S. J. Korsmeyer, unpublished results). It is plausible that SAHB3$_{BID}$D displays both BAK dependent and independent cytochrome c release by mimicking features of BID helices 3 and 6. At ten-fold lower dosing SAHB3$_{BID}$A and B retain selective BAK-dependent cytochrome c release activity (FIG. 12b). The potency of SAHB3$_{BID}$B, in particular, compares favorably with maximally activated myristolated BID protein, which releases approximately 65% cytochrome c under these conditions at doses of 30 nM.

Figure 13A:
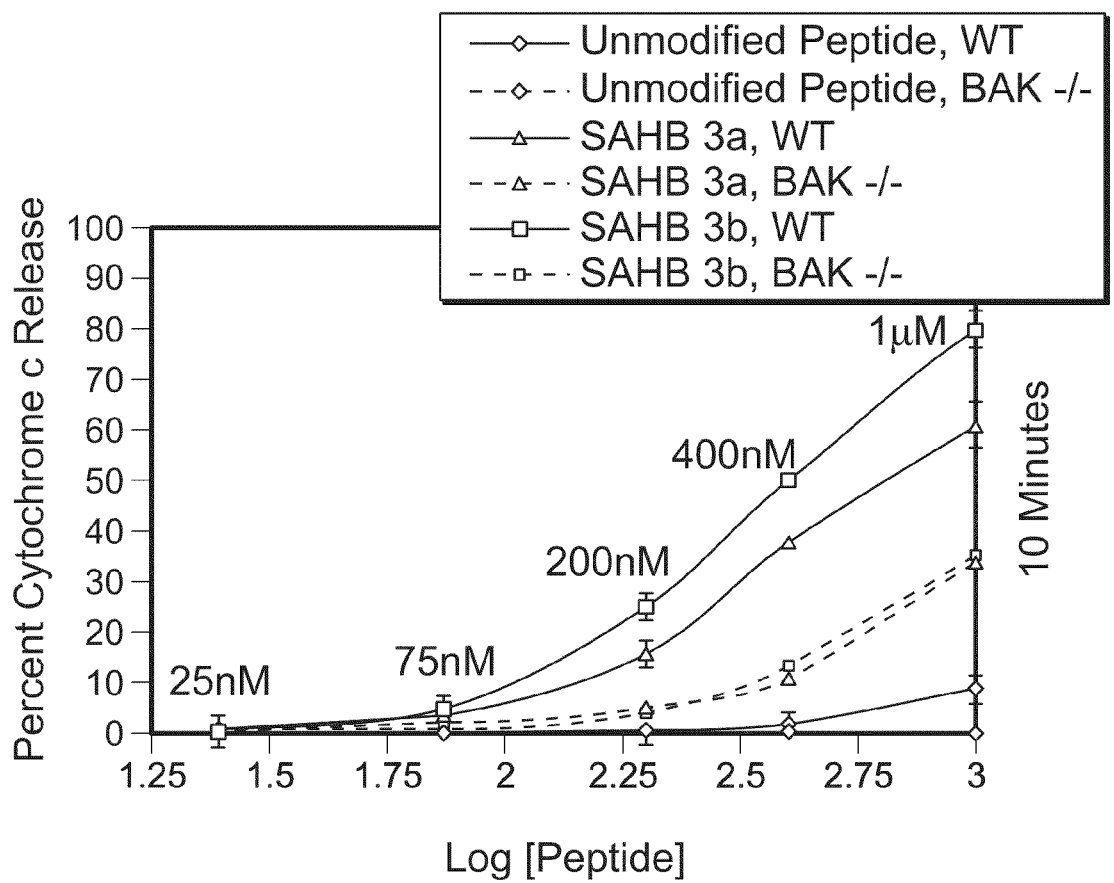
FIGS. 13a and 13b depict the results of a study showing that SAHB3$_{BID}$A- and SAHB3$_{BID}$B-induced cytochrome c release is faster and more potent than that of unmodified peptide.
Figure 13B:
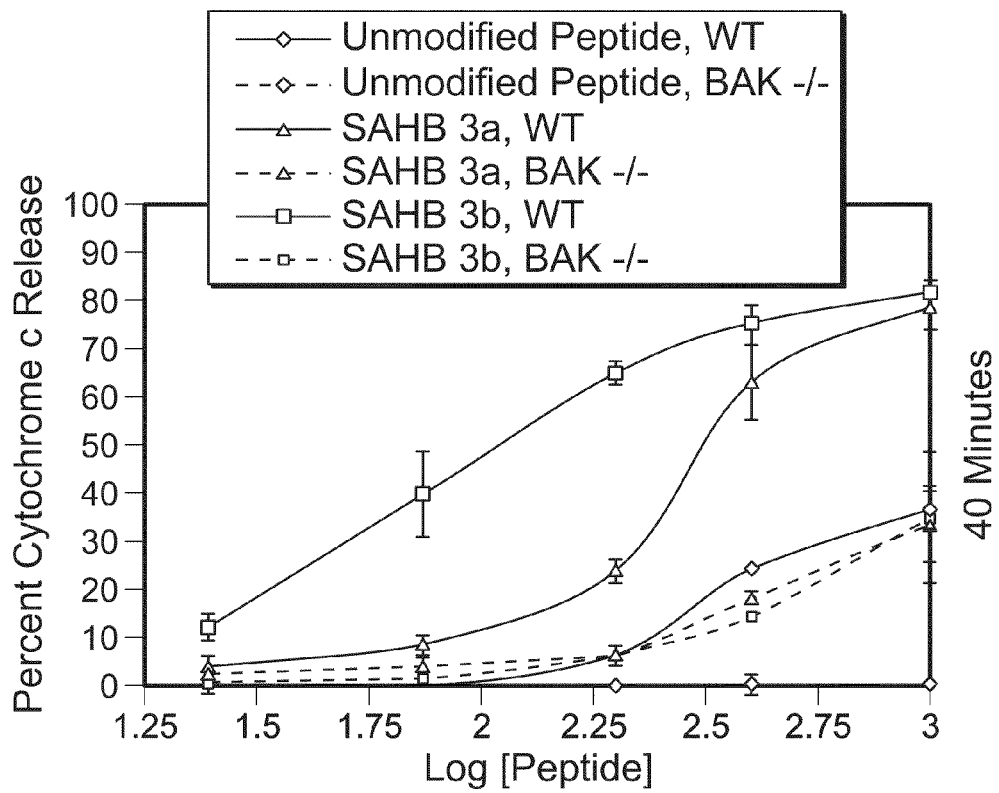
Figure 14:
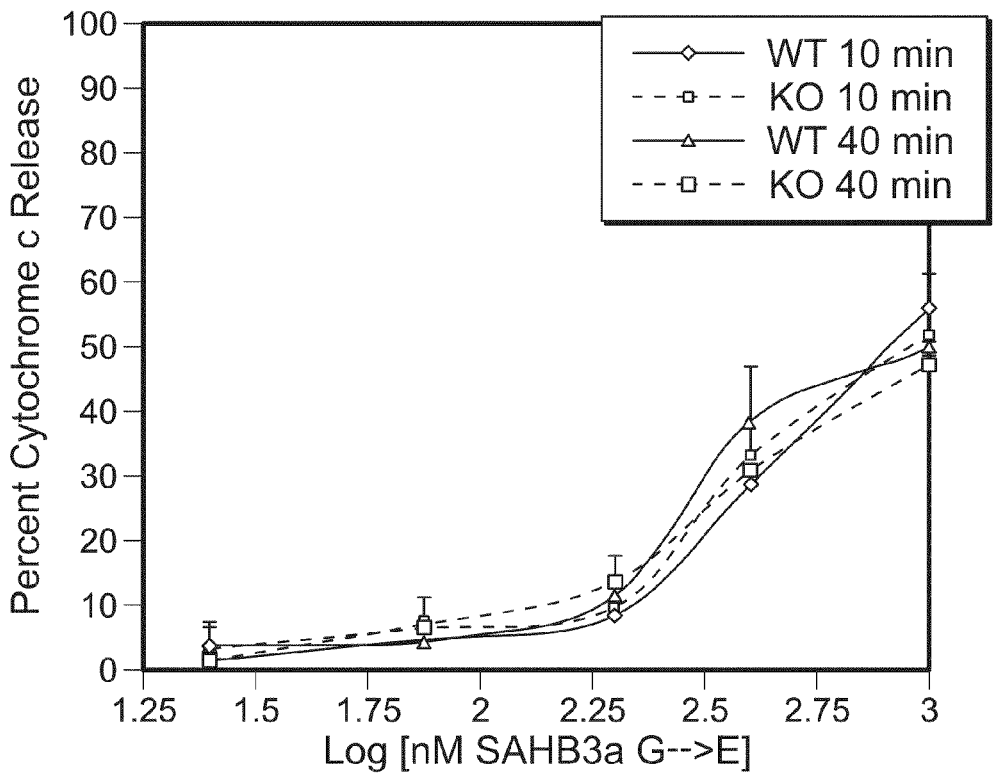
FIG. 14 depicts the results of a study showing that the Gly to Glu mutation of SAHB3$_{BID}$A selectively eliminates Bak-dependent cytochrome release, underscoring the specificity of action of SAHB3$_{BID}$A-induced cytochrome c release shown in FIG. 13.

The most active SAHB3$_{BID}$ compounds, A and B, were subjected to further kinetic studies to determine if helical preorganization can trigger more rapid cytochrome c release compared to the unmodified peptide. Similar to the above experiment, mouse liver mitochondria from wild-type and Bak–/– mice were exposed to the compounds at various concentrations and assayed for cytochrome c release at 10 and 40 minute intervals. Whereas at 10 minutes the unmodified peptide causes less than 10% release at the highest dose tested (1 µM), SAHB3$_{BID}$B has an EC50 for release at this timepoint of just under 400 nM, with almost maximal cytochrome release at 1 µM (FIG. 13a). Likewise, SAHB3$_{BID}$A triggers significant cytochrome c release at the 10 minute time interval. The EC50 for cytochrome c release at 40 minutes is 2.9 µM for the unmodified peptide and 310 and 110 nM for SAHB3$_{BID}$ A and B, respectively (FIG. 13b). Thus, SAHB3$_{BID}$A and B display a 10-25 fold enhancement in cytochrome c release activity at the 40 minute time point. Whereas the BAK-dependent cytochrome c release increases over time, the BAK-independent release does not change between the 10 and 40 minute timepoints, suggesting that this distinct release occurs early and is maximally achieved within 10 minutes. Of note, the negative control Gly to Glu point mutant of SAHB3$_{BID}$A, SAHB3$_{BID(G \to E)}$A, generates only Bak-independent cytochrome c release, confirming that SAHB3$_{BID}$A functions via the Bak-dependent mitochondrial apoptosis pathway (FIG. 14). Taken together, these cytochrome c release data indicate that SAHB3$_{BID}$A and B are capable of specifically inducing BAK-dependent cytochrome c release with markedly enhanced potency and kinetics compared to the unmodified peptide.

SAHB3$_{BID}$ Compounds Penetrate Intact Cells

Figure 15:
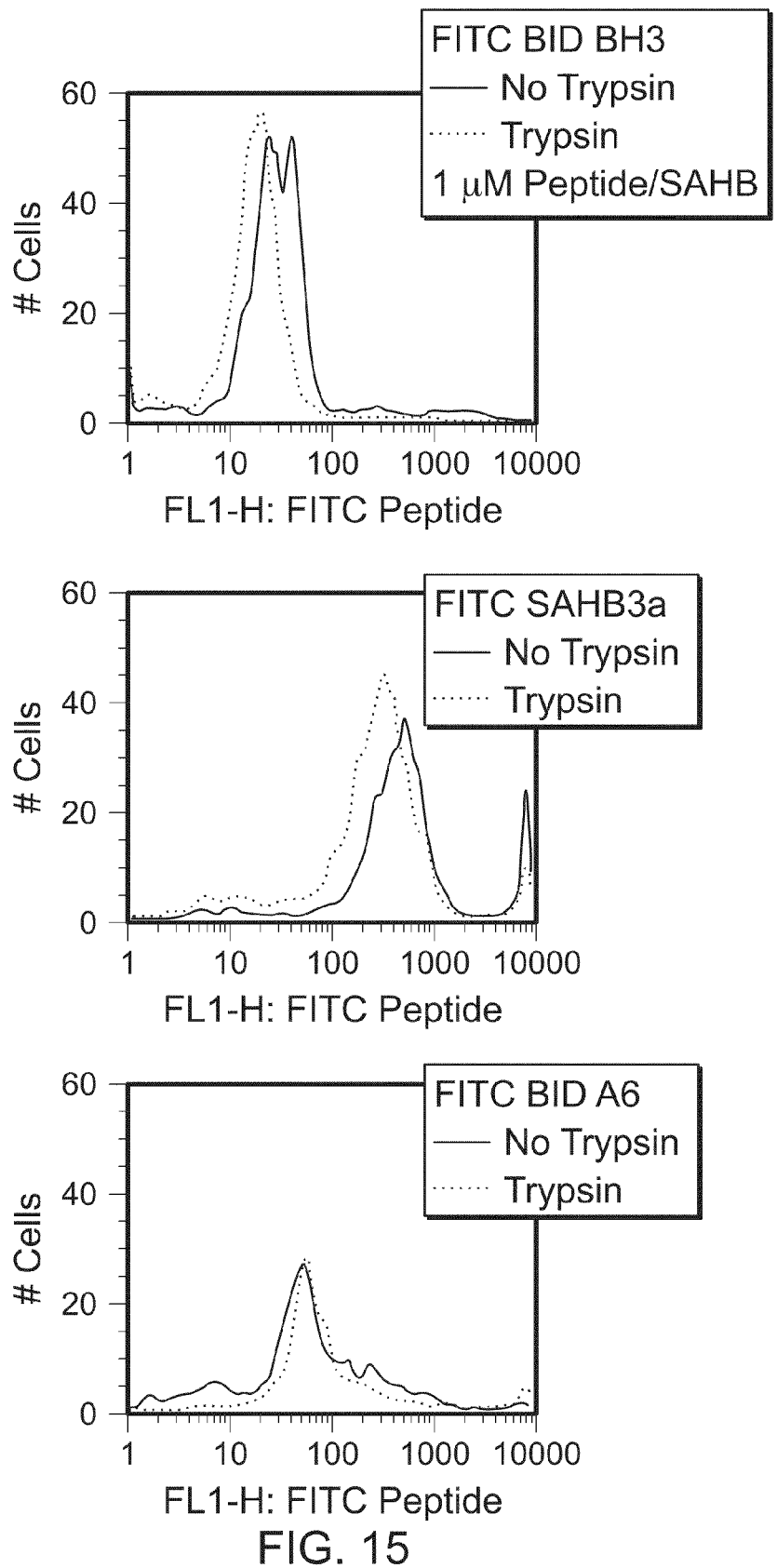
FIG. 15 depicts the results of a study showing that Jurkat T-cell leukemia cells, upon exposure to FITC-BID BH3 and FITC-BID helix 6, lack fluorescent labeling whereas Jurkat T-cell leukemia cells, upon exposure to FITC-SAHB3$_{BID}$ demonstrate a positive FITC signal, and that these results are not significantly altered by trypsin-treatment of the cells.
Figure 16A:
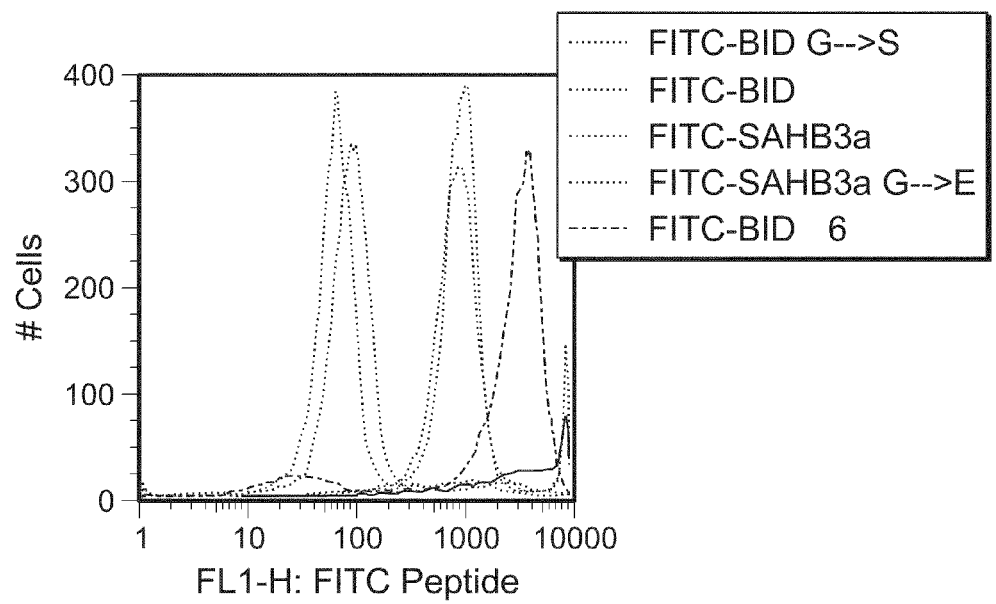
FIG. 16a depicts the results of a study showing that Jurkat T-cells exposed to cross-linked peptides FITC-SAHB3$_{BID}$A and SAHB3$_{BID(G \to E)}$A demonstrated fluorescent labeling, whereas Jurkat T-cells exposed to unmodified BH3 peptides FITC-BID and FITC-BID$_{(G \to S)}$ did not.

Fluorescein-derivatized SAHB3$_{BID}$ compounds, BID BH3 peptides, and a BID helix 6 peptide were incubated with Jurkat T-cell leukemia cells in culture for 4-24 hours and subsequently FACS sorted to determine percent labeling of leukemia cells. In order to avoid confounding results from cell-surface bound compounds, the Jurkat cells were washed thoroughly and subjected to trypsin overdigestion, in accordance with recent reports. For each compound tested, there was no significant change in the FITC signal profile after trypsin digestion, suggesting that in the case of these peptides, little to no FITC-labeled compound is surface bound (FIG. 15). Whereas BID BH3-treated cells were FITC-negative, both FITC-SAHB3$_{BID}$A- and FITC-SAHB3$_{BID(G \to E)}$A-treated cells were FITC-positive, as indicated by a rightward shift of the FITC signal (FIG. 16a). The similar profile of FITC-SAHB3$_{BID}$A and FITC-SAHB3$_{BID(G \to E)}$A in these cell permeability studies is particularly important, given the use of the point mutant compound as a negative control in biological experiments. BID helix 6, a cell permeable and membrane perturbing peptide, was used as a positive control for FITC-labeling in this experiment.

Figure 16B:
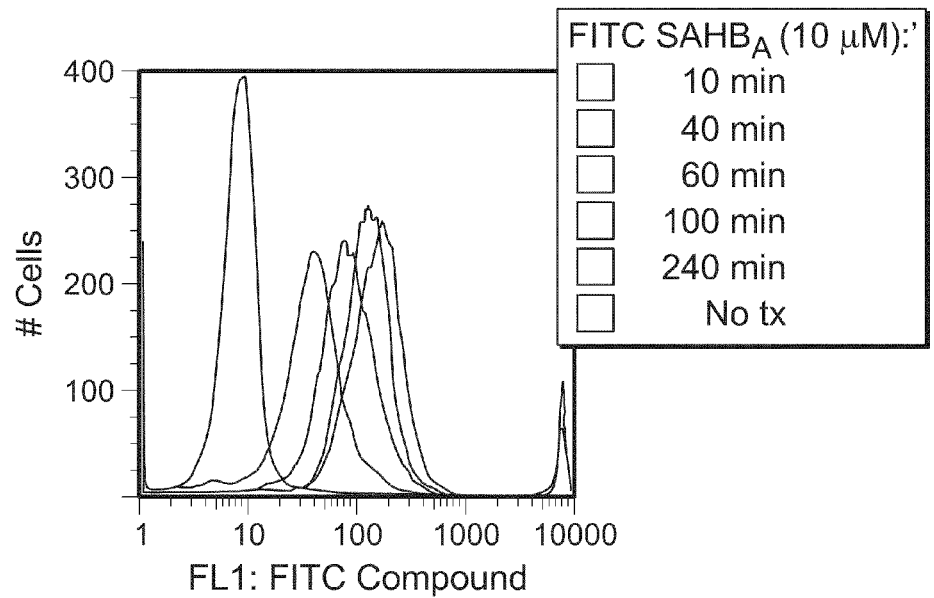
FIG. 16b depicts the results of a study showing that cellular import of FITC-SAHB3$_{BID}$A is time-dependent at 37° C., as assessed by FACS analysis.
Figure 17A:
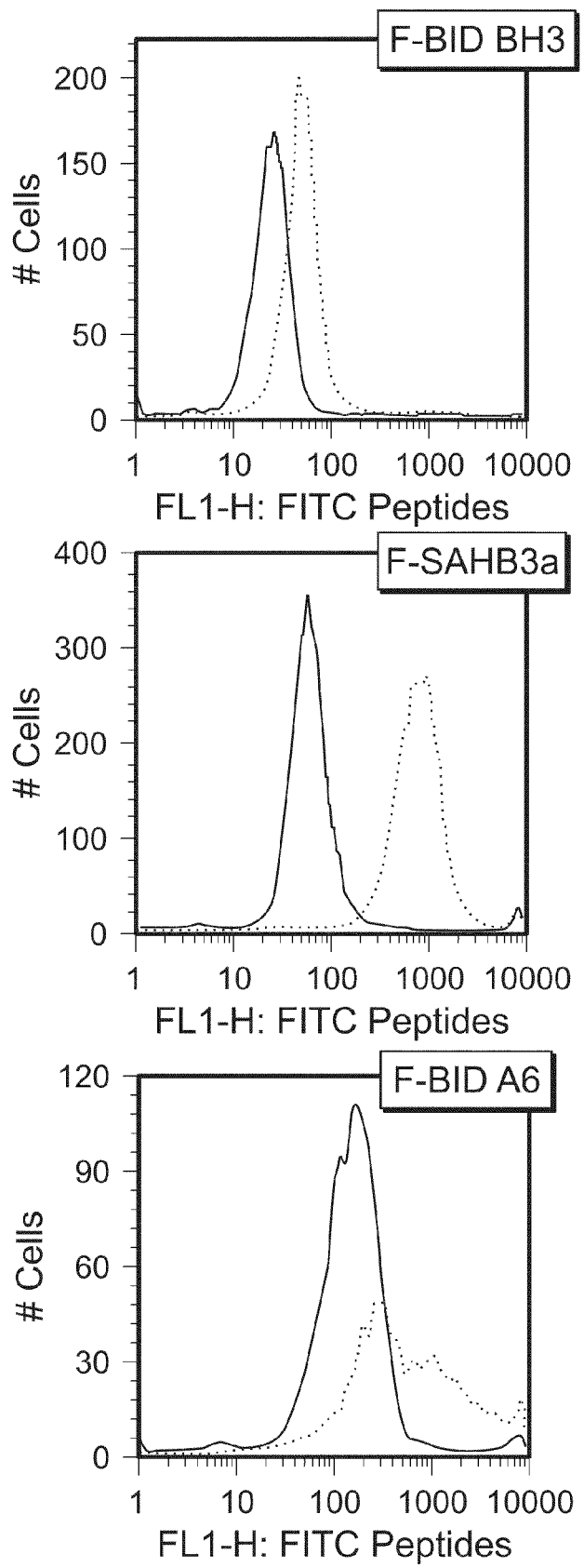
FIGS. 17a and 17b depict the results of a study showing Jurkat T-cells treated with FITC-peptides at 4° C. and 37° C.
Figure 17B:
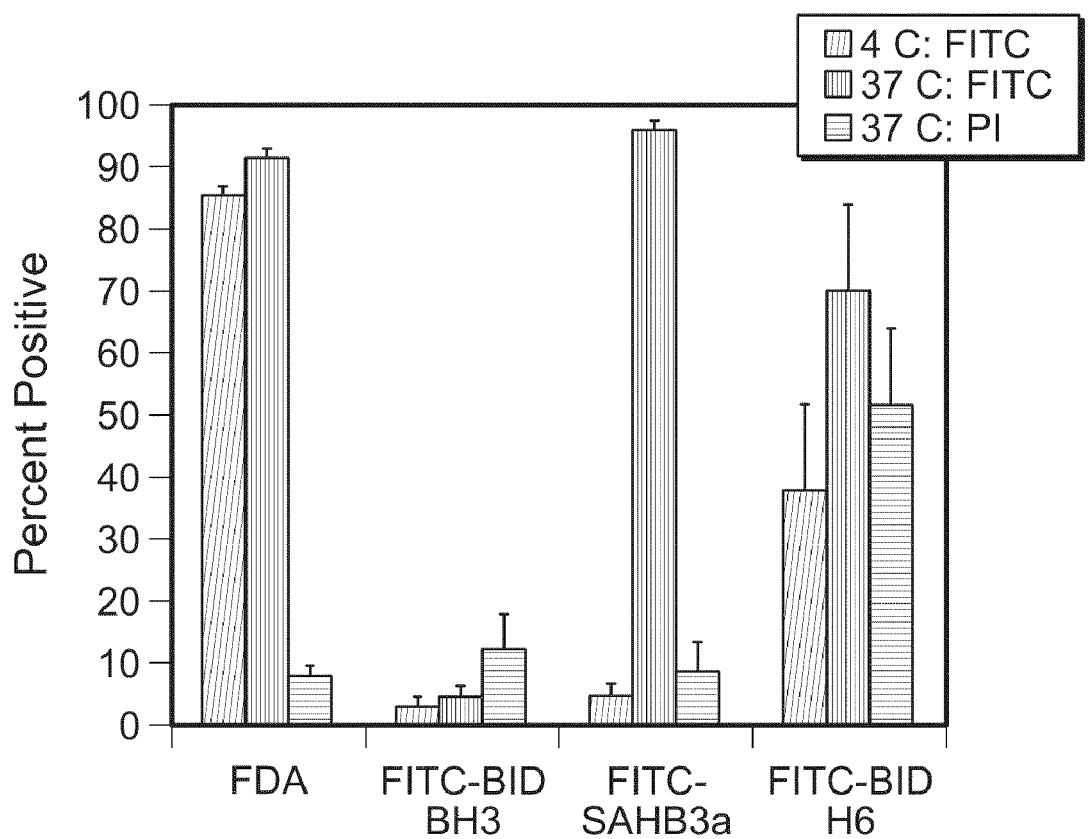
Figure 17C:
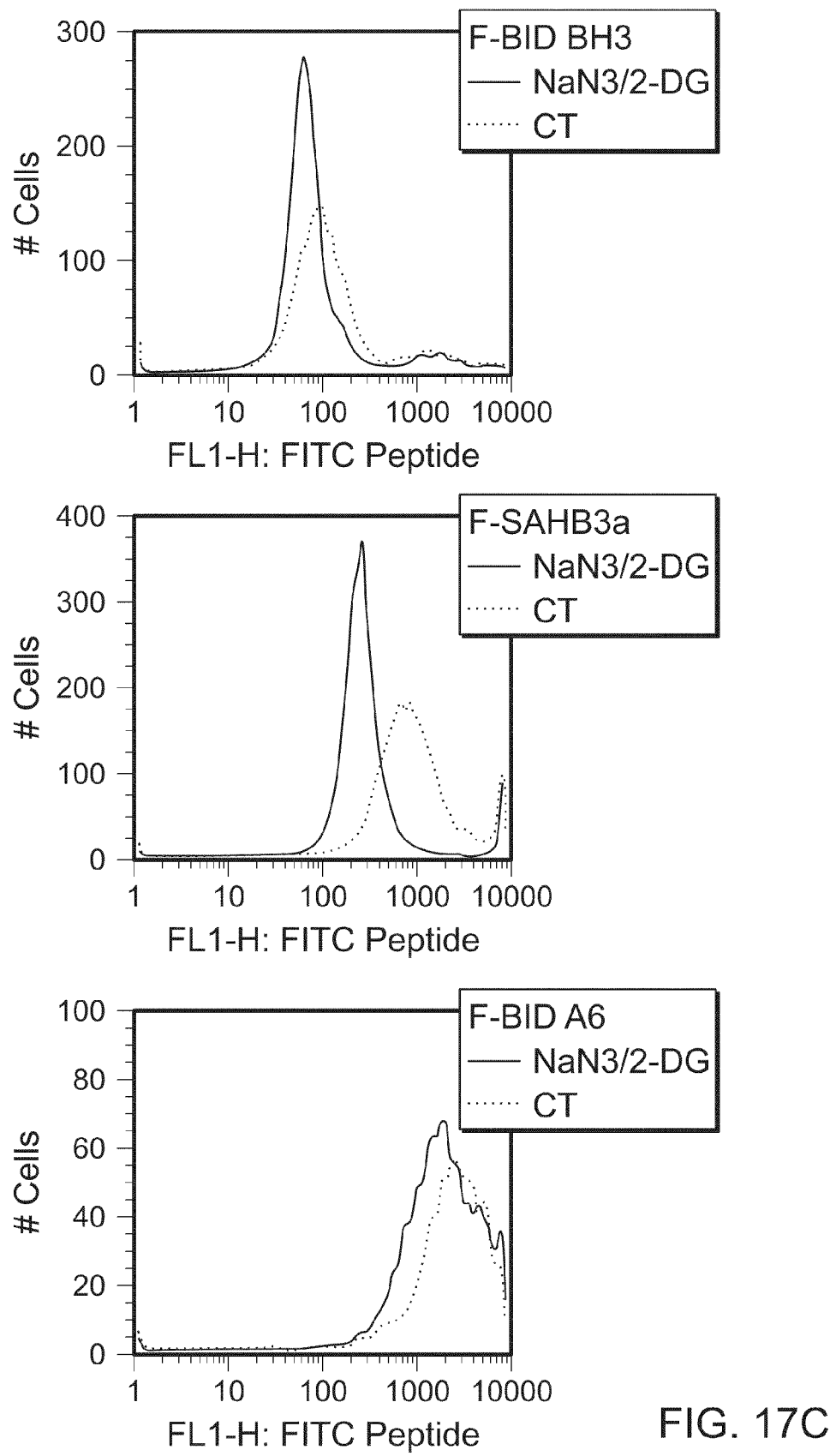
FIG. 17c depicts the results of a study showing that Jurkat T-cells, when preincubated with or without sodium azide and 2-deoxyglucose followed by treatment with FITC-peptides, showed no labeling for either condition with the FITC-BID BH3 polypeptide. The cells showed reduced labeling for FITC-SAHB3$_{BID}$A under sodium azide and 2-deoxyglucose conditions, and showed labeling with FITC-BID helix 6 under both conditions. These results are consistent with an ATP-dependant cellular uptake (e.g., endocytosis pathway) for SAHB3$_{BID}$ import.
Figure 18:
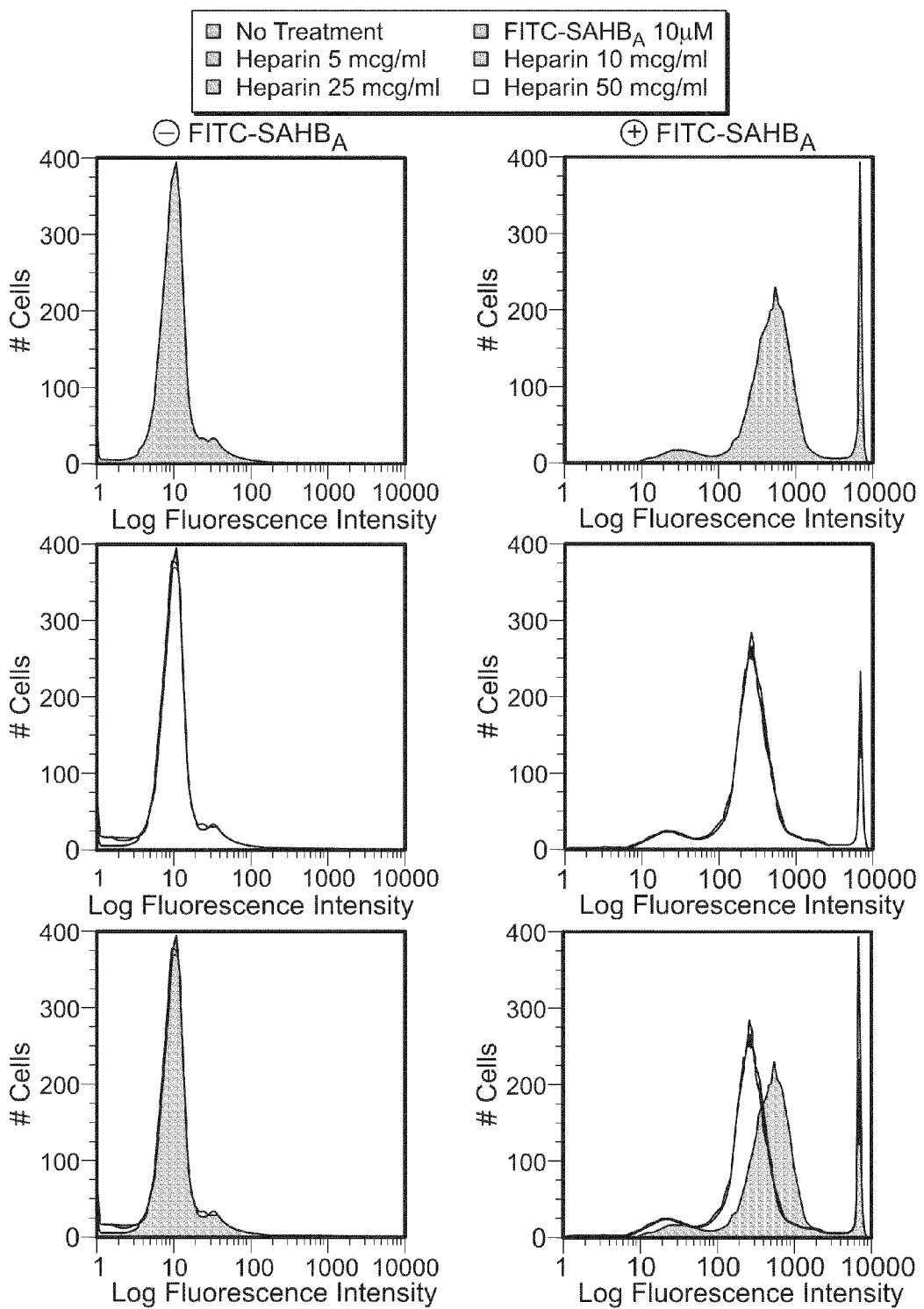
FIG. 18 depicts the results of a study showing that FITC-SAHB3$_{BID}$A uptake is not inhibited by cellular treatment with the glycosaminoglycan heparin, indicating that there are distinctions between the mechanism of binding and uptake of FITC-SAHB3$_{BID}$A compared to other cell penetrating peptides (CPPs), such as HIV TAT and Antennapedia peptides.

Surprisingly, it was discovered that FITC-SAHB3$_{BID}$A appears to enter the cell via endocytosis, a temperature- and energy-dependent transport pathway. Cellular import of FITC-SAHB3$_{BID}$A occurred in a time-dependent manner (FIG. 16b). When cellular endocytosis was inhibited by performing the experiment at 4° C. (FIG. 17a, 17b) or by treatment with the energy poisons sodium azide and 2-deoxyglucose (FIG. 17c), cell labeling was inhibited or markedly diminished, respectively. Of note, Jurkat cells labeled by FITC-SAHB3$_{BID}$A at 37° C. are propidium iodide (PI) negative, confirming that the crosslinked peptide does not merely function as a permeabilizing agent (FIG. 17b); in contrast, FITC-BID helix 6 readily penetrates at both temperatures, effectively permeabilizing the cells, as evidenced by the degree of PI positivity (FIG. 17b). These data support an endocytic mechanism of entry for the SAHB3$_{BID}$ compounds, consistent with recent reports citing cell-surface adherence followed by endocytosis as the mechanism of entry for other cell-penetrating peptides (CPPs), such as the HIV transactivator of transcription (TAT). Whereas highly basic CPPs, such as TAT and Antennapedia, are believed to be concentrated at the cell surface by adherence to negatively charged glycosaminoglycans SAHB3$_{BID}$A import was not inhibited in a dose-responsive manner by heparin (FIG. 18) The biophysical properties of the SAHB3$_{BID}$ amphipathic α-helix may facilitate distinct cell contacts via electrostatic and/or lipid membrane interactions.

Confocal microscopy experiments were employed in order to determine the intracellular localization of SAHB3$_{BID}$A. Jurkat T-cell leukemia cells were incubated with FITC-labeled compounds as described above or with serum replacement at 4 hours followed by additional 16 hours incubation at 37° C., and after washing twice with PBS, were cytospun at 600 RPM for 5 minutes onto superfrost plus glass slides (Fisher). Cells were then fixed in 4% paraformaldehyde, washed with PBS, incubated with TO-PRO-3 iodide (100 nM) (Molecular Probes) to counterstain nuclei, treated with Vectashield mounting medium (Vector), and then imaged by confocal microscopy (BioRad 1024). For double labeling experiments, fixed cells were additionally incubated with primary antibody to TOM20, and rhodamine-conjugated secondary antibody prior to TOPRO-3 counterstaining. For live confocal microscopy, double labeling of Jurkat cells was performed with FITC-SAHB$_4$ (10 µM) and MitoTracker (100 nM, Molecular Probes), tetramethylrhodamine isothiocyanate (TRITC)-Dextran 4.4 kD or 70 kD (25 mcg/mL, Molecular Probes), or Alexa Fluor 594-transferrin (25 mcg/mL, Molecular Probes) for 4 hours (dextran and transferrin) or 24 hours (MitoTracker). Due to limitations of photobleaching, BCL-2 overexpressing Jurkat cells were used for live confocal microscopy in order to optimize FITC imaging. FITC-SAHB$_4$ labeling of mitochondria was brighter in BCL-2 overexpressing Jurkats (consistent with the mechanism for SAHB activity), and thus image capture was facilitated using these cells. Treated Jurkats were washed twice and then resuspended in PBS and wet mount preparations analyzed with a BioRad 1024 (Beth Israel/Deaconess Center for Advanced Microscopy) or Zeiss LSM510 laser scanning confocal microscope (Children's Hospital Boston Imaging Core).

Figure 19A:
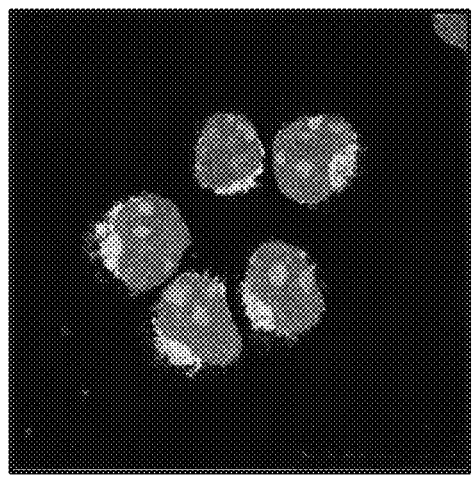
FIG. 19 depicts the results of a study showing that FITC-SAHB3$_{BID}$A compounds display cytoplasmic labeling with a vesicular distribution in Jurkat T-cells, whereas plasma membrane fluorescence is not evident. On the other hand, FITC-BID BH3 displays no cellular labeling of cells and FITC-BID helix 6 labels the cells diffusely and causes significant architectural destruction.
Figure 19B:
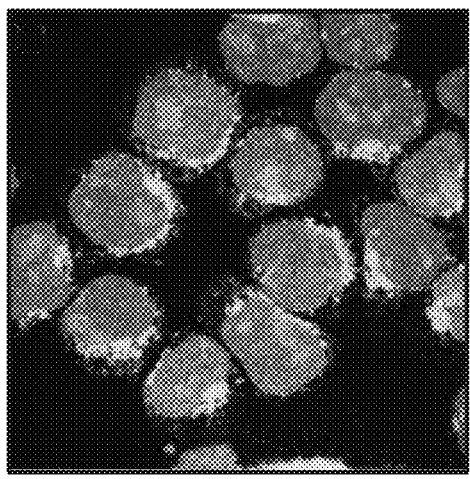
Figure 19C:
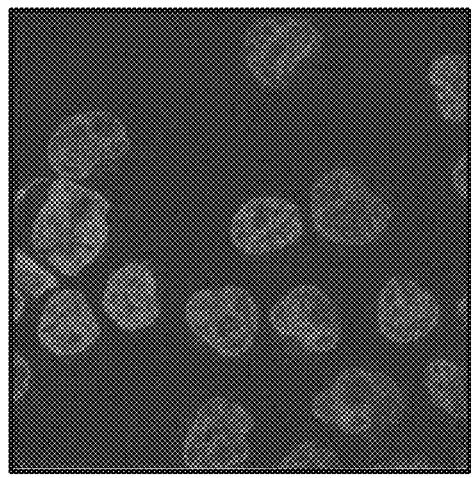
Figure 19D:
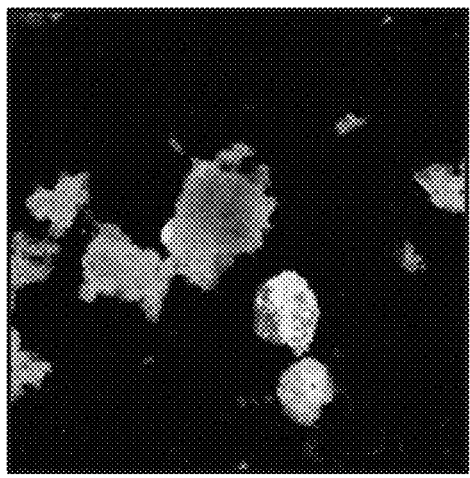
Figure 20A:
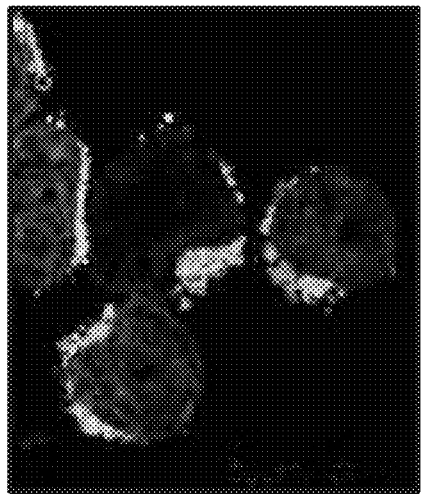
FIG. 20 depicts the results of a study showing that FITC-SAHB3$_{BID}$A co-localizes with a mitochondrial membrane marker in Jurkat T-cells.
Figure 20B:
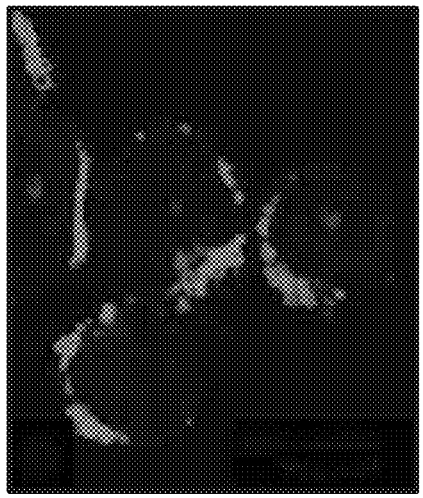
Figure 20C:
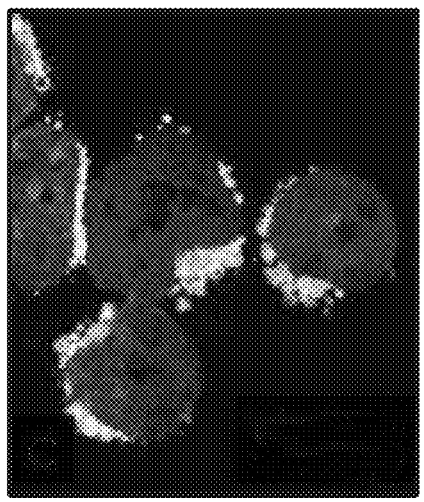

In fixed sections, SAHB3$_{BID}$A compounds localized to the cytoplasmic rim of the leukemic cells, with no plasma membrane or surface fluorescence evident; the vesicular pattern of fluorescence suggested an organelle-specific localization (FIGS. 19a and 19b). Consistent with the FACS data, Jurkat cells treated with FITC-BID BH3 showed no fluorescent labeling (FIG. 19c). Whereas FITC-SAHB3$_{BID}$A-treated cells display selective intracellular fluorescence and maintain their cellular architecture (FIG. 19a), FITC-BID helix 6-treated cells are diffusely labeled and demonstrate disrupted cellular morphology (FIG. 19d). Colocalization studies using FITC-SAHB3$_{BID}$A and an antibody to mitochondrial membrane protein Tom20, demonstrated extensive overlap of SAHB3$_{BID}$A fluorescence with mitochondria, the expected site of SAHB3BID's molecular targets (FIG. 20).

Live cell imaging performed 4 hr after SAHB treatment demonstrated an initial colocalization of FITC-SAHB$_A$ with dextran (4.4 kD or 70 kD)-labeled endosomes (FIG. 21$a$), but not transferrin-labeled endosomes (FIG. 21$b$), consistent with cellular uptake by fluid-phase pinocytosis (manuscript ref 27), the endocytic pathway determined for TAT and Antp peptides (manuscript ref 28). At a 24 hr time point, intracellular FITC-SAHB$_A$ showed increased colocalization with MitoTracker-labeled mitochondria in live cells (FIG. 21$c$) consistent with the mitochondrial colocalization observed in fixed cells using an antibody to Tom20, a mitochondrial outer membrane protein (FIG. 20). Taken together, the FACS data and confocal imaging demonstrate that the all-hydrocarbon crosslink enables SAHB3$_{BID}$A compounds to be imported by intact cells (e.g., through an endocytotic mechanism).

Figure 22A:
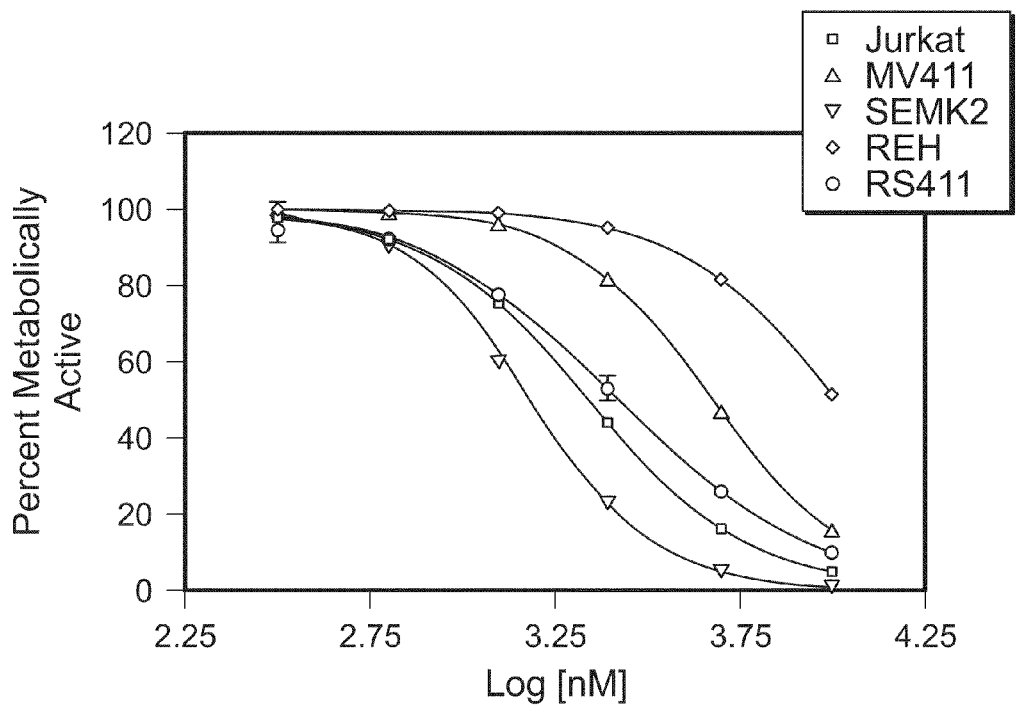
FIGS. 22a, 22b, and 22c depict the results of a study showing that SAHB3$_{BID}$A triggers metabolic arrest in a dose responsive fashion in the leukemia cell lines tested, whereas BID BH3 and SAHB3$_{BID(G \to E)}$A had essentially no effect in this dose range.
Figure 22B:
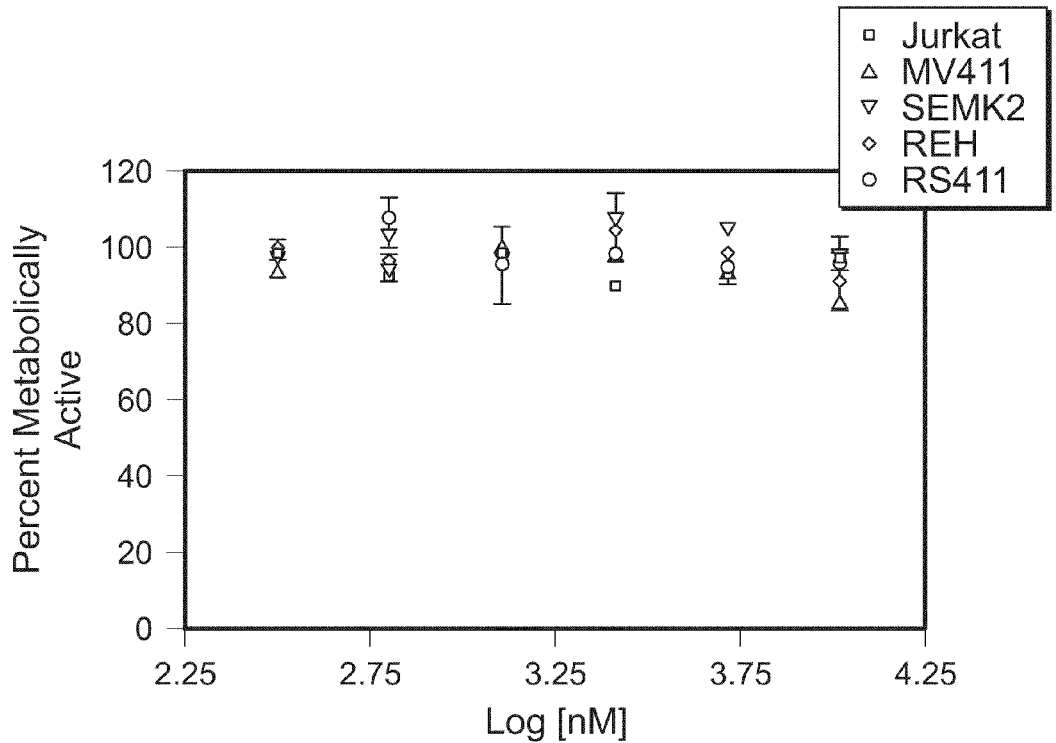
Figure 22C:
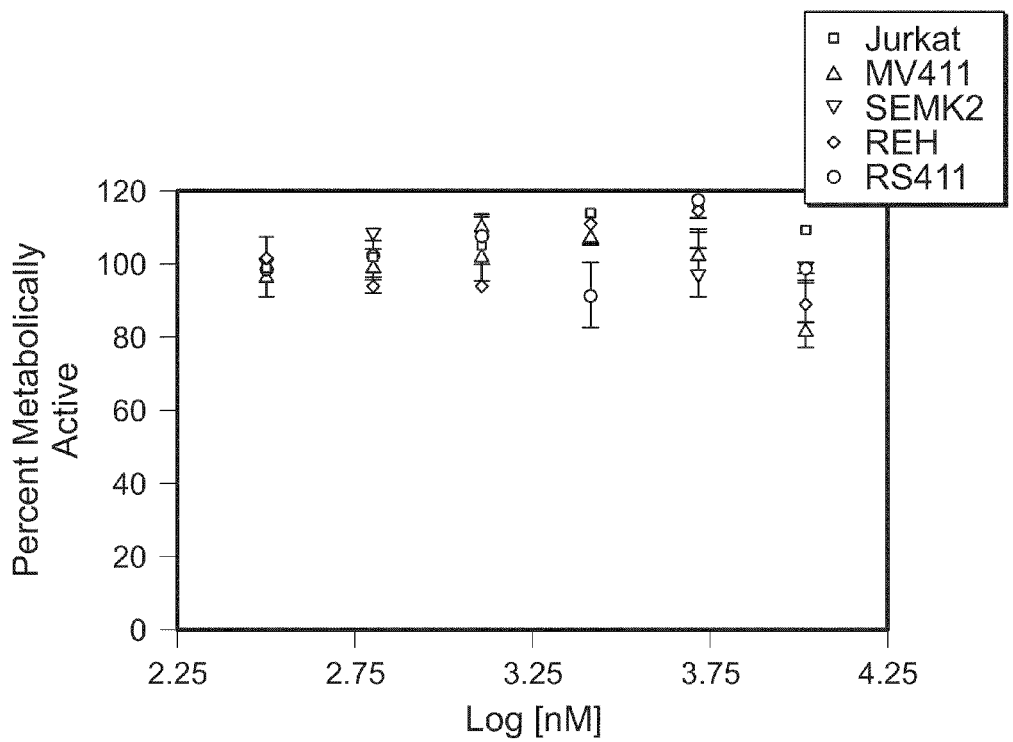

SAHB3$_{BID}$ Compounds Trigger Apoptosis of B-, T-, and Mixed-Lineage Leukemia (MLL) Cells In order to assess whether SAHB3$_{BID}$ compounds could arrest the growth of proliferating leukemia cells in culture, 3-(4,5-dimethylthiazol-2-yl)2,5-dipheny tetrazolium bromide, MTT assays using serial dilutions of SAHB3$_{BID}$A were performed on T-cell (Jurkat), B-cell (REH), and Mixed Lineage Leukemia (MLL)-cells (MV4; 11, SEMK2, RS4; 11) in culture. SAHB3$_{BID}$A inhibited the leukemic cells at IC$_{50}$s of 2.2 (Jurkat), 10.2 (REH), 4.7 (MV4;11), 1.6 (SEMK2), and 2.7 (RS4;11) μM (FIG. 22$a$). Neither the BID BH3 peptide nor the SAHB$_{A(G \to E)}$ point mutant had an effect in this dose range (FIG. 22$b$, 22$c$).

Figure 23A:
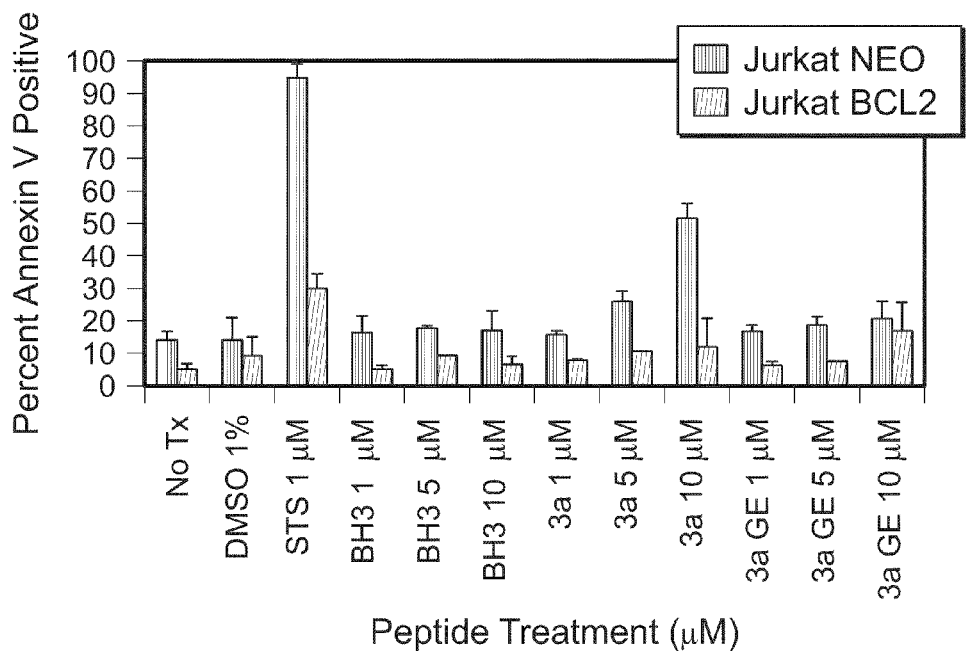
FIG. 23 depicts the results of a study showing that SAHB3$_{BID}$A and SAHB3$_{BID}$B induced apoptosis in up to 50% of intact Jurkat cells at 10 μM, an effect specifically inhibited by BCL-2 overexpression (black bars). Unmodified BID BH3 peptide and the gly to glu mutants had no effect based on comparison with the no treatment control.
Figure 23B:
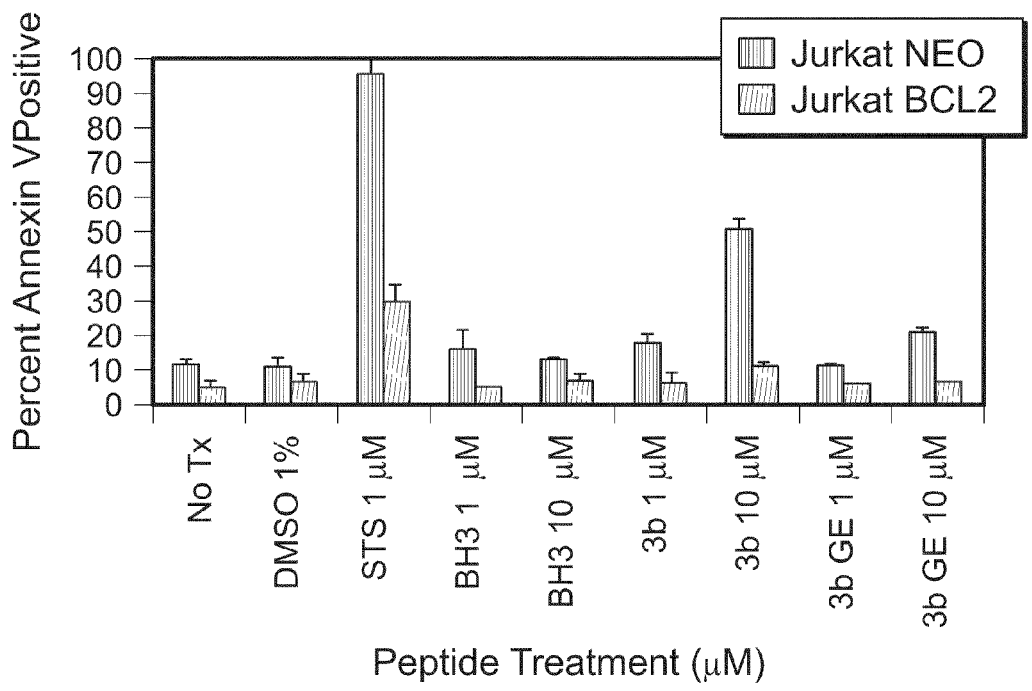
Figure 24:
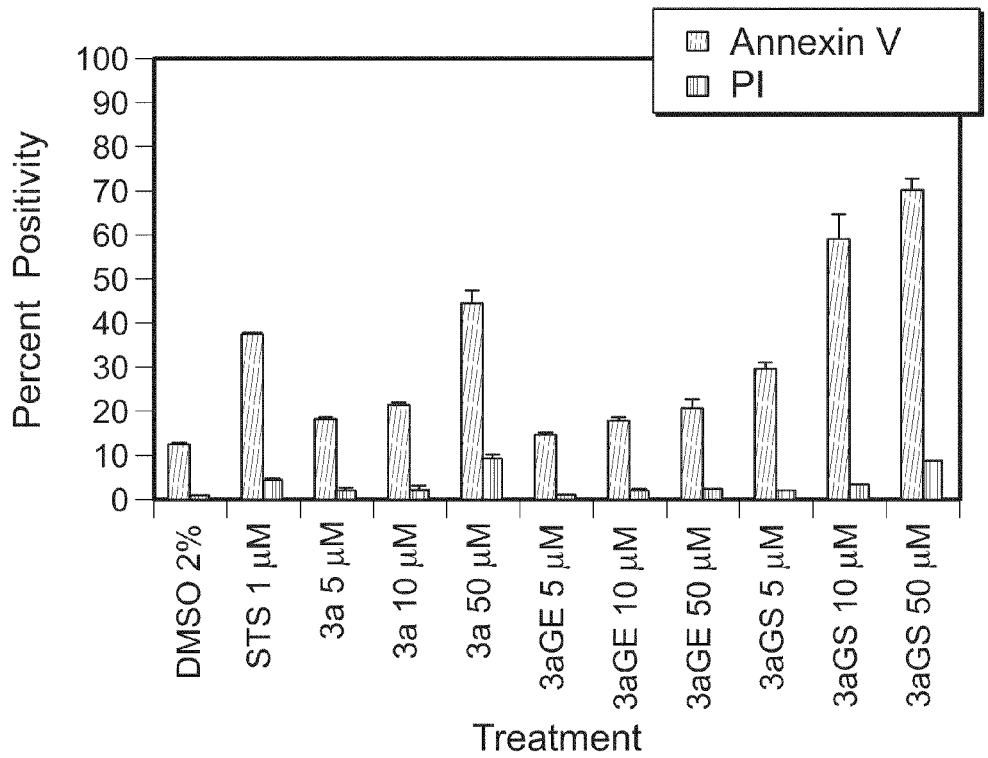
FIG. 24 depicts the results of a study showing the dose response of Jurkat BCL-2 overexpressing cells treated with SAHB3$_{BID}$A, SAHB3$_{BID(G \to E)}$ and SAHB3$_{BID(G \to S)}$A. Whereas SAHB3$_{BID}$A and SAHB3$_{BID(G \to E)}$A can overcome BCL-2 inhibition of apoptosis in this dose range, the gly to glu point mutant has not effect.
Figure 25:
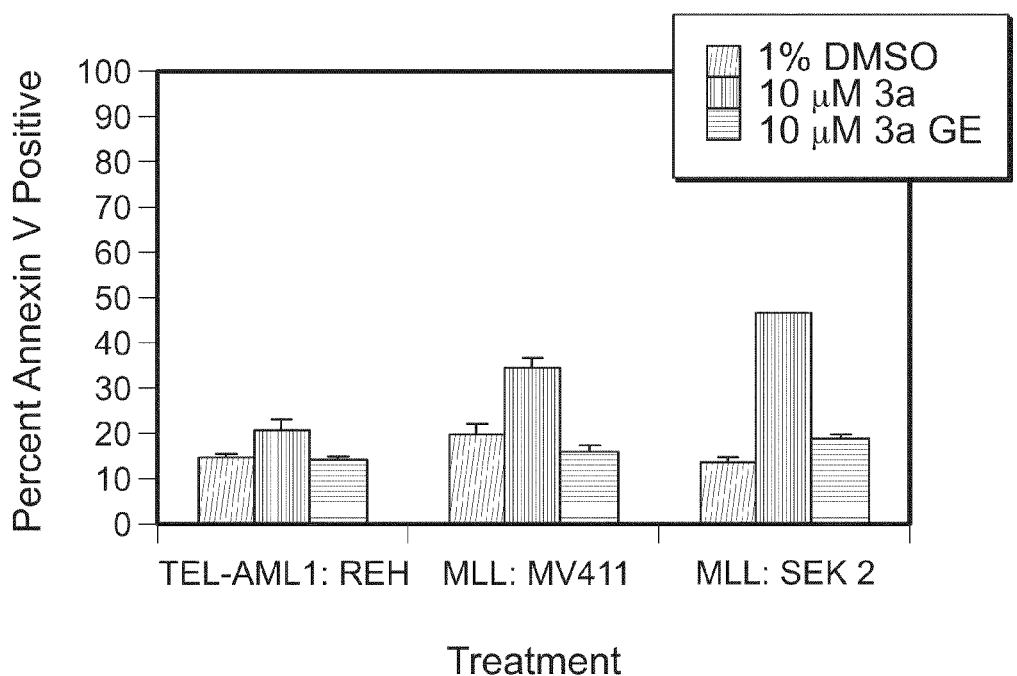
FIG. 25 depicts the results of a study showing that SAHB3$_{BID}$A treated leukemia cell lines REH, MV4; 11, and SEMK2 underwent specific apoptosis induction, whereas the gly to glu point mutant SAHB3$_{BID(G \to E)}$A had no effect on the cells.

To assess whether this metabolic arrest represented apoptosis induction, Jurkat leukemia cells were treated with 10 μM SAHB3$_{BID}$A and B, SAHB3$_{BID(G \to E)}$A and B, and unmodified BID BH3 peptide, in serum-free media for 4 hours followed by a 16 hour incubation in serum-containing media (i.e. final peptide concentrations of 5 μM), and then assayed for apoptosis by flow cytometric detection of annexin V-treated cells. SAHB3$_{BID}$A and B demonstrated between 40-60% annexin V positivity by 20 hours post treatment, whereas the unmodified peptide and SAHB3$_{BID}$ point mutants had no effect (FIGS. 23$a$ and 23$b$). Comparable studies that use either unmodified BH3 peptides with carrier reagents or engineered helices with nonspecific mitochondrial perturbing effects, required doses of 200-300 μM to activate apoptosis. An additional control experiment using Jurkat cells engineered to overexpress BCL-2 was subsequently undertaken to assess whether SAHB3BID-induced apoptosis could be decreased by excess BCL-2, which would suggest that the compounds specifically function within cells through the mitochondrial apoptosis pathway. Indeed, the pro-apoptotic effect of 10 uM SAHB3$_{BID}$A and B on "wild-type" Jurkats was abolished in the BCL-2 overexpressing cells. This protective effect, however, can be overcome by dose escalation of SAHB3$_{BID}$A but not of SAHB3$_{BID(G \to E)}$A (FIG. 24); in addition, a gly to ser point mutant of SAHB3$_{BID}$A (SAHB3$_{BID(G \to S)}$A), which does not exhibit BCL-2 binding affinity (see above), is equally effective as a pro-apoptotic in "wild-type" and BCL-2 overexpressing Jurkat cells (FIG. 24). Apoptosis induction assays using SAHB3$_{BID}$A and SAHB3$_{BID(G \to E)}$A were additionally performed in the REH, MV4; 11, and SEMK2 cell lines with similar results (FIG. 25). Taken together, these data indicate that SAHB3$_{BID}$ compounds can penetrate and kill proliferating leukemia cells. The observed pro-apoptotic effects are selectively abolished by gly to glu mutation of SAHB3$_{BID}$A and cellular overexpression of BCL-2, findings which underscore that SAHB3$_{BID}$ compounds function via the defined mitochondrial apoptosis pathway.

Figure 26A:
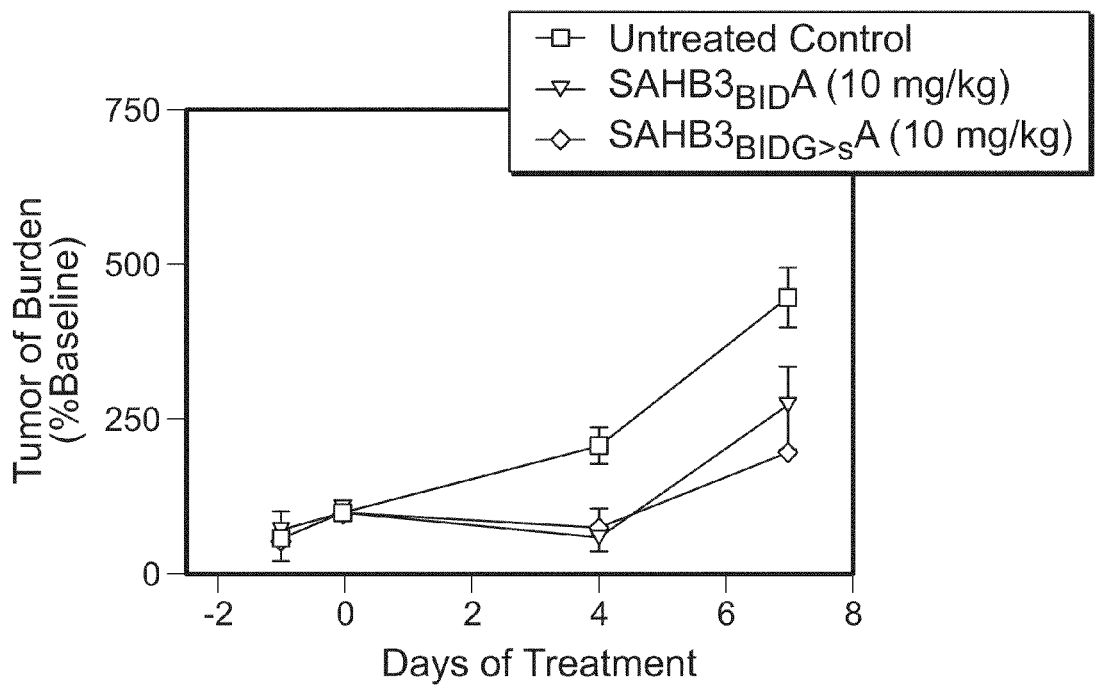
FIGS. 26a and 26b depict the results of a study showing that both SAHB3$_{BID}$A and SAHB3$_{BID(G \to E)}$A suppressed the growth of SEMK2 leukemia in NOD-SCID mice, with SAHB3$_{BID(G \to E)}$A demonstrating a greater potency than SAHB3$_{BID}$A.
Figure 26B:
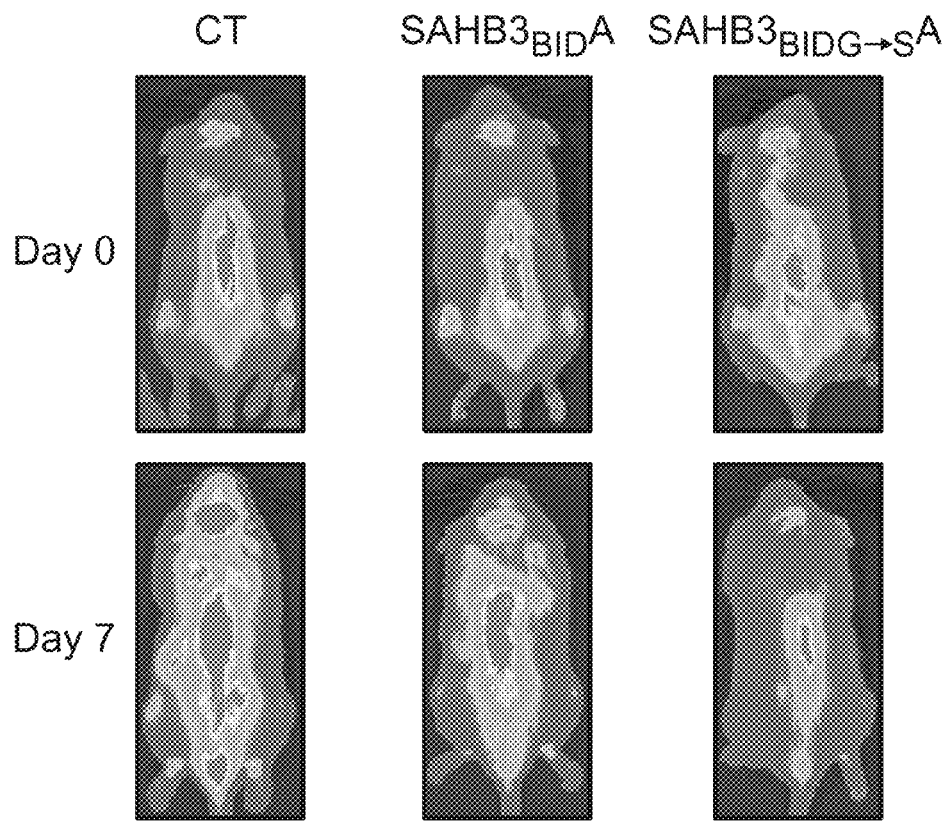
Figure 27A:
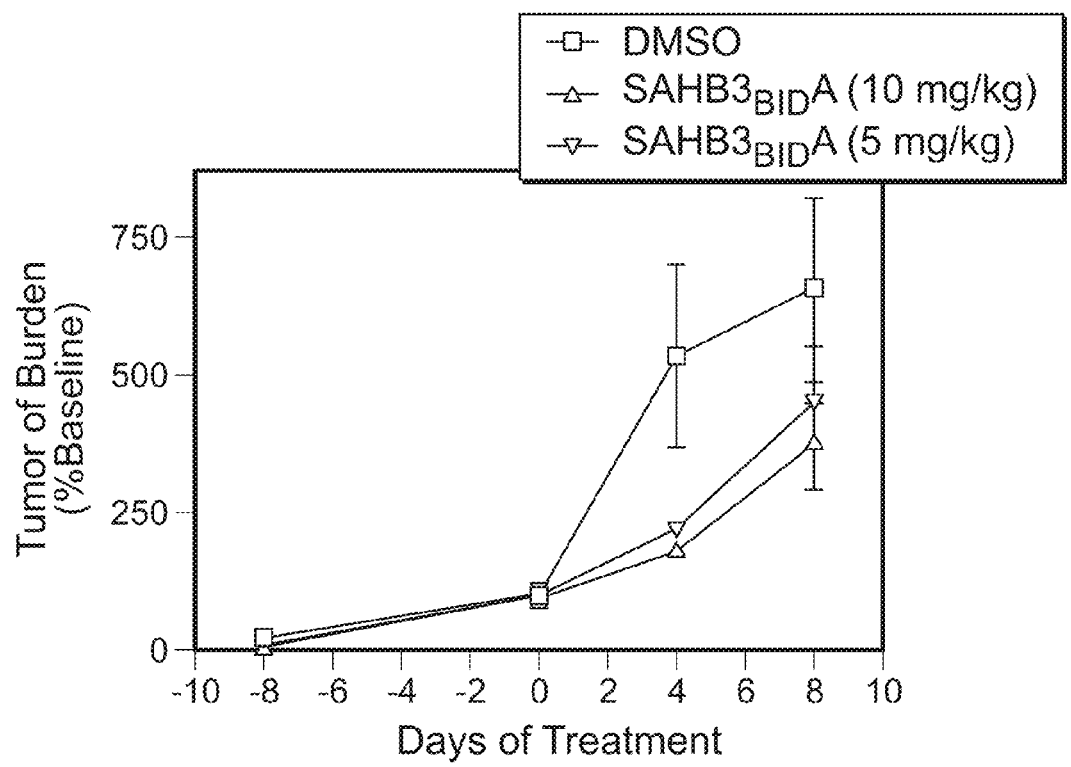
Figure 27B:
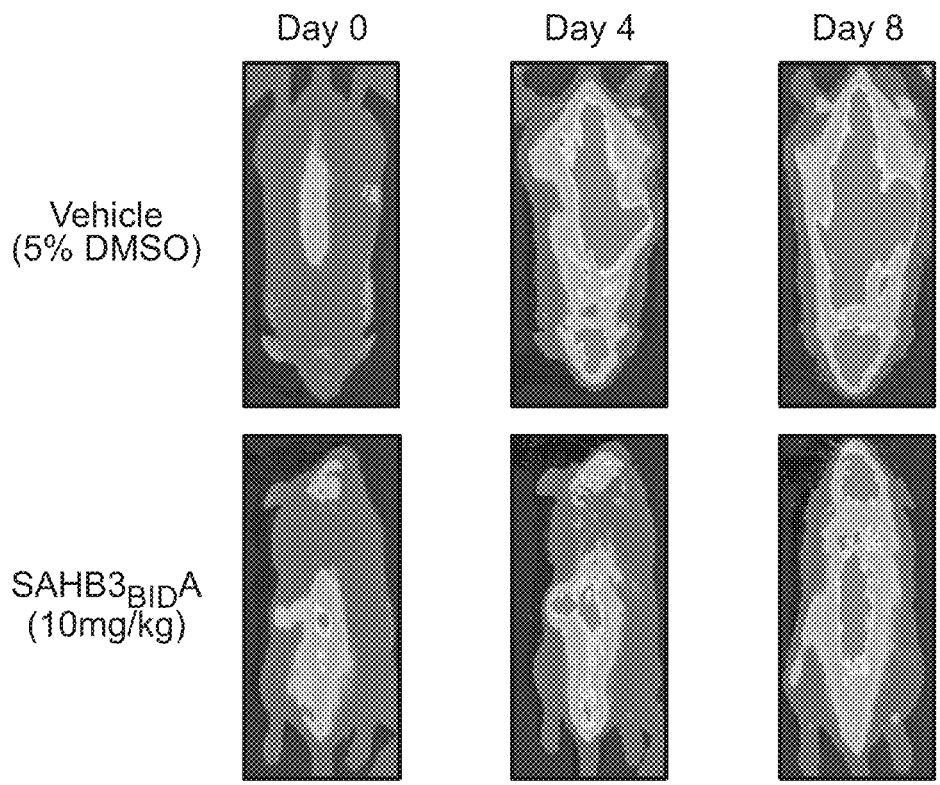
Figure 27C:
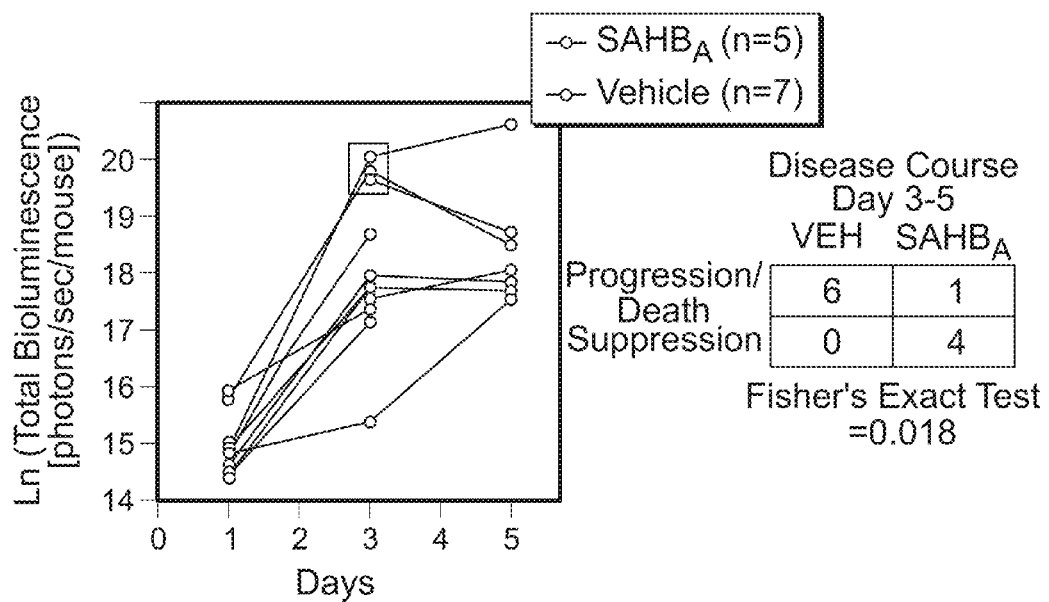
FIGS. 27c, 27d, 27e depict the results of an animal study showing that SAHB3$_{BID}$A inhibits the growth of RS4; 11 leukemia relative to vehicle in SCID beige mice, with statistically significant prolongation of survival in SAHB3$_{BID}$A-treated mice compared to vehicle controls.
Figure 27D:
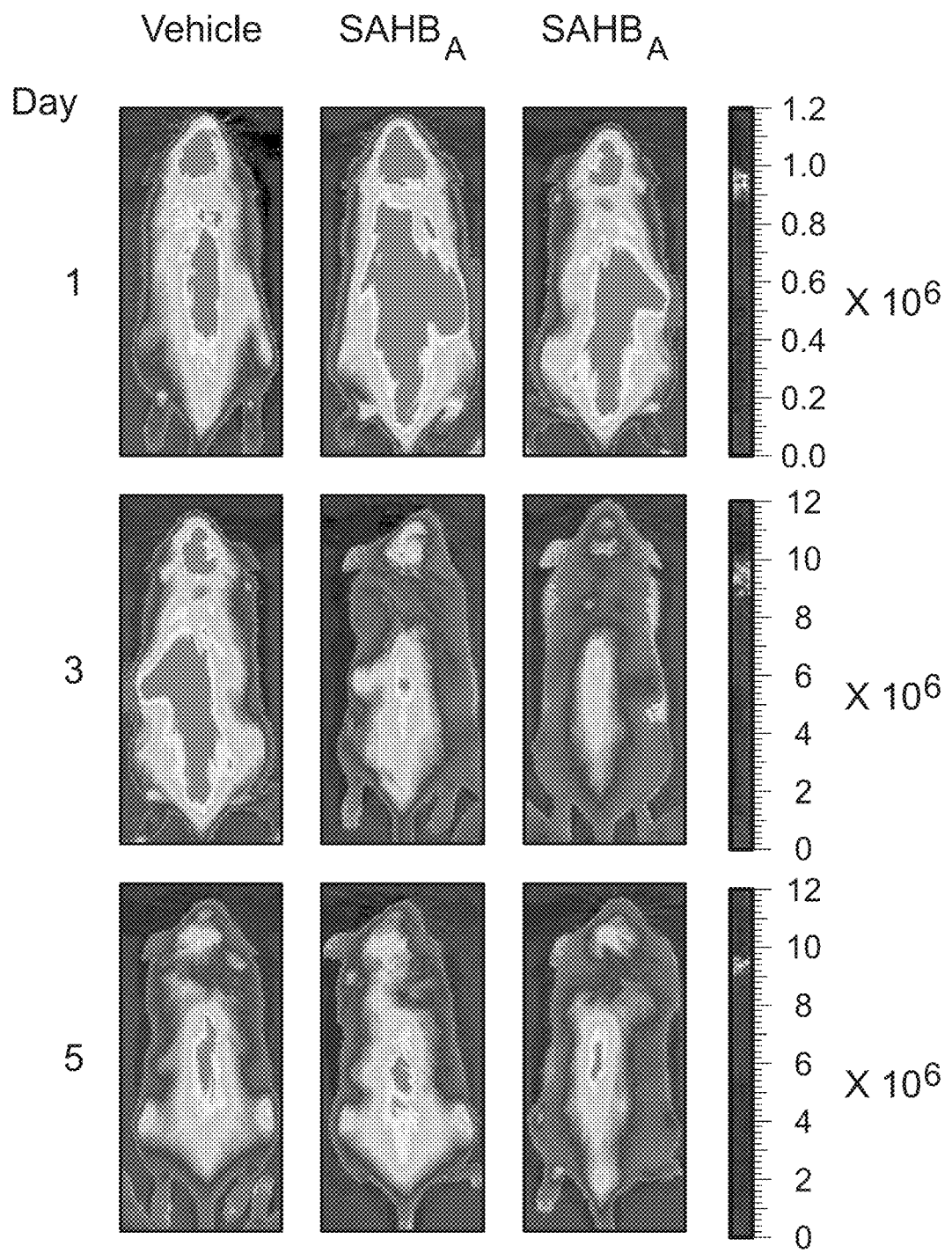
Figure 27E:
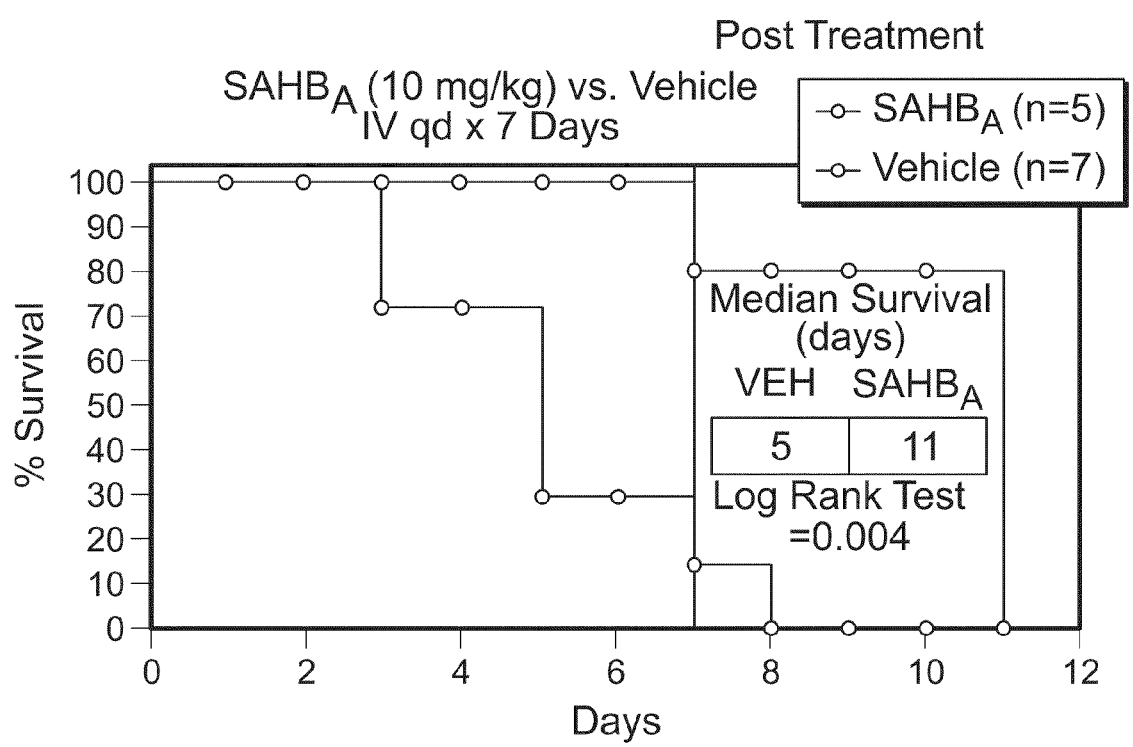
Figure 27F:
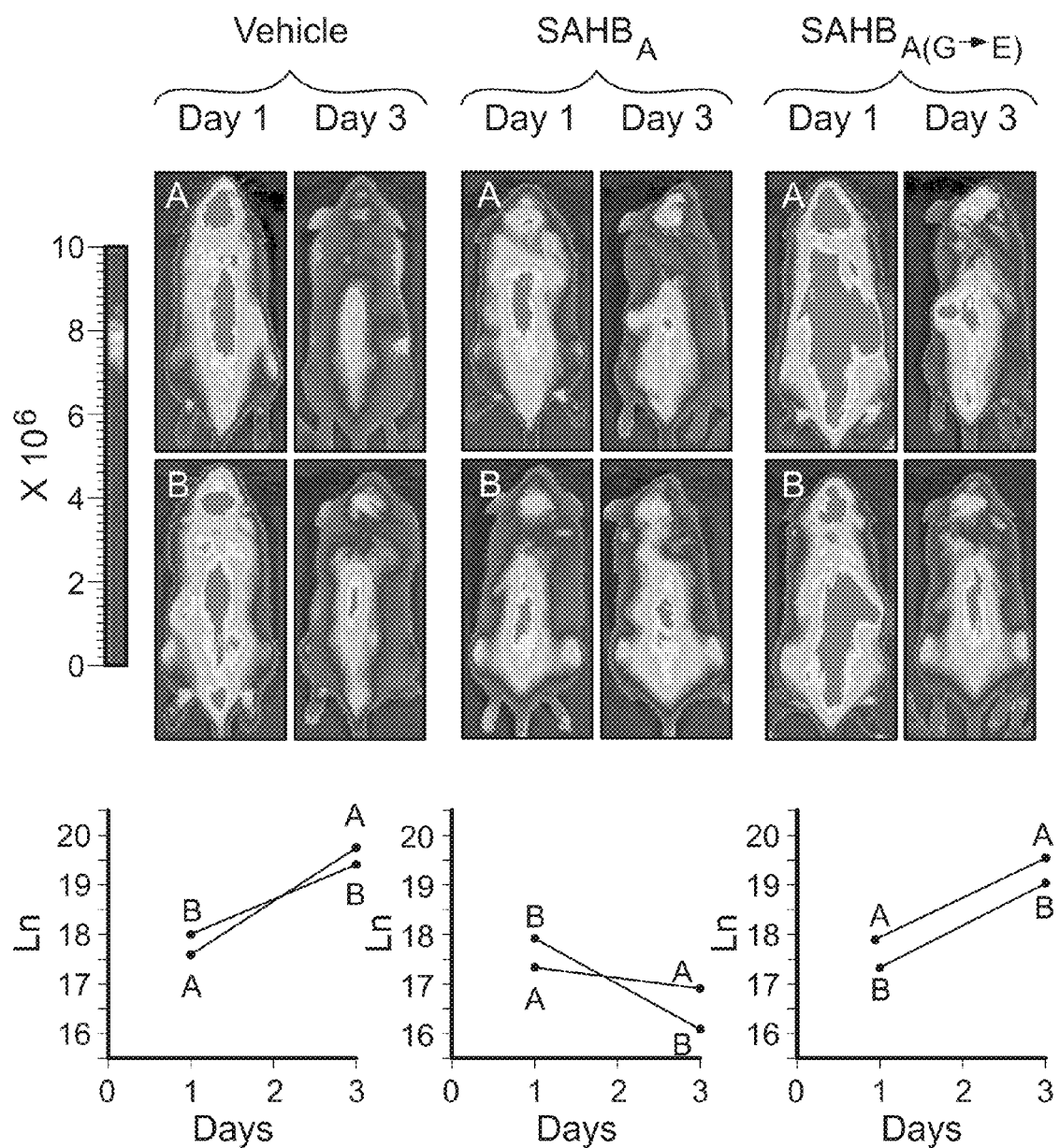
FIG. 27f depicts the results of an animal study again showing that SAHB3$_{BID}$A causes regression of RS4; 11 leukemia in SCID beige mice, in contrast with SAHB3$_{BID(G \rightarrow E)}$A- and vehicle-treated mice which demonstrate leukemia progression.
Figures 1, 2, 28C:
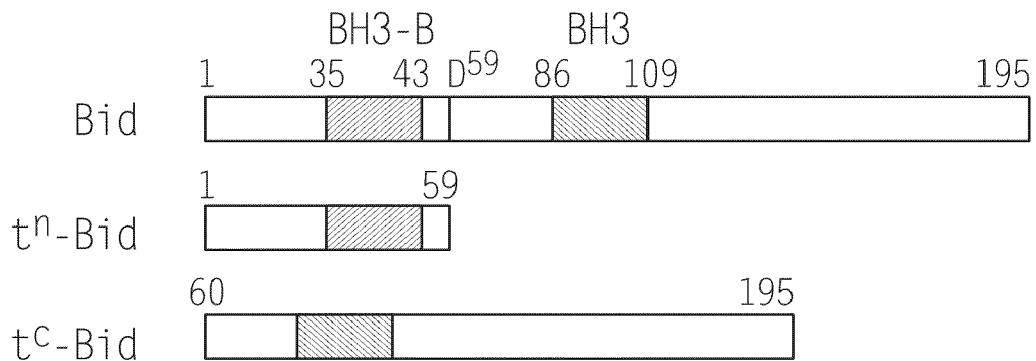
Figures 2, 3, 28D:
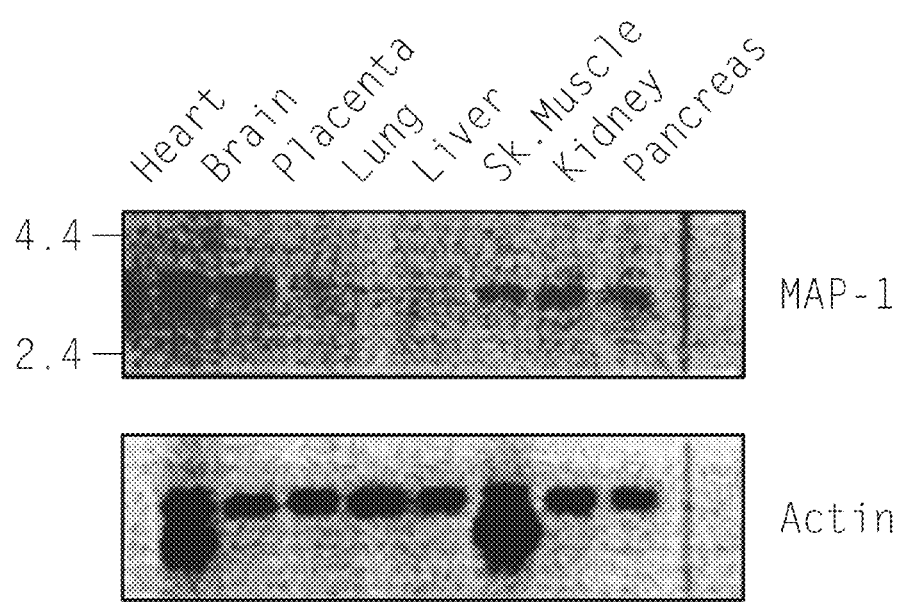
Figure 28H:
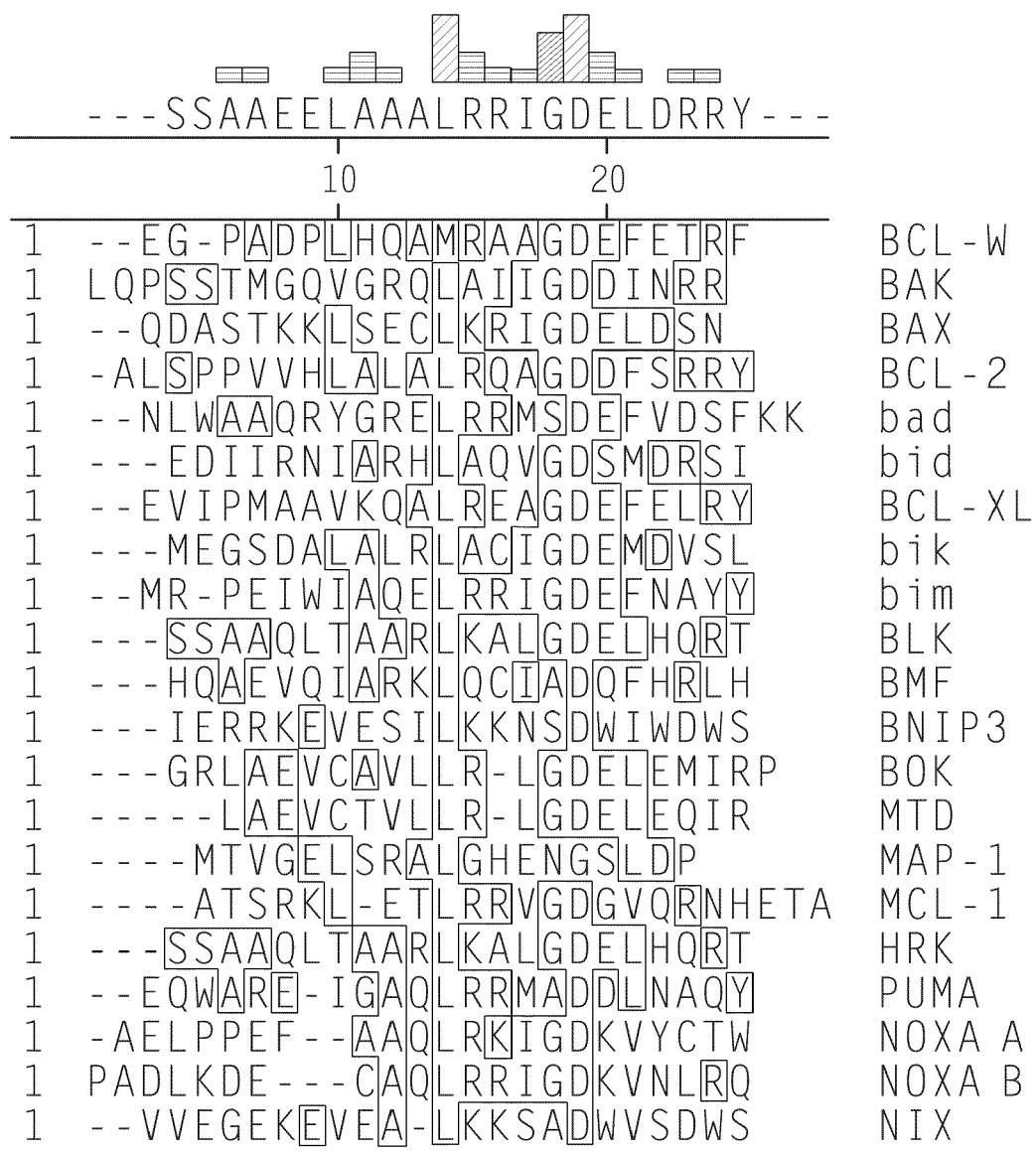
FIG. 28 (A-1), (A-2), and (B-1) show sequences of alpha helical domains of various BCL-2 family member proteins (A-1 shows SEQ ID NOs: 1-2; A-2 shows SEQ ID NOs: 3-9; and B-1 shows SEQ ID NOs: 10-15).

SAHB3$_{BID}$A and SAHB3$_{BIDG \to S}$A Demonstrate Leukemic Suppression In Vivo NOD-SCID mice were subjected to 300 cGy total body irradiation followed by intravenous injection of 4×10$^6$ SEMK2-M1 leukemia cells exhibiting stable luciferase expression. The mice were monitored weekly for leukemia engraftment using the In Vivo Imaging System (IVIS, Xenogen), which quantitates total body luminescence after intraperitoneal injection of D-luciferin. On day 0, the leukemic mice were imaged and then treated intravenously with 10 mg/kg of SAHB3$_{BID}$A, SAHB3$_{BIDG \to S}$A, or no injection on days 1, 2, 3, 5, 6. Total body luminescence was measured on days 4 and 7. Referring to FIG. 26$a$, analysis of tumor burden among the groups demonstrates leukemic suppression by SAHB3$_{BID}$A and SAHB3$_{BID(G \to S)}$A compared to untreated control mice. Referring to FIG. 26$b$, total body luminescence images demonstrate more advanced leukemia in the untreated group by day 7 (red density, representing high level leukemia, is seen throughout the skeletal system) compared to the SAHB3$_{BID}$A-treated mice, which demonstrate lower level and more localized disease. Interestingly, the G-->S mutant, which cannot be sequestered by BCL-2 appears to be more potent than the parent compound, SAHB3$_{BID}$A, in suppressing leukemic growth.

In further animal experiments, leukemic mice (generated as above) were imaged on day 0 and then treated intravenously with 10 mg/kg SAHB3$_{BID}$A, 5 mg/kg SAHB3$_{BID}$A, or vehicle control (5% DMSO in D5W) on days 1, 2, 3, 6, and 7. Total body luminescence was measured on days 4 and 8. Referring to FIG. 27$a$, analysis of tumor burden among the groups demonstrates leukemic suppression by SAHB3$_{BID}$A in a dose-dependent manner compared to untreated control mice. Referring to FIG. 27$b$, total body luminescence images demonstrate more advanced leukemia in the untreated group by day 8 (red density represents high level leukemia) compared to the SAHB3$_{BID}$A-treated mice, whose leukemic progression is noticeably blunted.

In additional animal experiments that instead employed SCID beige mice and RS4; 11 leukemia cells, SAHB3$_{BID}$A treatment consistently suppressed leukemia growth in vivo. For in vivo leukemia imaging, mice were anesthetized with inhaled isoflurane (Abbott Laboratories) and treated concomitantly with intraperitoneal injection of D-luciferin (60 mg/kg) (Promega). Photonic emission was imaged (2 min exposure) using the In Vivo Imaging System (Xenogen) and total body bioluminescence quantified by integration of photonic flux (photons/sec) (Living Image Software, Xenogen). Starting on experimental day 1, mice received a daily tail vein injection of SAHB3$_{BID}$A (10 mg/kg) or vehicle (5% DMSO in D5W) for seven days. Mice were imaged on days 1, 3, and 5 and survival monitored daily for the duration of the experiment. The survival distributions of SAHB3$_{BID}$A and vehicle-treated mice were determined using the Kaplan-Meier method and compared using the log-rank test. The Fisher's Exact test was used to compare the proportion of mice who failed treatment between days 3 and 5, where treatment failure was defined as progression or death, and success as stable disease or regression. Expired mice were subjected to necropsy (Rodent Histopathology Core, DF/HCC).

Control mice demonstrated progressive acceleration of leukemic growth as quantitated by increased bioluminescent flux from days 1-5 (FIG. 27$c$). SAHB3$_{BID}$A treatment suppressed the leukemic expansion after day 3, with tumor regression observed by day 5. Representative mouse images demonstrate the progressive leukemic infiltration of spleen and liver in mice, but regression of disease at these anatomical sites in SAHB$_A$-treated mice by day 5 of treatment (FIG. 27d). The median time to death in this cohort was 5 days for control animals, whereas none of the SAHB$_A$-treated animals dies during the seven day treatment period, and instead survived for a median of 11 days (FIG. 27e). Histologic examination of SAHB$_A$-treated mice showed no obvious toxicity of the compound to normal tissue. In an additional study comparing SAHB3$_{BID}$A- and SAHB3$_{BID(G \to E)}$A-treated mice, animals receiving the point mutant SAHB did not exhibit tumor regression (FIG. 27f), highlighting the in vivo specificity of SAHB3$_{BID}$A's anti-leukemic activity.

Polypeptides

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

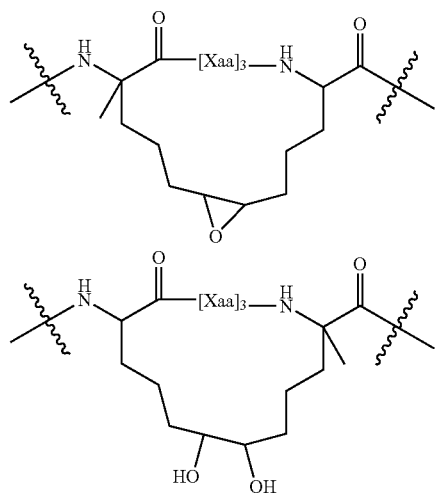

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body (e.g., directing the compound to the thyroid when using an Iodine tag) or track the location of the compound in the body. Alternatively, an additional therapeutic agent can be chemically attached to the functionalized tether (e.g., an anti-cancer agent such as rapamycin, vinblastine, taxol, etc.). Such derivitization can alternatively be achieved by synthetic manipulation of the amino or carboxy terminus of the polypeptide or via the amino acid side chain.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, *Protective Groups in Organic Synthesis*, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W.H. Freeman & Co., New York, N.Y., 1992, p. 77. Hence, peptides can be synthesized using the automated Merrifield techniques of solid phase synthesis with the α-NH$_2$ protected by either t-Boc or F-moc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput polychannel combinatorial synthesizer available from Advanced Chemtech.

FIGS. 28a-28f depict various peptides that include domains that are useful for creating cross-linked peptides.

Methods of Treatment

The present invention provides for both prophylactic and therapeutic methods of treating a subject at risk of (or susceptible to) a disorder or having a disorder associated with aberrant (e.g., insufficient or excessive) BCL-2 family member expression or activity (e.g., extrinsic or intrinsic apoptotic pathway abnormalities). As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

It is possible that some BCL-2 type disorders can be caused, at least in part, by an abnormal level of one or more BCL-2 family members (e.g., over or under expression), or by the presence of one or more BCL-2 family members exhibiting abnormal activity. As such, the reduction in the level and/or activity of the BCL-2 family member or the enhancement of the level and/or activity of the BCL-2 family member, which would bring about the amelioration of disorder symptoms.

The polypeptides of the invention can be used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The compounds (i.e., polypeptides) can act as novel therapeutic agents for controlling breast cancer, ovarian cancer, colon cancer, lung cancer, metastasis of such cancers and the like. A metastatic tumor can arise from a multitude of primary tumor types, including but not limited to those of breast, lung, liver, colon and ovarian origin.

Examples of cancers or neoplastic conditions include, but are not limited to, a fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi sarcoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Preferably, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of cellular proliferative and/or differentiative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, noninflammatory pleural effusions, pneumothorax, and pleural tumors, including solitary fibrous tumors (pleural fibroma) and malignant mesothelioma.

Examples of cellular proliferative and/or differentiative disorders of the colon include, but are not limited to, nonneoplastic polyps, adenomas, familial syndromes, colorectal carcinogenesis, colorectal carcinoma, and carcinoid tumors.

Examples of cellular proliferative and/or differentiative disorders of the liver include, but are not limited to, nodular hyperplasias, adenomas, and malignant tumors, including primary carcinoma of the liver and metastatic tumors.

Examples of cellular proliferative and/or differentiative disorders of the ovary include, but are not limited to, ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosa-theca cell tumors, thecoma-fibromas, androblastomas, hill cell tumors, and gonadoblastoma; and metastatic tumors such as Krukenberg tumors.

The polypeptides described herein can also be used to treat, prevent or diagnose conditions charaterised by overactive cell death or cellular death due to physiologic insult etc. Some examples of conditions characterized by premature or unwanted cell deth are or alternatively unwanted or excessive cellular proliferation include, but are not limited to hypocellular/hypoplastic, acellular/aplastic, or hypercellular/hyperplastic conditions. Some examples include hematologic disorders including but not limited to fanconi anemia, aplastic anemia, thalaessemia, congenital neutropenia, myelodysplasia.

The polypeptides of the invention that act to decrease apoptosis can be used to treat disorders associated with an undesirable level of cell death. Thus, the anti-apoptotic peptides of the invention can be used to treat disorders such as those that lead to cell death associated with viral infection, e.g., infection associated with infection with human immunodeficiency virus (HIV). A wide variety of neurological diseases are characterized by the gradual loss of specific sets of neurons, and the anti-apoptotic peptides of the infection can be used in the treatment of these disorders. Such disorders include Alzheimer's disease, Parkinson's disease, amyotrophic lateral sclerosis (ALS) retinitis pigmentosa, spinal muscular atrophy, and various forms of cerebellar degeneration. The cell loss in these diseases does not induce an inflammatory response, and apoptosis appears to be the mechanism of cell death. In addition, a number of hematologic diseases are associated with a decreased production of blood cells. These disorders include anemia associated with chronic disease, aplastic anemia, chronic neutropenia, and the myelodysplastic syndromes. Disorders of blood cell production, such as myelodysplastic syndrome and some forms of aplastic anemia, are associated with increased apoptotic cell death within the bone marrow. These disorders could result from the activation of genes that promote apoptosis, acquired deficiencies in stromal cells or hematopoietic survival factors, or the direct effects of toxins and mediators of immune responses. Two common disorders associated with cell death are myocardial infarctions and stroke. In both disorders, cells within the central area of ischemia, which is produced in the event of acute loss of blood flow, appear to die rapidly as a result of necrosis. However, outside the central ischemic zone, cells die over a more protracted time period and morphologically appear to die by apoptosis. The anti-apoptotic peptides of the invention can be used to treat all such disorders associated with undesirable cell death.

Some examples of immunologic disorders that can be treated with the polypeptides described herein include but are not limited to organ transplant rejection, arthritis, lupus, IBD, crone's disease, asthma, multiple sclerosis, diabetes etc.

Some examples of neurologic disorders that can be treated with the polypeptides described herein include but are not limited to Alzheimer's Disease, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Adult Onset Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob Disease, Gerstmann Straussler-Scheinker Syndrome, Bovine Spongiform Encephalitis, a Prion-mediated disease, and Huntington's Disease.

Some examples of endocrinologic disorders that can be treated with the polypeptides described herein include but are not limited to diabetes, hypthyroidism, hyopituitarism, hypoparathyroidism, hypogonadism, etc.

Examples of cardiovascular disorders (e.g., inflammatory disorders) that can be treated or prevented with the compounds and methods of the invention include, but are not limited to, atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema and chronic pulmonary disease; or a cardiovascular condition associated with interventional procedures ("procedural vascular trauma"), such as restenosis following angioplasty, placement of a shunt, stent, synthetic or natural excision grafts, indwelling catheter, valve or other implantable devices. Preferred cardiovascular disorders include atherosclerosis, myocardial infarction, aneurism, and stroke.

Pharmaceutical Compositions and Routes of Administration

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof, an additional agent including for example, morphine or codeine; and any pharmaceutically acceptable carrier, adjuvant or vehicle. Alternate compositions of this invention comprise a compound of the formulae described herein or a pharmaceutically acceptable salt thereof, and a pharmaceutically acceptable carrier, adjuvant or vehicle. The compositions delineated herein include the compounds of the formulae delineated herein, as well as additional therapeutic agents if present, in amounts effective for achieving a modulation of disease or disease symptoms, including BCL-2 family member mediated disorders or symptoms thereof.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Screening Assays

The invention provides methods (also referred to herein as "screening assays") for identifying polypeptides which modulate the activity of one or more BCL-2 family proteins or which bind to one or more BCL-2 family proteins (e.g., a polypeptide having at least one BH homology domain).

The binding affinity of polypeptides described herein can be determined using, for example, a titration binding assay. A BCL-2 family polypeptide or polypeptide comprising a BH domain (e.g., BID, BAK, BAX, etc.) can be exposed to varying concentrations of a candidate compound (i.e., polypeptide) (e.g., 1 nM, 10 nM, 100 nM, 1 µM, 10 µM, 100 µM, 1 mM, and 10 mM) in the presence of a substrate such as a fluorescently labeled BH3 containing polypeptide or a fragment thereof (e.g., BID, BAD, BAK, BAX, etc.). The effect of each concentration of candidate compound is then analyzed to determine the effect of the candidate compound on BCL-2 family binding activity at varying concentrations, which can be used to calculate the $K_i$ of the candidate compound. The candidate compound can modulate BCL-2 type activity in a competitive or non-competitive manner. Direct binding assays can also be performed between BCL-2 family proteins and fluorescently labeled candidate compounds to determine the $K_d$ for the binding interaction. Candidate compounds could also be screened for biological activity in vitro, for example, by measuring their dose-responsive efficacy in triggering cytochrome c from purified mitochondria. Cell permeability screening assays are also envisioned, in which fluorescently labeled candidate compounds are applied to intact cells, which are then assayed for cellular fluorescence by microscopy or high-throughput cellular fluorescence detection.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

In one embodiment, an assay is a cell-based assay in which a cell that expresses a BCL-2 family protein or biologically active portion thereof is contacted with a candidate polypeptide, and the ability of the test compound to modulate BCL-2 type activity is determined (e.g., in some instances increase in apoptosis and in other instances decrease apoptosis, via intrinsic or extrinsic cell death pathways). Determining the ability of the test compound to modulate BCL-2 type activity within cells can be accomplished by monitoring, for example, release of cytochrome c from the mitochondria or other relevant physiologic readout (e.g., annexin V staining, MTT assay, caspase activity assay, TUNEL assay).

In one embodiment, an assay is a biochemical assay, whereby crosslinked polypeptides can be linked to affinity resin in order to purify or identify new or known interactive partners in the apoptotic pathway.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

Other Applications

Biologically relevant applications for the peptides described herein are numerous and readily apparent, as indicated by the following cell compartment-based examples:

(1) Cell surface—Natural peptides representing key helical regions of the HIV-1 protein gp41 (e.g. C-peptide, T-20 peptide) have been shown to prevent viral fusion, and therefore, HIV infectivity. Helical peptides participate in fusion mechanisms essential to many virus-host cell infection paradigms (e.g. Dengue, Hepatitis C, Influenza), and therefore, hydrocarbon-stapled analogues of these critical helical regions may function as effective antibiotics by inhibiting viral fusion. In general, ligands that interact with cell surface receptors using helical interfaces to activate or inhibit signaling pathways, represent additional applications for the polypeptides described herein.

(2) Intramembrane—Receptor dimerization and oligomerization are cardinal features of ligand-induced receptor activation and signaling. Transmembrane helical domains widely participate in such essential oligomerization reactions (eg. Epidermal Growth Factor Receptor [EGFR] family), and specific peptide sequences have been defined that facilitate these tight intramembrane helical associations. Aberrant activation of such receptors through oligomerization are implicated in disease pathogenesis (e.g. erbB and cancer). Therefore, in the appropriate setting, activation or inhibition of transmembrane inter-helical interactions would have therapeutic benefit.

(3) Cytosolic—Cytosolic targets include soluble protein targets and those associated with specific intracytosolic organelles, including the mitochondria, endoplasmic reticulum, Golgi network, lysosome, and peroxisome. Within the field of apoptosis, there are multiple cytosolic and mitochondrial apoptotic protein targets for hydrocarbon-stapled BCL-2 family domains. Within the BH3-only subgroup of pro-apoptotic proteins, two major subsets of BH3 domains have been identified: (1) BID-like BH3s (e.g., BIM) which are apoptosis "activators," inducing BAK oligomerization and cytochrome c release at the mitochondrion and (2) BAD-like BH3s which are apoptosis "sensitizers" that selectively target anti-apoptotic multidomain proteins, enabling subliminal levels of activating domains to be maximally effective. In addition to distinct binding of BH3-only proteins to pro- vs. anti-apoptotic multidomain family members, BH3 domains display differential binding among anti-apoptotic proteins. For example, it has been demonstrated that BAD preferentially binds to the anti-apoptotic BCL-2, whereas BIM targets the anti-apoptotic MCL-1. Identifying and exploring these selective interactions are critically important because different BCL-2 family members are implicated in different types of cancer. For example, BCL-2 overexpression is responsible for the development of follicular lymphoma and chemotherapy resistance in general, whereas MCL-1 is believed to play an important role in the pathogenesis of multiple myeloma. The ability to transform the many BH3 domains into structurally stable and cell permeable reagents would provide an important opportunity to explore and differentially manipulate apoptotic pathways in cancer cells. Targeting further helix-dependent interactions in the cytosol or at cytosolic organelles is envisioned.

(4) Nuclear—Nuclear transcription factors and their modulatory proteins drive a host of physiologic processes based upon peptide helical interactions with nuclear proteins and nucleic acids. The feasibility of generating hydrocarbon-stapled peptides to engage in nuclear interactions has recently been demonstrated by our synthesis of a panel of hydrocarbon-stapled p53 peptides, which interact with MDM2 at picomolar affinities. In addition to modulating protein-protein interactions within the nucleus, protein-nucleic acid interactions are also apparent targets. Multiple transcription factor families, such as homeodomain, basic helix-loop-helix, nuclear receptor, and zinc finger-containing proteins, directly interact with DNA via their peptide helices to activate or inhibit gene transcription. As an example, homeodomain proteins are a family of essential transcription factors that regulate genetic programs of growth and differentiation in all multicellular organisms. These proteins share a conserved DNA-binding motif, called the homeodomain, which contains a 60 amino acid long peptide that forms three a-helices, the third of which makes direct contact with the major groove of DNA. Like the BH3 domain of apoptotic proteins, the homeodomain is a critical effector motif with sufficient variation among homologs to facilitate differential binding specificities and physiologic activities. Protein-DNA interactions can be complex and extensive, and thereby present a challenge to small molecule development for the purpose of studying and selectively modulating transcriptional events. In higher organisms, homeodomain proteins are highly expressed during development, specifying the body plan and dictating tissue differentiation. Overexpression of specific homeoproteins (eg. CDX4) can activate tissue-specific differentiation programs resulting in, for example, blood formation from mouse embryonic stem cells. Deregulation of homeotic gene expression, such as aberrant upregulation of homeodomain proteins typically expressed in undifferentiated cells or inappropriate downregulation of such proteins normally expressed in differentiated cells, can contribute to the development and maintenance of cancer. For example, in pediatric alveolar rhabdomyosarcoma, fusion of the PAX3 or PAX 7 DNA binding domain to the transactivating domain of forkhead has been implicated in cellular transformation; translocations involving the DNA-binding domains of several HOX genes have been linked to the pathogenesis of leukemia. Thus, the ability to chemically-stabilize transcription factor helices, such as homeodomain peptides, for cellular delivery has the potential to yield a chemical toolbox for the investigation and modulation of diverse transcription programs responsible for a multitude of biological process in health and disease.

A number of embodiments of the invention have been described. Nevertheless, it will be understood that various modifications may be made without departing from the spirit and scope of the invention. Accordingly, other embodiments are within the scope of the following claims.

What is claimed is:

1. A cross-linked polypeptide comprising an amino acid sequence which is at least 60% identical to an amino acid sequence selected from the group consisting of SEQ ID NO: 92-111, wherein the polypeptide comprises a crosslinker connecting a first amino acid to a second amino acid, and wherein the first and second amino acids are separated by 3 or 6 amino acids.

2. A cross-linked polypeptide comprising an amino acid sequence which is at least 80% identical to an amino acid sequence selected from the group consisting of SEQ ID NO: 92-111 and wherein the cross-linked polypeptide comprises up to 50 amino acids.

3. The cross-linked polypeptide of claim 2, wherein the cross-linked polypeptide comprises an amino acid sequence that is at least 90% identical to an amino acid sequence selected from the group consisting of SEQ ID NO: 92-111 and wherein the cross-linked polypeptide comprises up to 50 amino acids.

4. The cross-linked polypeptide of claim 2, wherein the cross-linked polypeptide comprises an amino acid sequence that is at least 80% identical to SEQ ID NO: 111 and wherein the cross-linked polypeptide comprises up to 50 amino acids.

5. The cross-linked polypeptide of claim 3, wherein the cross-linked polypeptide comprises an amino acid sequence that is at least 90% identical to SEQ ID NO: 111 and wherein the cross-linked polypeptide comprises up to 50 amino acids.

6. The cross-linked polypeptide of claim 5, wherein the cross-linked polypeptide comprises SEQ ID NO: 111.

7. The cross-linked polypeptide of claim 6, wherein the amino acid sequence of the cross-linked polypeptide is IWIAQELR*IGD*FNAYYARR (SEQ ID NO:111) and wherein * is a tethered amino acid.

8. The cross-linked polypeptide of claim 7, wherein an alpha carbon of the tethered amino acid is in an S configuration.

9. The cross-linked polypeptide of claim 8, wherein a tether connecting the alpha carbons of the tethered amino acids contains nine consecutive C—C bonds.

10. The cross-linked polypeptide of claim 1, wherein the polypeptide has the Formula:

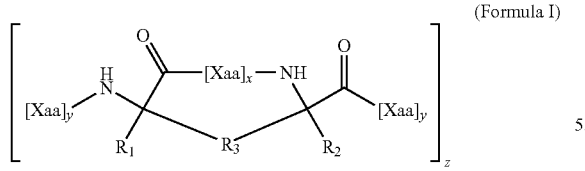

(Formula I)

wherein;

each $R_1$ and $R_2$ are independently H, alkyl, alkenyl, alkynyl, arylalkyl, cycloalkyl, heteroarylalkyl, or heterocyclylalkyl;

$R_3$ is a crosslinker which is alkyl, alkenyl, alkynyl; [$R_4$—K—$R_4$]$_n$, or a naturally occurring amino acid side chain; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

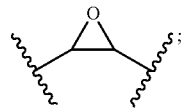

K is O, S, SO, $SO_2$, CO, $CO_2$, $CONR_6$, or $R_6$ is H, alkyl, or a therapeutic agent;

n is an integer from 1-4;

x is 3 or 6;

each y is independently an integer from 1-100;

z is an integer from 1-10; and each Xaa is independently an amino acid.

11. The cross-linked polypeptide of claim 10, wherein the polypeptide has a substantially alpha helical secondary structure in aqueous solution.

12. The cross-linked polypeptide of claim 1, comprising an amino acid sequence which is at least 70% identical to an amino acid sequence selected from the group consisting of SEQ ID NO: 92-111.

13. The cross-linked polypeptide of claim 1, comprising an amino acid sequence which is at least 80% identical to an amino acid sequence selected from the group consisting of SEQ ID NO: 92-111.

14. The cross-linked polypeptide of claim 1, comprising an amino acid sequence which is at least 90% identical to an amino acid sequence selected from the group consisting of SEQ ID NO: 92-111.

15. The cross-linked polypeptide of claim 1, wherein the cross-linked polypeptide comprises up to 50 amino acids.

16. The cross-linked polypeptide of claim 2, 3, 4, or 5, wherein the cross-linked polypeptide comprises a crosslinker connecting a first amino acid to a second amino acid.

17. The cross-linked polypeptide of claim 16, wherein the first and second amino acids are separated by 3 or 6 amino acids.

18. The cross-linked polypeptide of claim 16, wherein the crosslinker is a hydrocarbon crosslinker.

19. The cross-linked polypeptide of claim 1, 2, 3, 4, or 5, wherein the polypeptide has a substantially alpha-helical secondary structure in aqueous solution.

* * * * *

UNITED STATES PATENT AND TRADEMARK OFFICE
CERTIFICATE OF CORRECTION

PATENT NO. : 8,198,405 B2  Page 1 of 1
APPLICATION NO. : 12/182673
DATED : June 12, 2012
INVENTOR(S) : Loren D. Walensky et al.

It is certified that error appears in the above-identified patent and that said Letters Patent is hereby corrected as shown below:

In the claims:

Column 114, line 15, claim 10 please place "K is O, S, SO, SO$_2$, CO, CO$_2$, CONR$_6$, or" before the chemical compound "  "

Signed and Sealed this
Twenty-fourth Day of September, 2013

Teresa Stanek Rea
*Deputy Director of the United States Patent and Trademark Office*

SEQUENCE LISTING

<160> NUMBER OF SEQ ID NOS: 123

<210> SEQ ID NO 1
<211> LENGTH: 193
<212> TYPE: PRT
<213> ORGANISM: Homo sapiens

<400> SEQUENCE: 1

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
            20                  25                  30

Ser Ala Val Ser Cys Gly Leu Cys Ser Pro Gly Leu Ala Ala Ala Pro
        35                  40                  45

Ala Ala Pro Thr Leu Leu Pro Ala Ala Tyr Leu Cys Ala Pro Thr Ala
    50                  55                  60

```
Pro Pro Ala Val Thr Ala Ala Leu Gly Gly Ser Arg Trp Pro Gly Gly
65              70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110

Gly Ala Leu Ala Gly Gly Pro Thr Gln Ala Ala Pro Gly Val Arg Gly
            115                 120                 125

Glu Glu Glu Gln Trp Ala Arg Glu Ile Gly Ala Gln Leu Arg Arg Met
130                 135                 140

Ala Asp Asp Leu Asn Ala Gln Tyr Glu Arg Arg Arg Gln Glu Glu Gln
145                 150                 155                 160

Gln Arg His Arg Pro Ser Pro Trp Arg Val Leu Tyr Asn Leu Ile Met
                165                 170                 175

Gly Leu Leu Pro Leu Pro Arg Gly His Arg Ala Pro Glu Met Glu Pro
            180                 185                 190

Asn
```

<210> SEQ ID NO 2
<211> LENGTH: 193
<212> TYPE: PRT
<213> ORGANISM: Mus musculus

<400> SEQUENCE: 2

```
Met Ala Arg Ala Arg Gln Glu Gly Ser Ser Pro Glu Pro Val Glu Gly
1               5                   10                  15

Leu Ala Arg Asp Ser Pro Arg Pro Phe Pro Leu Gly Arg Leu Met Pro
                20                  25                  30

Ser Ala Val Ser Cys Ser Leu Cys Ser Pro Gly Leu Pro Ala Ala Pro
            35                  40                  45

Ala Ala Pro Ala Leu Leu Pro Ala Ala Tyr Leu Cys Ala Pro Thr Ala
        50                  55                  60

Pro Pro Ala Val Thr Ala Ala Leu Gly Gly Pro Arg Trp Pro Gly Gly
65              70                  75                  80

His Arg Ser Arg Pro Arg Gly Pro Arg Pro Asp Gly Pro Gln Pro Ser
                85                  90                  95

Leu Ser Pro Ala Gln Gln His Leu Glu Ser Pro Val Pro Ser Ala Pro
            100                 105                 110

Glu Ala Leu Ala Gly Gly Pro Thr Gln Ala Ala Pro Gly Val Arg Val
            115                 120                 125

Glu Glu Glu Glu Trp Ala Arg Glu Ile Gly Ala Gln Leu Arg Arg Met
130                 135                 140

Ala Asp Asp Leu Asn Ala Gln Tyr Glu Arg Arg Arg Gln Glu Glu Gln
145                 150                 155                 160

His Arg His Arg Pro Ser Pro Trp Arg Val Met Tyr Asn Leu Phe Met
                165                 170                 175

Gly Leu Leu Pro Leu Pro Arg Gln Pro Gly Ala Pro Glu Met Glu Pro
            180                 185                 190

Asn
```

<210> SEQ ID NO 3
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 3

Trp Ala Arg Glu Ile Gly Ala Gln Leu Arg Arg Met Ala Asp Asp Leu
1               5                   10                  15

Asn Ala Gln Tyr
            20

<210> SEQ ID NO 4
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ile Gly Tyr Glu Ile Gly Ser Lys Leu Ala Ala Met Cys Asp Asp Phe
1               5                   10                  15

Asp Ala Gln Met
            20

<210> SEQ ID NO 5
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ala Ala Gln Arg Tyr Gly Arg Glu Leu Arg Arg Met Ser Asp Glu Phe
1               5                   10                  15

Val Asp Ser Phe
            20

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Pro Glu Ile Trp Ile Ala Gln Glu Leu Arg Arg Ile Gly Asp Glu Phe
1               5                   10                  15

Asn Ala Tyr Tyr
            20

<210> SEQ ID NO 7
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ile Ile Arg Asn Ile Ala Arg His Leu Ala Gln Val Gly Asp Ser Met
1               5                   10                  15

Asp Arg Ser Ile
            20

<210> SEQ ID NO 8

```
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Ser Asp Ala Leu Ala Leu Arg Leu Ala Cys Ile Gly Asp Glu Met
1               5                   10                  15

Asp Val Ser Leu
            20

<210> SEQ ID NO 9
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Ala Gln Leu Thr Ala Ala Arg Leu Lys Ala Leu Gly Asp Glu Leu
1               5                   10                  15

His Gln Arg Thr
            20

<210> SEQ ID NO 10
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Ala Leu Ala Leu Arg Leu Ala Cys Ile Gly Asp Glu Met Asp Val Ser
1               5                   10                  15

Leu Arg

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Trp Ile Ala Gln Glu Leu Arg Arg Ile Gly Asp Glu Phe Asn Ala Tyr
1               5                   10                  15

Tyr Ala

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Glu Cys Ala Thr Gln Leu Arg Arg Phe Gly Asp Lys Leu Asn Phe Arg
1               5                   10                  15

Gln Lys
```

```
<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Asn Ile Ala Arg His Leu Ala Gln Val Gly Asp Ser Met Asp Arg Ser
1               5                   10                  15

Ile Pro

<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Tyr Gly Arg Glu Leu Arg Arg Met Ser Asp Glu Phe Val Asp Ser
1               5                   10                  15

Phe Lys

<210> SEQ ID NO 15
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Glu Ile Gly Ser Lys Leu Ala Ala Met Cys Asp Asp Phe Asp Ala Gln
1               5                   10                  15

Met Met

<210> SEQ ID NO 16
<211> LENGTH: 9
<212> TYPE: PRT
<213> ORGANISM: Homo sapiens

<400> SEQUENCE: 16

Leu Asp Ala Leu Gly His Glu Leu Pro
1               5

<210> SEQ ID NO 17
<211> LENGTH: 9
<212> TYPE: PRT
<213> ORGANISM: Mus musculus

<400> SEQUENCE: 17

Leu Glu Val Leu Gly Arg Glu Leu Pro
1               5

<210> SEQ ID NO 18
<211> LENGTH: 9
<212> TYPE: PRT
<213> ORGANISM: Homo sapiens

<400> SEQUENCE: 18

Leu Ala Gln Val Gly Asp Ser Met Asp
1               5
```

```
<210> SEQ ID NO 19
<211> LENGTH: 9
<212> TYPE: PRT
<213> ORGANISM: Mus musculus

<400> SEQUENCE: 19

Leu Ala Gln Ile Gly Asp Glu Met Asp
1               5

<210> SEQ ID NO 20
<211> LENGTH: 9
<212> TYPE: PRT
<213> ORGANISM: Homo sapiens

<400> SEQUENCE: 20

Leu Ala Cys Ile Gly Asp Glu Met Asp
1               5

<210> SEQ ID NO 21
<211> LENGTH: 9
<212> TYPE: PRT
<213> ORGANISM: Homo sapiens

<400> SEQUENCE: 21

Leu Arg Arg Ile Gly Asp Glu Phe Asn
1               5

<210> SEQ ID NO 22
<211> LENGTH: 9
<212> TYPE: PRT
<213> ORGANISM: Homo sapiens

<400> SEQUENCE: 22

Leu Lys Ala Leu Gly Asp Glu Leu His
1               5

<210> SEQ ID NO 23
<211> LENGTH: 9
<212> TYPE: PRT
<213> ORGANISM: Homo sapiens

<400> SEQUENCE: 23

Leu Arg Arg Met Ser Asp Glu Phe Val
1               5

<210> SEQ ID NO 24
<211> LENGTH: 9
<212> TYPE: PRT
<213> ORGANISM: Homo sapiens

<400> SEQUENCE: 24

Leu Ala Ile Ile Gly Asp Asp Ile Asn
1               5

<210> SEQ ID NO 25
<211> LENGTH: 9
<212> TYPE: PRT
<213> ORGANISM: Homo sapiens

<400> SEQUENCE: 25

Leu Lys Arg Ile Gly Asp Glu Leu Asp
1               5

<210> SEQ ID NO 26
```

```
<211> LENGTH: 9
<212> TYPE: PRT
<213> ORGANISM: Mus musculus

<400> SEQUENCE: 26

Leu Leu Arg Leu Gly Asp Glu Leu Glu
1               5

<210> SEQ ID NO 27
<211> LENGTH: 351
<212> TYPE: PRT
<213> ORGANISM: Homo sapiens

<400> SEQUENCE: 27

Met Thr Leu Arg Leu Leu Glu Asp Trp Cys Arg Gly Met Asp Met Asn
1               5                   10                  15

Pro Arg Lys Ala Leu Leu Ile Ala Gly Ile Ser Gln Ser Cys Ser Val
                20                  25                  30

Ala Glu Ile Glu Glu Ala Leu Gln Ala Gly Leu Ala Pro Leu Gly Glu
            35                  40                  45

Tyr Arg Leu Leu Gly Arg Met Phe Arg Arg Asp Glu Asn Arg Lys Val
    50                  55                  60

Ala Leu Val Gly Leu Thr Ala Glu Thr Ser His Ala Leu Val Pro Lys
65                  70                  75                  80

Glu Ile Pro Gly Lys Gly Ile Trp Arg Val Ile Phe Lys Pro Pro
                85                  90                  95

Asp Pro Asp Asn Thr Phe Leu Ser Arg Leu Asn Glu Phe Leu Ala Gly
                100                 105                 110

Glu Gly Met Thr Val Gly Glu Leu Ser Arg Ala Leu Gly His Glu Asn
            115                 120                 125

Gly Ser Leu Asp Pro Glu Gln Gly Met Ile Pro Glu Met Trp Ala Pro
        130                 135                 140

Met Leu Ala Gln Ala Leu Glu Ala Leu Gln Pro Ala Leu Gln Cys Leu
145                 150                 155                 160

Lys Tyr Lys Lys Leu Arg Val Phe Ser Gly Arg Ile Ser Pro Glu Pro
                165                 170                 175

Gly Glu Glu Glu Phe Gly Arg Trp Met Phe His Thr Thr Gln Met Ile
                180                 185                 190

Lys Ala Trp Gln Val Pro Asp Val Glu Lys Arg Arg Arg Leu Leu Glu
            195                 200                 205

Ser Leu Arg Gly Pro Ala Leu Asp Val Ile Arg Val Leu Lys Ile Asn
    210                 215                 220

Asn Pro Leu Ile Thr Val Asp Glu Cys Leu Gln Ala Leu Glu Glu Val
225                 230                 235                 240

Phe Gly Val Thr Asp Asn Pro Arg Glu Leu Gln Val Lys Tyr Leu Thr
                245                 250                 255

Thr Tyr His Lys Asp Glu Glu Lys Leu Ser Ala Tyr Val Leu Arg Leu
                260                 265                 270

Glu Pro Leu Leu Gln Lys Leu Val Gln Arg Gly Ala Ile Glu Arg Asp
            275                 280                 285

Ala Val Asn Gln Ala Arg Leu Asp Gln Val Ile Ala Gly Ala Val His
        290                 295                 300

Lys Thr Ile Arg Arg Glu Leu Asn Leu Pro Glu Asp Gly Pro Ala Pro
305                 310                 315                 320

Gly Phe Leu Gln Leu Leu Val Leu Ile Lys Asp Tyr Glu Ala Ala Glu
                325                 330                 335
```

Glu Glu Glu Ala Leu Leu Gln Ala Ile Leu Glu Gly Asn Phe Thr
            340                 345                 350

<210> SEQ ID NO 28
<211> LENGTH: 352
<212> TYPE: PRT
<213> ORGANISM: Mus musculus

<400> SEQUENCE: 28

Met Thr Leu Arg Leu Leu Glu Asp Trp Cys Arg Gly Met Asp Met Asn
1               5                   10                  15

Pro Arg Lys Ala Leu Leu Val Ala Gly Ile Pro Pro Thr Cys Gly Val
            20                  25                  30

Ala Asp Ile Glu Glu Ala Leu Gln Ala Gly Leu Ala Pro Leu Gly Glu
        35                  40                  45

His Arg Leu Leu Gly Arg Met Phe Arg Arg Asp Glu Asn Lys Asn Val
    50                  55                  60

Ala Leu Ile Gly Leu Thr Val Glu Thr Gly Ser Ala Leu Val Pro Lys
65                  70                  75                  80

Glu Ile Pro Ala Lys Gly Gly Val Trp Arg Val Ile Phe Lys Pro Pro
                85                  90                  95

Asp Thr Asp Ser Asp Phe Leu Cys Arg Leu Asn Glu Phe Leu Lys Gly
            100                 105                 110

Glu Gly Met Thr Met Gly Glu Leu Thr Arg Val Leu Gly Asn Arg Asn
        115                 120                 125

Asp Pro Leu Gly Leu Asp Pro Gly Ile Met Ile Pro Glu Ile Arg Ala
    130                 135                 140

Pro Met Leu Ala Gln Ala Leu Asn Glu Ala Leu Lys Pro Thr Leu Gln
145                 150                 155                 160

Tyr Leu Arg Tyr Lys Lys Leu Ser Val Phe Ser Gly Arg Asp Pro Pro
                165                 170                 175

Gly Pro Gly Glu Glu Glu Phe Glu Ser Trp Met Phe His Thr Ser Gln
            180                 185                 190

Val Met Lys Thr Trp Gln Val Ser Asp Val Glu Lys Arg Arg Arg Leu
        195                 200                 205

Ile Glu Ser Leu Arg Gly Pro Ala Phe Glu Ile Ile Arg Val Leu Lys
    210                 215                 220

Ile Asn Asn Pro Phe Ile Thr Val Ala Glu Cys Leu Lys Thr Leu Glu
225                 230                 235                 240

Thr Ile Phe Gly Ile Ile Asp Asn Pro Arg Ala Leu Gln Val Lys Tyr
                245                 250                 255

Leu Thr Thr Tyr Gln Lys Thr Asp Glu Lys Leu Ser Ala Tyr Val Leu
            260                 265                 270

Arg Leu Glu Pro Leu Leu Gln Lys Leu Val Gln Lys Gly Ala Ile Glu
        275                 280                 285

Lys Glu Val Val Asn Gln Ala Arg Leu Asp Gln Val Ile Ala Gly Ala
    290                 295                 300

Val His Lys Ser Val Arg Arg Glu Leu Gly Leu Pro Glu Gly Ser Pro
305                 310                 315                 320

Ala Pro Gly Leu Leu Gln Leu Leu Thr Leu Ile Lys Asp Lys Glu Ala
                325                 330                 335

Glu Glu Glu Glu Val Leu Leu Gln Ala Glu Leu Glu Gly Tyr Cys Thr
            340                 345                 350

<210> SEQ ID NO 29
<211> LENGTH: 329

```
<212> TYPE: PRT
<213> ORGANISM: Homo sapiens

<400> SEQUENCE: 29

Met Ala Met Thr Leu Leu Glu Asp Trp Cys Arg Gly Met Asp Val Asn
1               5                   10                  15

Ser Gln Arg Ala Leu Leu Val Trp Gly Ile Pro Val Asn Cys Asp Glu
            20                  25                  30

Ala Glu Ile Glu Glu Thr Leu Gln Ala Ala Met Pro Gln Val Ser Tyr
        35                  40                  45

Arg Met Leu Gly Arg Met Phe Trp Arg Glu Glu Asn Ala Lys Ala Ala
    50                  55                  60

Leu Leu Glu Leu Thr Gly Ala Val Asp Tyr Ala Ala Ile Pro Arg Glu
65                  70                  75                  80

Met Pro Gly Lys Gly Gly Val Trp Lys Val Leu Phe Lys Pro Pro Thr
                85                  90                  95

Ser Asp Ala Glu Phe Leu Glu Arg Leu His Leu Phe Leu Ala Arg Glu
            100                 105                 110

Gly Trp Thr Val Gln Asp Val Ala Arg Val Leu Gly Phe Gln Asn Pro
        115                 120                 125

Thr Pro Thr Pro Gly Pro Glu Met Pro Ala Glu Met Leu Asn Tyr Ile
    130                 135                 140

Leu Asp Asn Val Ile Gln Pro Leu Val Glu Ser Ile Trp Tyr Lys Arg
145                 150                 155                 160

Leu Thr Leu Phe Ser Gly Lys Gly His Pro Arg Ala Trp Arg Gly Asn
                165                 170                 175

Phe Asp Pro Trp Leu Glu His Thr Met Glu Val Leu Glu Glu Trp Gln
            180                 185                 190

Val Ser Asp Val Glu Lys Arg Arg Arg Leu Met Glu Ser Leu Arg Gly
        195                 200                 205

Pro Ala Ala Asp Val Ile Arg Ile Leu Lys Ser Asn Asn Pro Ala Ile
    210                 215                 220

Thr Thr Ala Glu Cys Leu Lys Ala Leu Glu Gln Val Phe Gly Ser Val
225                 230                 235                 240

Glu Ser Ser Arg Asp Ala Gln Ile Lys Phe Leu Asn Thr Tyr Gln Asn
                245                 250                 255

Pro Gly Glu Lys Leu Ser Ala Tyr Val Ile Arg Leu Glu Pro Leu Leu
            260                 265                 270

Gln Lys Val Val Glu Lys Gly Ala Ile Asp Lys Asp Asn Val Asn Gln
        275                 280                 285

Ala Arg Leu Glu Gln Val Ile Ala Gly Ala Asn His Ser Gly Ala Ile
    290                 295                 300

Arg Arg Gln Leu Trp Leu Thr Gly Ala Gly Glu Gly Pro Gly Pro Lys
305                 310                 315                 320

Pro Leu Ser Val Ala Gly Ala Asp Pro
                325

<210> SEQ ID NO 30
<211> LENGTH: 364
<212> TYPE: PRT
<213> ORGANISM: Homo sapiens

<400> SEQUENCE: 30

Met Ala Leu Ala Leu Leu Glu Asp Trp Cys Arg Ile Met Ser Val Asp
1               5                   10                  15

Glu Gln Lys Ser Leu Met Val Thr Gly Ile Pro Ala Asp Phe Glu Glu
```

```
            20                  25                  30
Ala Glu Ile Gln Glu Val Leu Gln Thr Leu Lys Ser Leu Gly Arg
        35                  40                  45

Tyr Arg Leu Leu Gly Lys Ile Phe Arg Arg Gln Glu Asn Ala Asn Ala
    50                  55                  60

Val Leu Leu Glu Leu Leu Glu Asp Thr Asp Val Ser Ala Ile Pro Ser
65                  70                  75                  80

Glu Val Gln Gly Lys Gly Gly Val Trp Lys Val Ile Phe Lys Thr Pro
                85                  90                  95

Asn Gln Asp Thr Glu Phe Leu Glu Arg Leu Asn Leu Phe Leu Glu Lys
            100                 105                 110

Glu Gly Gln Thr Val Ser Gly Met Phe Arg Ala Leu Gly Gln Glu Gly
        115                 120                 125

Val Ser Pro Ala Thr Val Pro Cys Ile Ser Pro Glu Leu Leu Ala His
    130                 135                 140

Leu Leu Gly Gln Ala Met Ala His Ala Pro Gln Pro Leu Leu Pro Met
145                 150                 155                 160

Arg Tyr Arg Lys Leu Arg Val Phe Ser Gly Ser Ala Val Pro Ala Pro
                165                 170                 175

Glu Glu Glu Ser Phe Glu Val Trp Leu Glu Gln Ala Thr Glu Ile Val
            180                 185                 190

Lys Glu Trp Pro Val Thr Glu Ala Glu Lys Lys Arg Trp Leu Ala Glu
        195                 200                 205

Ser Leu Arg Gly Pro Ala Leu Asp Leu Met His Ile Val Gln Ala Asp
    210                 215                 220

Asn Pro Ser Ile Ser Val Glu Glu Cys Leu Glu Ala Phe Lys Gln Val
225                 230                 235                 240

Phe Gly Ser Leu Glu Ser Arg Arg Thr Ala Gln Val Arg Tyr Leu Lys
                245                 250                 255

Thr Tyr Gln Glu Glu Gly Glu Lys Val Ser Ala Tyr Val Leu Arg Leu
            260                 265                 270

Glu Thr Leu Leu Arg Arg Ala Val Glu Lys Arg Ala Ile Pro Arg Arg
        275                 280                 285

Ile Ala Asp Gln Val Arg Leu Glu Gln Val Met Ala Gly Ala Thr Leu
    290                 295                 300

Asn Gln Met Leu Trp Cys Arg Leu Arg Glu Leu Lys Asp Gln Gly Pro
305                 310                 315                 320

Pro Pro Ser Phe Leu Glu Leu Met Lys Val Ile Arg Glu Glu Glu Glu
                325                 330                 335

Glu Glu Ala Ser Phe Glu Asn Glu Ser Ile Glu Glu Pro Glu Glu Arg
            340                 345                 350

Asp Gly Tyr Gly Arg Trp Asn His Glu Gly Asp Asp
        355                 360

<210> SEQ ID NO 31
<211> LENGTH: 8
<212> TYPE: PRT
<213> ORGANISM: Homo sapiens

<400> SEQUENCE: 31

Leu Ser Arg Ala Leu Gly His Glu
1               5

<210> SEQ ID NO 32
<211> LENGTH: 8
<212> TYPE: PRT
```

<213> ORGANISM: Mus musculus

<400> SEQUENCE: 32

Leu Thr Arg Val Leu Gly Asn Arg
1               5

<210> SEQ ID NO 33
<211> LENGTH: 7
<212> TYPE: PRT
<213> ORGANISM: Homo sapiens

<400> SEQUENCE: 33

Leu Asp Ala Leu Gly His Glu
1               5

<210> SEQ ID NO 34
<211> LENGTH: 7
<212> TYPE: PRT
<213> ORGANISM: Mus musculus

<400> SEQUENCE: 34

Leu Glu Val Leu Gly Arg Glu
1               5

<210> SEQ ID NO 35
<211> LENGTH: 7
<212> TYPE: PRT
<213> ORGANISM: Homo sapiens

<400> SEQUENCE: 35

Leu Lys Ala Leu Gly Asp Glu
1               5

<210> SEQ ID NO 36
<211> LENGTH: 7
<212> TYPE: PRT
<213> ORGANISM: Homo sapiens

<400> SEQUENCE: 36

Leu Ala Gln Val Gly Asp Ser
1               5

<210> SEQ ID NO 37
<211> LENGTH: 7
<212> TYPE: PRT
<213> ORGANISM: Homo sapiens

<400> SEQUENCE: 37

Leu Lys Arg Ile Gly Asp Glu
1               5

<210> SEQ ID NO 38
<211> LENGTH: 7
<212> TYPE: PRT
<213> ORGANISM: Homo sapiens

<400> SEQUENCE: 38

Leu Arg Arg Ile Gly Asp Glu
1               5

<210> SEQ ID NO 39
<211> LENGTH: 7
<212> TYPE: PRT
<213> ORGANISM: Homo sapiens

<400> SEQUENCE: 39

```
Leu Ala Gln Ile Gly Asp Glu
1               5

<210> SEQ ID NO 40
<211> LENGTH: 213
<212> TYPE: PRT
<213> ORGANISM: Rattus norvegicus

<400> SEQUENCE: 40

Met Glu Val Leu Arg Ser Ser Val Phe Ala Ala Glu Ile Met Asp
1               5                   10                  15

Ala Phe Asp Arg Ser Pro Thr Asp Lys Glu Leu Val Ala Gln Ala Lys
                20                  25                  30

Ala Leu Gly Arg Glu Tyr Val His Ala Arg Leu Leu Arg Ala Gly Leu
            35                  40                  45

Ser Trp Ser Ala Pro Glu Arg Ala Ser Pro Ala Pro Gly Gly Arg Leu
        50                  55                  60

Ala Glu Val Cys Thr Val Leu Leu Arg Leu Gly Asp Glu Leu Glu Gln
65                  70                  75                  80

Ile Arg Pro Ser Val Tyr Arg Asn Val Ala Arg Gln Leu His Ile Pro
                85                  90                  95

Leu Gln Ser Glu Pro Val Val Thr Asp Ala Phe Leu Ala Val Ala Gly
                100                 105                 110

His Ile Phe Ser Ala Gly Ile Thr Trp Gly Lys Val Val Ser Leu Tyr
            115                 120                 125

Ser Val Ala Ala Gly Leu Ala Val Asp Cys Val Arg Gln Ala Gln Pro
        130                 135                 140

Ala Met Val His Ala Leu Val Asp Cys Leu Gly Glu Phe Val Arg Lys
145                 150                 155                 160

Thr Leu Ala Thr Trp Leu Arg Arg Gly Gly Trp Thr Asp Val Leu
                165                 170                 175

Lys Cys Val Val Ser Thr Asp Pro Gly Phe Arg Ser His Trp Leu Val
                180                 185                 190

Ala Thr Leu Cys Ser Phe Gly Arg Phe Leu Lys Ala Ala Phe Phe Leu
            195                 200                 205

Leu Leu Pro Glu Arg
        210

<210> SEQ ID NO 41
<211> LENGTH: 211
<212> TYPE: PRT
<213> ORGANISM: Homo sapiens

<400> SEQUENCE: 41

Met Ala Ser Gly Gln Gly Pro Gly Pro Pro Arg Gln Glu Cys Gly Glu
1               5                   10                  15

Pro Ala Leu Pro Ser Ala Ser Glu Glu Gln Val Ala Gln Asp Thr Glu
                20                  25                  30

Glu Val Phe Arg Ser Tyr Val Phe Tyr Arg His Gln Gln Glu Gln Glu
            35                  40                  45

Ala Glu Gly Val Ala Ala Pro Ala Asp Pro Glu Met Val Thr Leu Pro
        50                  55                  60

Leu Gln Pro Ser Ser Thr Met Gly Gln Val Gly Arg Gln Leu Ala Ile
65                  70                  75                  80

Ile Gly Asp Asp Ile Asn Arg Arg Tyr Asp Ser Glu Phe Gln Thr Met
                85                  90                  95
```

```
Leu Gln His Leu Gln Pro Thr Ala Glu Asn Ala Tyr Glu Tyr Phe Thr
                100                 105                 110

Lys Ile Ala Thr Ser Leu Phe Glu Ser Gly Ile Asn Trp Gly Arg Val
            115                 120                 125

Val Ala Leu Leu Gly Phe Gly Tyr Arg Leu Ala Leu His Val Tyr Gln
        130                 135                 140

His Gly Leu Thr Gly Phe Leu Gly Gln Val Thr Arg Phe Val Val Asp
145                 150                 155                 160

Phe Met Leu His His Cys Ile Ala Arg Trp Ile Ala Gln Arg Gly Gly
                165                 170                 175

Trp Val Ala Ala Leu Asn Leu Gly Asn Gly Pro Ile Leu Asn Val Leu
            180                 185                 190

Val Val Leu Gly Val Val Leu Leu Gly Gln Phe Val Val Arg Arg Phe
        195                 200                 205

Phe Lys Ser
    210

<210> SEQ ID NO 42
<211> LENGTH: 192
<212> TYPE: PRT
<213> ORGANISM: Bos taurus

<400> SEQUENCE: 42

Met Asp Gly Ser Gly Glu Gln Pro Arg Gly Gly Gly Pro Thr Ser Ser
1               5                   10                  15

Glu Gln Ile Met Lys Thr Gly Ala Leu Leu Leu Gln Gly Phe Ile Gln
            20                  25                  30

Asp Arg Ala Gly Arg Met Gly Gly Glu Ala Pro Glu Leu Ala Leu Asp
        35                  40                  45

Pro Val Pro Gln Asp Ala Ser Thr Lys Lys Leu Ser Glu Cys Leu Lys
    50                  55                  60

Arg Ile Gly Asp Glu Leu Asp Ser Asn Met Glu Leu Gln Arg Met Ile
65                  70                  75                  80

Ala Ala Val Asp Thr Asp Ser Pro Arg Glu Val Phe Phe Arg Val Ala
                85                  90                  95

Ala Asp Met Phe Ser Asp Gly Asn Phe Asn Trp Gly Arg Val Val Ala
            100                 105                 110

Leu Phe Tyr Phe Ala Ser Lys Leu Val Leu Lys Ala Leu Cys Thr Lys
        115                 120                 125

Val Pro Glu Leu Ile Arg Thr Ile Met Gly Trp Thr Leu Asp Phe Leu
    130                 135                 140

Arg Glu Arg Leu Leu Gly Trp Ile Gln Asp Gln Gly Gly Trp Asp Gly
145                 150                 155                 160

Leu Leu Ser Tyr Phe Gly Thr Pro Thr Trp Gln Thr Val Thr Ile Phe
                165                 170                 175

Val Ala Gly Val Leu Thr Ala Ser Leu Thr Ile Trp Lys Lys Met Gly
            180                 185                 190

<210> SEQ ID NO 43
<211> LENGTH: 193
<212> TYPE: PRT
<213> ORGANISM: Rattus norvegicus

<400> SEQUENCE: 43

Met Ala Thr Pro Ala Ser Ala Pro Asp Thr Arg Ala Leu Val Ala Asp
1               5                   10                  15

Phe Val Gly Tyr Lys Leu Arg Gln Lys Gly Tyr Val Cys Gly Ala Gly
```

```
            20                  25                  30
Pro Gly Glu Gly Pro Ala Ala Asp Pro Leu His Gln Ala Met Arg Ala
            35                  40                  45

Ala Gly Asp Glu Phe Glu Thr Arg Phe Arg Arg Thr Phe Ser Asp Leu
 50                  55                  60

Ala Ala Gln Leu His Val Thr Pro Gly Ser Ala Gln Arg Phe Thr
 65                  70                  75                  80

Gln Val Ser Asp Glu Leu Phe Gln Gly Gly Pro Asn Trp Gly Arg Leu
                85                  90                  95

Val Ala Phe Phe Val Phe Gly Ala Ala Leu Cys Ala Glu Ser Val Asn
            100                 105                 110

Lys Glu Met Glu Pro Leu Val Gly Gln Val Gln Glu Trp Met Val Ala
            115                 120                 125

Tyr Leu Glu Thr Arg Leu Ala Asp Trp Ile His Ser Ser Gly Gly Trp
            130                 135                 140

Ala Glu Phe Thr Ala Leu Tyr Gly Asp Gly Ala Leu Glu Glu Ala Arg
145                 150                 155                 160

Arg Leu Arg Glu Gly Asn Trp Ala Ser Val Arg Thr Val Leu Thr Gly
                165                 170                 175

Ala Val Ala Leu Gly Ala Leu Val Thr Val Gly Ala Phe Phe Ala Ser
            180                 185                 190

Lys

<210> SEQ ID NO 44
<211> LENGTH: 194
<212> TYPE: PRT
<213> ORGANISM: Homo sapiens

<400> SEQUENCE: 44

Met Ser Gln Ser Asn Arg Glu Leu Val Val Asp Phe Leu Ser Tyr Lys
 1               5                  10                  15

Leu Ser Gln Lys Gly Tyr Ser Trp Ser Gln Phe Ser Asp Val Glu Glu
                20                  25                  30

Asn Arg Thr Glu Ala Pro Arg Glu Val Ile Pro Met Ala Ala Val Lys
            35                  40                  45

Gln Ala Leu Arg Glu Ala Gly Asp Glu Phe Glu Leu Arg Tyr Arg Arg
 50                  55                  60

Ala Phe Ser Asp Leu Thr Ser Gln Leu His Ile Thr Pro Gly Thr Ala
 65                  70                  75                  80

Tyr Gln Ser Phe Glu Gln Val Val Asn Glu Leu Phe Arg Asp Gly Val
                85                  90                  95

Asn Trp Gly Arg Ile Val Ala Phe Phe Ser Phe Gly Gly Ala Leu Cys
            100                 105                 110

Val Glu Ser Val Asp Lys Glu Met Gln Val Leu Val Ser Arg Ile Ala
            115                 120                 125

Ala Trp Met Ala Thr Tyr Leu Asn Asp His Leu Glu Pro Trp Ile Gln
            130                 135                 140

Glu Asn Gly Gly Trp Asp Thr Phe Val Glu Leu Tyr Gly Asn Asn Ala
145                 150                 155                 160

Ala Ala Glu Ser Arg Lys Gly Gln Glu Arg Phe Asn Arg Trp Phe Leu
                165                 170                 175

Thr Gly Met Thr Val Ala Gly Val Val Leu Leu Gly Ser Leu Phe Ser
            180                 185                 190

Arg Lys
```

<210> SEQ ID NO 45
<211> LENGTH: 200
<212> TYPE: PRT
<213> ORGANISM: Homo sapiens

<400> SEQUENCE: 45

```
Met Ala His Ala Gly Arg Thr Gly Tyr Asp Asn Arg Glu Ile Val Met
1               5                   10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Leu Ser
        35                  40                  45

Pro Val Pro Pro Val Val His Leu Ala Leu Arg Gln Ala Gly Asp Asp
    50                  55                  60

Phe Ser Arg Arg Tyr Arg Gly Asp Phe Ala Glu Met Ser Ser Gln Leu
65                  70                  75                  80

His Leu Thr Pro Phe Thr Ala Arg Gly Arg Phe Ala Thr Val Val Glu
            85                  90                  95

Glu Leu Phe Arg Asp Gly Val Asn Trp Gly Arg Ile Val Ala Phe Phe
            100                 105                 110

Glu Phe Gly Gly Val Met Cys Val Glu Ser Val Asn Arg Glu Met Ser
        115                 120                 125

Pro Leu Val Asp Asn Ile Ala Leu Trp Met Thr Glu Tyr Leu Asn Arg
    130                 135                 140

His Leu His Thr Trp Ile Gln Asp Asn Gly Gly Trp Asp Ala Phe Val
145                 150                 155                 160

Glu Leu Tyr Gly Pro Ser Met Arg Pro Leu Phe Asp Phe Ser Trp Leu
            165                 170                 175

Ser Leu Lys Thr Leu Leu Ser Leu Ala Leu Val Gly Ala Cys Ile Thr
            180                 185                 190

Leu Gly Ala Tyr Leu Ser His Lys
        195                 200
```

<210> SEQ ID NO 46
<211> LENGTH: 231
<212> TYPE: PRT
<213> ORGANISM: Caenorhabditis elegans

<400> SEQUENCE: 46

```
Ser Pro Ser Arg Gln Ala Ser Thr Arg Arg Met Ser Ile Gly Glu Ser
1               5                   10                  15

Ile Asp Gly Lys Ile Asn Asp Trp Glu Glu Pro Arg Leu Asp Ile Glu
            20                  25                  30

Gly Phe Val Val Asp Tyr Phe Thr His Arg Ile Arg Gln Asn Gly Met
        35                  40                  45

Glu Trp Phe Gly Ala Pro Gly Leu Pro Cys Gly Val Gln Pro Glu His
    50                  55                  60

Glu Met Met Arg Val Met Gly Thr Ile Phe Glu Lys Lys His Ala Glu
65                  70                  75                  80

Asn Phe Glu Thr Phe Cys Glu Gln Leu Leu Ala Val Pro Arg Ile Ser
            85                  90                  95

Phe Ser Leu Tyr Gln Asp Val Val Arg Thr Val Gly Asn Ala Gln Thr
            100                 105                 110

Asp Gln Cys Pro Met Ser Tyr Gly Arg Leu Ile Gly Leu Ile Ser Phe
        115                 120                 125

Gly Gly Phe Val Ala Ala Lys Met Met Glu Ser Val Glu Leu Gln Gly
```

```
                130                 135                 140
Gln Val Arg Asn Leu Phe Val Tyr Thr Ser Leu Phe Ile Lys Thr Arg
145                 150                 155                 160

Ile Arg Asn Asn Trp Lys Glu His Asn Arg Ser Trp Asp Asp Phe Met
                165                 170                 175

Thr Leu Gly Lys Gln Met Lys Glu Asp Tyr Glu Arg Ala Glu Ala Glu
                180                 185                 190

Lys Val Gly Arg Arg Lys Gln Asn Arg Arg Trp Ser Met Ile Gly Ala
                195                 200                 205

Gly Val Thr Ala Gly Ala Ile Gly Ile Val Gly Val Val Val Cys Gly
                210                 215                 220

Arg Met Met Phe Ser Leu Lys
225                 230

<210> SEQ ID NO 47
<211> LENGTH: 270
<212> TYPE: PRT
<213> ORGANISM: Artificial Sequence
<220> FEATURE:
<223> OTHER INFORMATION: Description of Artificial Sequence: Synthetic
      Consensus sequence
<220> FEATURE:
<221> NAME/KEY: MOD_RES
<222> LOCATION: (77)..(77)
<223> OTHER INFORMATION: Any amino acid
<220> FEATURE:
<221> NAME/KEY: MOD_RES
<222> LOCATION: (114)..(114)
<223> OTHER INFORMATION: Any amino acid
<220> FEATURE:
<221> NAME/KEY: MOD_RES
<222> LOCATION: (123)..(123)
<223> OTHER INFORMATION: Any amino acid
<220> FEATURE:
<221> NAME/KEY: MOD_RES
<222> LOCATION: (168)..(168)
<223> OTHER INFORMATION: Any amino acid
<220> FEATURE:
<221> NAME/KEY: MOD_RES
<222> LOCATION: (221)..(221)
<223> OTHER INFORMATION: Any amino acid

<400> SEQUENCE: 47

Met Ala Ala Pro Gln Asp Val Asn Val Arg Ile Cys Asn Gln Glx Ile
1               5                   10                  15

Val Lys Phe Asp Leu Glu Val Lys Ala Leu Ile Gln Asp Ile Arg Asp
                20                  25                  30

Cys Ser Gly Pro Leu Ser Ala Leu Thr Glu Leu Asn Thr Lys Val Lys
            35                  40                  45

Glu Lys Phe Gln Gln Leu Arg His Arg Ile Gln Pro Val Leu Tyr Gln
        50                  55                  60

Arg Ala Thr Ile Asn Glx Ala Ser Thr Ile Thr Thr Xaa Leu Tyr Tyr
65                  70                  75                  80

Glu Leu Thr Asp Phe Ser Ser Thr Gln Asn Asp Phe Asn Ser Pro Thr
                85                  90                  95

Tyr Phe Val Thr Phe Ser Asp Leu Glx Gln Leu Ala Lys Glx Gln Asp
                100                 105                 110

Lys Xaa Ser Glu Lys Gln Leu Leu Leu Gln Xaa Val Glu Asn Arg Lys
            115                 120                 125

Lys Gln Asn Leu Lys Asn Gln Ala Ser Trp Arg Lys Ala Asn Leu Thr
        130                 135                 140

Cys Lys Leu Ala Ile Asp Asn Ile Arg Lys Ala Asn Leu Leu Gln Gln
145                 150                 155                 160
```

```
Gln Asp Leu Leu Ala Gln Arg Xaa Thr Tyr Lys Lys Ser Leu Ala Gln
            165                 170                 175

Tyr Ser Ser Thr Ile Thr Lys Ser Leu Asn Gly Ile Ser Arg Gln Lys
        180                 185                 190

Ala Gln Gln Val Gln Gln Ser Glu Glu Ala Asn Gln Ser Leu Val Thr
    195                 200                 205

Ser Ser Arg Thr Ile Leu Asp Ala Lys Glu Glu Thr Xaa Ser Asn Ser
210                 215                 220

Gln Thr Ile Gln Leu Gln Arg Lys Leu Ile Thr Lys Tyr Met Arg Arg
225                 230                 235                 240

Glx Leu Thr Asp Lys Leu Leu Ile Phe Leu Ala Leu Arg Leu Thr Leu
                245                 250                 255

Ala Thr Val Leu Tyr Ile Val Lys Lys Arg Leu Phe Pro Phe
            260                 265                 270

<210> SEQ ID NO 48
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Lys Ala Glu Leu Leu Gln Gly Gly Asp Lys Lys Arg Gln Arg
1               5                   10

<210> SEQ ID NO 49
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Ala Leu Arg Leu Ala Cys Ile Gly Asp Glu Met Asp Val Ser
1               5                   10

<210> SEQ ID NO 50
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Ala Leu Arg Leu Ala Cys Ile Gly Asp Glu Met Asp Leu Cys
1               5                   10

<210> SEQ ID NO 51
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ala Arg His Leu Ala Gln Val Gly Asp Ser Met Asp Arg Ser
1               5                   10

<210> SEQ ID NO 52
```

```
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gly Arg Gln Leu Ala Ile Ile Gly Asp Asp Ile Asn Arg Arg
1               5                   10

<210> SEQ ID NO 53
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Ala Ala Arg Leu Lys Ala Leu Gly Asp Glu Leu His Gln Arg
1               5                   10

<210> SEQ ID NO 54
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Ser Glu Cys Leu Arg Arg Ile Gly Asp Glu Leu Asp Ser Asn
1               5                   10

<210> SEQ ID NO 55
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ala Gln Glu Leu Arg Arg Ile Gly Asp Glu Phe Asn Ala Tyr
1               5                   10

<210> SEQ ID NO 56
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Thr Val Leu Leu Arg Leu Gly Asp Glu Leu Glu Gln Ile
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Gln Ala Leu Arg Glu Ala Gly Asp Glu Phe Glu Leu Arg
```

-continued

<210> SEQ ID NO 58
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 58

His Leu Thr Leu Arg Gln Ala Gly Asp Asp Phe Ser Arg Arg
1               5                   10

<210> SEQ ID NO 59
<211> LENGTH: 14
<212> TYPE: PRT
<213> ORGANISM: Artificial Sequence
<220> FEATURE:
<223> OTHER INFORMATION: Description of Artificial Sequence: Synthetic peptide

<400> SEQUENCE: 59

Leu Glu Thr Leu Arg Arg Val Gly Asp Gly Val Gln Arg Asn
1               5                   10

<210> SEQ ID NO 60
<211> LENGTH: 184
<212> TYPE: PRT
<213> ORGANISM: Mus musculus

<400> SEQUENCE: 60

Met Glu Pro Ser Gln Cys Val Glu Glu Leu Glu Asp Asp Val Phe Gln
1               5                   10                  15

Pro Glu Asp Gly Glu Pro Val Thr Gln Pro Gly Ser Leu Leu Ser Ala
                20                  25                  30

Asp Leu Phe Ala Gln Ser Leu Leu Asp Cys Pro Leu Ser Arg Leu Gln
            35                  40                  45

Leu Phe Pro Leu Thr His Cys Cys Gly Pro Gly Leu Arg Pro Thr Ser
        50                  55                  60

Gln Glu Asp Lys Ala Thr Gln Thr Leu Ser Pro Ala Ser Pro Ser Pro
65                  70                  75                  80

Gly Val Met Leu Pro Cys Gly Val Thr Glu Glu Pro Gln Arg Leu Phe
                85                  90                  95

Tyr Gly Asn Ala Gly Tyr Arg Leu Pro Leu Pro Ala Ser Phe Pro Ala
            100                 105                 110

Val Leu Pro Ile Gly Glu Gln Pro Pro Glu Gly Gln Tyr Gln His Gln
        115                 120                 125

Ala Glu Val Gln Ile Ala Arg Lys Leu Gln Cys Ile Ala Asp Gln Phe
    130                 135                 140

His Arg Leu His Val Gln His Gln Gln Asn Gln Asn Pro Val Trp
145                 150                 155                 160

Asn Gln Ile Leu Leu Phe Leu His Asn Leu Ala Leu Asn Gly Glu Glu
                165                 170                 175

Asn Pro Asn Gly Ala Gly Pro Arg
            180

<210> SEQ ID NO 61
<211> LENGTH: 185
<212> TYPE: PRT
<213> ORGANISM: Homo sapiens

```
<400> SEQUENCE: 61

Met Glu Pro Pro Gln Cys Val Glu Glu Leu Glu Asp Asp Val Phe Gln
1               5                   10                  15

Ser Glu Asp Gly Glu Pro Gly Thr Gln Pro Gly Gly Leu Leu Ser Ala
            20                  25                  30

Asp Leu Phe Ala Gln Ser Gln Leu Asp Cys Pro Leu Ser Arg Leu Gln
        35                  40                  45

Leu Phe Pro Leu Thr His Cys Cys Gly Pro Gly Leu Arg Pro Ile Ser
    50                  55                  60

Gln Glu Asp Lys Ala Thr Gln Thr Leu Ser Pro Ala Ser Pro Ser Gln
65                  70                  75                  80

Gly Val Met Leu Pro Cys Gly Val Thr Glu Glu Pro Gln Arg Leu Phe
                85                  90                  95

Tyr Gly Asn Ala Gly Tyr Arg Leu Pro Leu Pro Ala Ser Phe Pro Ala
            100                 105                 110

Gly Ser Pro Leu Gly Glu Gln Pro Pro Glu Gly Gln Phe Leu Gln His
        115                 120                 125

Arg Ala Glu Val Gln Ile Ala Pro Lys Leu Gln Cys Ile Ala Asp Gln
    130                 135                 140

Phe His Arg Leu His Thr Gln His Gln Asn Arg Asp Arg Ala
145                 150                 155                 160

Trp Asn Gln Val Phe Leu Phe Leu Gln Asn Leu Ala Leu Asn Arg Gln
                165                 170                 175

Glu Asn Pro Glu Gly Val Gly Pro Trp
            180                 185

<210> SEQ ID NO 62
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Ile Ala Arg Lys Leu Gln Cys Ile Ala Asp Gln Phe His Arg Leu
1               5                   10                  15

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Ile Ala Gln Glu Leu Arg Arg Ile Gly Asp Phe Asn Ala Tyr
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ile Gly Ser Lys Leu Ala Ala Cys Asp Phe Asp Ala Gln
1               5                   10
```

<210> SEQ ID NO 65
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Arg Gln Leu Ala Ile Ile Gly Asp Asn Arg Arg
1               5                   10

<210> SEQ ID NO 66
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ser Glu Cys Leu Lys Arg Ile Gly Asp Asp Ser Asn
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Ala Leu Leu Ala Cys Ile Gly Asp Asp Val Ser
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Thr Ala Ala Leu Lys Ala Gly Asp His Gln Arg
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Arg Glu Leu Arg Arg Ser Asp Phe Val Asp Ser
1               5                   10

<210> SEQ ID NO 70
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Ser Ser Ala Ala Glu Glu Leu Ala Ala Ala Leu Arg Arg Ile Gly Asp
1               5                   10                  15

Glu Leu Asp Arg Arg Tyr
            20

<210> SEQ ID NO 71
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Glu Gly Pro Ala Asp Pro Leu His Gln Ala Met Arg Ala Ala Gly Asp
1               5                   10                  15

Glu Phe Glu Thr Arg Phe
            20

<210> SEQ ID NO 72
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Leu Gln Pro Ser Ser Thr Met Gly Gln Val Gly Arg Gln Leu Ala Ile
1               5                   10                  15

Ile Gly Asp Asp Ile Asn Arg Arg
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Gln Asp Ala Ser Thr Lys Lys Leu Ser Glu Cys Leu Lys Arg Ile Gly
1               5                   10                  15

Asp Glu Leu Asp Ser Asn
            20

<210> SEQ ID NO 74
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Ala Leu Ser Pro Pro Val Val His Leu Ala Leu Ala Leu Arg Gln Ala
1               5                   10                  15

Gly Asp Asp Phe Ser Arg Arg Tyr
            20

<210> SEQ ID NO 75
<211> LENGTH: 25
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 75

Asn Leu Trp Ala Ala Gln Arg Tyr Gly Arg Glu Leu Arg Arg Met Ser
1               5                   10                  15

Asp Glu Phe Val Asp Ser Phe Lys Lys
            20                  25

<210> SEQ ID NO 76
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Glu Asp Ile Ile Arg Asn Ile Ala Arg His Leu Ala Gln Val Gly Asp
1               5                   10                  15

Ser Met Asp Arg Ser Ile
            20

<210> SEQ ID NO 77
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Glu Val Ile Pro Met Ala Ala Val Lys Gln Ala Leu Arg Glu Ala Gly
1               5                   10                  15

Asp Glu Phe Glu Leu Arg Tyr
            20

<210> SEQ ID NO 78
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Glu Gly Ser Asp Ala Leu Arg Leu Ala Cys Ile Gly Asp Glu Met
1               5                   10                  15

Asp Val Ser Leu
            20

<210> SEQ ID NO 79
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Met Arg Pro Glu Ile Trp Ile Ala Gln Glu Leu Arg Arg Ile Gly Asp
1               5                   10                  15

Glu Phe Asn Ala Tyr Tyr
            20
```

<210> SEQ ID NO 80
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Ser Ser Ala Ala Gln Leu Thr Ala Ala Arg Leu Lys Ala Leu Gly Asp
1               5                   10                  15

Glu Leu His Gln Arg Thr
            20

<210> SEQ ID NO 81
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

His Gln Ala Glu Val Gln Ile Ala Arg Lys Leu Gln Cys Ile Ala Asp
1               5                   10                  15

Gln Phe His Arg Leu His
            20

<210> SEQ ID NO 82
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Ile Glu Arg Arg Lys Glu Val Glu Ser Ile Leu Lys Lys Asn Ser Asp
1               5                   10                  15

Trp Ile Trp Asp Trp Ser
            20

<210> SEQ ID NO 83
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Gly Arg Leu Ala Glu Val Cys Ala Val Leu Leu Arg Leu Gly Asp Glu
1               5                   10                  15

Leu Glu Met Ile Arg Pro
            20

<210> SEQ ID NO 84
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Leu Ala Glu Val Cys Thr Val Leu Leu Arg Leu Gly Asp Glu Leu Glu

Gln Ile Arg

<210> SEQ ID NO 85
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Met Thr Val Gly Glu Leu Ser Arg Ala Leu Gly His Glu Asn Gly Ser
1               5                   10                  15

Leu Asp Pro

<210> SEQ ID NO 86
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Ala Thr Ser Arg Lys Leu Glu Thr Leu Arg Arg Val Gly Asp Gly Val
1               5                   10                  15

Gln Arg Asn His Glu Thr Ala
            20

<210> SEQ ID NO 87
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Ser Ser Ala Ala Gln Leu Thr Ala Ala Arg Leu Lys Ala Leu Gly Asp
1               5                   10                  15

Glu Leu His Gln Arg Thr
            20

<210> SEQ ID NO 88
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Glu Gln Trp Ala Arg Glu Ile Gly Ala Gln Leu Arg Arg Met Ala Asp
1               5                   10                  15

Asp Leu Asn Ala Gln Tyr
            20

<210> SEQ ID NO 89
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide -continued

```
<400> SEQUENCE: 89

Ala Glu Leu Pro Pro Glu Phe Ala Ala Gln Leu Arg Lys Ile Gly Asp
1               5                   10                  15

Lys Val Tyr Cys Thr Trp
            20

<210> SEQ ID NO 90
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Pro Ala Asp Leu Lys Asp Glu Cys Ala Gln Leu Arg Arg Ile Gly Asp
1               5                   10                  15

Lys Val Asn Leu Arg Gln
            20

<210> SEQ ID NO 91
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Val Val Glu Gly Glu Lys Glu Val Glu Ala Leu Lys Lys Ser Ala Asp
1               5                   10                  15

Trp Val Ser Asp Trp Ser
            20

<210> SEQ ID NO 92
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (18)..(18)
<223> OTHER INFORMATION: Nle

<400> SEQUENCE: 92

Glu Asp Ile Ile Arg Asn Ile Ala Arg His Leu Ala Xaa Val Gly Asp
1               5                   10                  15

Xaa Xaa Asp Arg Ser Ile Trp
            20

<210> SEQ ID NO 93
<211> LENGTH: 21
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 93

Asp Ile Ile Arg Asn Ile Ala Arg His Leu Ala Xaa Val Gly Asp Xaa
1               5                   10                  15

Xaa Asp Arg Ser Ile
            20

<210> SEQ ID NO 94
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (18)..(18)
<223> OTHER INFORMATION: Nle

<400> SEQUENCE: 94

Glu Asp Ile Ile Arg Asn Ile Ala Arg His Leu Ala Xaa Val Glu Asp
1               5                   10                  15

Xaa Xaa Asp Arg Ser Ile Trp
            20

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
```

```
      position 12
<220> FEATURE:
<221> NAME/KEY: MOD_RES
<222> LOCATION: (17)..(17)
<223> OTHER INFORMATION: Nle

<400> SEQUENCE: 95

Asp Ile Ile Arg Asn Ile Ala Arg His Leu Ala Xaa Val Glu Asp Xaa
1               5                   10                  15

Xaa Asp Arg Ser Ile
            20

<210> SEQ ID NO 96
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 96

Asp Ile Ile Arg Asn Ile Ala Arg His Leu Ala Xaa Val Ser Asp Xaa
1               5                   10                  15

Xaa Asp Arg Ser Ile Trp
            20

<210> SEQ ID NO 97
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: Have an N-terminal label which is biotin
      attached to a labeled residue
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 97

Asp Ile Ile Arg Asn Ile Ala Arg His Leu Ala Xaa Val Gly Asp Xaa
```

```
1               5                  10                 15

Xaa Asp Arg Ser Ile Trp
            20

<210> SEQ ID NO 98
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: Have an N-terminal label which is biotin
      attached to a labeled residue
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 98

Asp Ile Ile Arg Asn Ile Ala Arg His Leu Ala Xaa Val Glu Asp Xaa
1               5                  10                 15

Xaa Asp Arg Ser Ile Trp
            20

<210> SEQ ID NO 99
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 8
<220> FEATURE:
<221> NAME/KEY: MOD_RES
<222> LOCATION: (18)..(18)
<223> OTHER INFORMATION: Nle

<400> SEQUENCE: 99

Glu Asp Ile Ile Arg Asn Ile Xaa Arg His Leu Xaa Gln Val Gly Asp
1               5                  10                 15

Ser Xaa Asp Arg Ser Ile Trp
            20

<210> SEQ ID NO 100
<211> LENGTH: 21
<212> TYPE: PRT
```

-continued

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: A modified amino acid in which the side chain
      has been replaced by a crosslink to the modified amino acid at
      position 11
<220> FEATURE:
<221> NAME/KEY: MOD_RES
<222> LOCATION: (11)..(11)
<223> OTHER INFORMATION: A modified amino acid in which the side chain
      has been replaced by a crosslink to the modified amino acid at
      position 7
<220> FEATURE:
<221> NAME/KEY: MOD_RES
<222> LOCATION: (17)..(17)
<223> OTHER INFORMATION: Nle

<400> SEQUENCE: 100

Asp Ile Ile Arg Asn Ile Xaa Arg His Leu Xaa Gln Val Gly Asp Ser
1               5                   10                  15

Xaa Asp Arg Ser Ile
            20

<210> SEQ ID NO 101
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: A modified amino acid in which the side chain
      has been replaced by a crosslink to the modified amino acid at
      position 8
<220> FEATURE:
<221> NAME/KEY: MOD_RES
<222> LOCATION: (8)..(8)
<223> OTHER INFORMATION: A modified amino acid in which the side chain
      has been replaced by a crosslink to the modified amino acid at
      position 4
<220> FEATURE:
<221> NAME/KEY: MOD_RES
<222> LOCATION: (14)..(14)
<223> OTHER INFORMATION: Nle

<400> SEQUENCE: 101

Arg Asn Ile Xaa Arg His Leu Xaa Gln Val Gly Asp Ser Xaa Asp Arg
1               5                   10                  15

Trp

<210> SEQ ID NO 102
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
```

```
            position 8
<220> FEATURE:
<221> NAME/KEY: MOD_RES
<222> LOCATION: (18)..(18)
<223> OTHER INFORMATION: Nle

<400> SEQUENCE: 102

Glu Asp Ile Ile Arg Asn Ile Xaa Arg His Leu Xaa Gln Val Glu Asp
1               5                   10                  15

Ser Xaa Asp Arg Ser Ile Trp
            20

<210> SEQ ID NO 103
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: Have an N-terminal label which is biotin
      attached to a labeled residue
<220> FEATURE:
<221> NAME/KEY: MOD_RES
<222> LOCATION: (7)..(7)
<223> OTHER INFORMATION: A modified amino acid in which the side chain
      has been replaced by a crosslink to the modified amino acid at
      position 11
<220> FEATURE:
<221> NAME/KEY: MOD_RES
<222> LOCATION: (11)..(11)
<223> OTHER INFORMATION: A modified amino acid in which the side chain
      has been replaced by a crosslink to the modified amino acid at
      position 7
<220> FEATURE:
<221> NAME/KEY: MOD_RES
<222> LOCATION: (17)..(17)
<223> OTHER INFORMATION: Nle

<400> SEQUENCE: 103

Asp Ile Ile Arg Asn Ile Xaa Arg His Leu Xaa Gln Val Gly Asp Ser
1               5                   10                  15

Xaa Asp Arg Ser Ile Trp
            20

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: BINDING
<222> LOCATION: (1)..(1)
<223> OTHER INFORMATION: Have an N-terminal label which is biotin
      attached to a labeled residue
<220> FEATURE:
<221> NAME/KEY: MOD_RES
<222> LOCATION: (7)..(7)
<223> OTHER INFORMATION: A modified amino acid in which the side chain
      has been replaced by a crosslink to the modified amino acid at
      position 11
<220> FEATURE:
<221> NAME/KEY: MOD_RES
<222> LOCATION: (11)..(11)
<223> OTHER INFORMATION: A modified amino acid in which the side chain
      has been replaced by a crosslink to the modified amino acid at
      position 7
<220> FEATURE:
<221> NAME/KEY: MOD_RES
<222> LOCATION: (17)..(17)
```

```
<223> OTHER INFORMATION: Nle

<400> SEQUENCE: 104

Asp Ile Ile Arg Asn Ile Xaa Arg His Leu Xaa Gln Val Glu Asp Ser
1               5                   10                  15

Xaa Asp Arg Ser Ile
            20

<210> SEQ ID NO 105
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 9
<220> FEATURE:
<221> NAME/KEY: MOD_RES
<222> LOCATION: (18)..(18)
<223> OTHER INFORMATION: Nle

<400> SEQUENCE: 105

Glu Asp Ile Ile Arg Asn Ile Ala Xaa His Leu Ala Xaa Val Gly Asp
1               5                   10                  15

Ser Xaa Asp Arg Ser Ile Trp
            20

<210> SEQ ID NO 106
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 10
<220> FEATURE:
<221> NAME/KEY: MOD_RES
<222> LOCATION: (18)..(18)
<223> OTHER INFORMATION: Nle

<400> SEQUENCE: 106

Glu Asp Ile Ile Arg Asn Ile Ala Arg Xaa Leu Ala Gln Val Gly Asp
1               5                   10                  15

Xaa Xaa Asp Arg Ser Ile Trp
            20

<210> SEQ ID NO 107
<211> LENGTH: 23
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: A modified amino acid in which the side chain
      has been replaced by a crosslink to the modified amino acid at
      position 9
<220> FEATURE:
<221> NAME/KEY: MOD_RES
<222> LOCATION: (9)..(9)
<223> OTHER INFORMATION: A modified amino acid in which the side chain
      has been replaced by a crosslink to the modified amino acid at
      position 5
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (18)..(18)
<223> OTHER INFORMATION: Nle

<400> SEQUENCE: 107

Glu Asp Ile Ile Xaa Asn Ile Ala Xaa His Leu Ala Xaa Val Gly Asp
1               5                   10                  15

Xaa Xaa Asp Arg Ser Ile Trp
            20

<210> SEQ ID NO 108
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: A modified amino acid in which the side chain
      has been replaced by a crosslink to the modified amino acid at
      position 18
<220> FEATURE:
<221> NAME/KEY: MOD_RES
<222> LOCATION: (15)..(15)
<223> OTHER INFORMATION: Nle
<220> FEATURE:
<221> NAME/KEY: MOD_RES
<222> LOCATION: (18)..(18)
<223> OTHER INFORMATION: A modified amino acid in which the side chain
      has been replaced by a crosslink to the modified amino acid at
      position 14

<400> SEQUENCE: 108

Asn Leu Trp Ala Ala Gln Arg Tyr Gly Arg Glu Leu Arg Xaa Xaa Ser
1               5                   10                  15

Asp Xaa Phe Val Asp Ser Phe Lys Lys
            20                  25

<210> SEQ ID NO 109
<211> LENGTH: 21
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 109

Asp Ile Ile Arg Asn Ile Ala Arg His Ala Ala Xaa Val Gly Ala Xaa
1               5                   10                  15

Xaa Asp Arg Ser Ile
            20

<210> SEQ ID NO 110
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)..(12)
<223> OTHER INFORMATION: A modified amino acid in which the side chain
      has been replaced by a crosslink to the modified amino acid at
      position 16
<220> FEATURE:
<221> NAME/KEY: MOD_RES
<222> LOCATION: (16)..(16)
<223> OTHER INFORMATION: A modified amino acid in which the side chain
      has been replaced by a crosslink to the modified amino acid at
      position 12
<220> FEATURE:
<221> NAME/KEY: MOD_RES
<222> LOCATION: (17)..(17)
<223> OTHER INFORMATION: Nle

<400> SEQUENCE: 110

Asp Ile Ile Arg Asn Ile Ala Arg His Ala Ala Xaa Val Glu Ala Xaa
1               5                   10                  15

Xaa Asp Arg Ser Ile
            20

<210> SEQ ID NO 111
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 9
```

-continued

<400> SEQUENCE: 111

Ile Trp Ile Ala Gln Glu Leu Arg Xaa Ile Gly Asp Xaa Phe Asn Ala
1               5                   10                  15

Tyr Tyr Ala Arg Arg
            20

<210> SEQ ID NO 112
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (18)..(18)
<223> OTHER INFORMATION: Nle

<400> SEQUENCE: 112

Glu Asp Ile Ile Arg Asn Ile Ala Arg His Leu Ala Gln Val Gly Asp
1               5                   10                  15

Ser Xaa Asp Arg Ser Ile Trp
            20

<210> SEQ ID NO 113
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: S enantiomers of the 5-carbon olefinic amino
      acid
<220> FEATURE:
<221> NAME/KEY: MOD_RES
<222> LOCATION: (17)..(17)
<223> OTHER INFORMATION: S enantiomers of the 5-carbon olefinic amino
      acid
<220> FEATURE:
<221> NAME/KEY: MOD_RES
<222> LOCATION: (18)..(18)
<223> OTHER INFORMATION: Nle

<400> SEQUENCE: 113

Glu Asp Ile Ile Arg Asn Ile Ala Arg His Leu Ala Xaa Val Gly Asp
1               5                   10                  15

Xaa Xaa Asp Arg Ser Ile Trp
            20

<210> SEQ ID NO 114
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (13)..(13)
<223> OTHER INFORMATION: S enantiomers of the 5-carbon olefinic amino
      acid
<220> FEATURE:
<221> NAME/KEY: MOD_RES
<222> LOCATION: (17)..(17)
<223> OTHER INFORMATION: S enantiomers of the 5-carbon olefinic amino
      acid
<220> FEATURE:

```
<221> NAME/KEY: MOD_RES
<222> LOCATION: (18)..(18)
<223> OTHER INFORMATION: Nle

<400> SEQUENCE: 114

Glu Asp Ile Ile Arg Asn Ile Ala Arg His Leu Ala Xaa Val Glu Asp
1               5                   10                  15

Xaa Xaa Asp Arg Ser Ile Trp
            20

<210> SEQ ID NO 115
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: S enantiomers of the 5-carbon olefinic amino
      acid
<220> FEATURE:
<221> NAME/KEY: MOD_RES
<222> LOCATION: (12)..(12)
<223> OTHER INFORMATION: S enantiomers of the 5-carbon olefinic amino
      acid
<220> FEATURE:
<221> NAME/KEY: MOD_RES
<222> LOCATION: (18)..(18)
<223> OTHER INFORMATION: Nle

<400> SEQUENCE: 115

Glu Asp Ile Ile Arg Asn Ile Xaa Arg His Leu Xaa Gln Val Gly Asp
1               5                   10                  15

Ser Xaa Asp Arg Ser Ile Trp
            20

<210> SEQ ID NO 116
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)..(9)
<223> OTHER INFORMATION: S enantiomers of the 5-carbon olefinic amino
      acid
<220> FEATURE:
<221> NAME/KEY: MOD_RES
<222> LOCATION: (13)..(13)
<223> OTHER INFORMATION: S enantiomers of the 5-carbon olefinic amino
      acid
<220> FEATURE:
<221> NAME/KEY: MOD_RES
<222> LOCATION: (18)..(18)
<223> OTHER INFORMATION: Nle

<400> SEQUENCE: 116

Glu Asp Ile Ile Arg Asn Ile Ala Xaa His Leu Ala Xaa Val Gly Asp
1               5                   10                  15

Ser Xaa Asp Arg Ser Ile Trp
            20

<210> SEQ ID NO 117
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<221> NAME/KEY: MOD_RES
<222> LOCATION: (10)..(10)
<223> OTHER INFORMATION: R enantiomers of the 5-carbon olefinic amino
      acid
<220> FEATURE:
<221> NAME/KEY: MOD_RES
<222> LOCATION: (17)..(17)
<223> OTHER INFORMATION: S enantiomers of the 5-carbon olefinic amino
      acid
<220> FEATURE:
<221> NAME/KEY: MOD_RES
<222> LOCATION: (18)..(18)
<223> OTHER INFORMATION: Nle

<400> SEQUENCE: 117

Glu Asp Ile Ile Arg Asn Ile Ala Arg Xaa Leu Ala Gln Val Gly Asp
1               5                   10                  15

Xaa Xaa Asp Arg Ser Ile Trp
            20

<210> SEQ ID NO 118
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (14)..(14)
<223> OTHER INFORMATION: A modified amino acid in which the side chain
      has been replaced by a crosslink to the modified amino acid at
      position 18
<220> FEATURE:
<221> NAME/KEY: MOD_RES
<222> LOCATION: (18)..(18)
<223> OTHER INFORMATION: A modified amino acid in which the side chain
      has been replaced by a crosslink to the modified amino acid at
      position 14
<220> FEATURE:
<221> NAME/KEY: MOD_RES
<222> LOCATION: (19)..(19)
<223> OTHER INFORMATION: Nle

<400> SEQUENCE: 118

Xaa Glu Asp Ile Ile Arg Asn Ile Ala Arg His Leu Ala Xaa Val Glu
1               5                   10                  15

Asp Xaa Xaa Asp Arg Ser Ile Trp
            20

<210> SEQ ID NO 119
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (14)..(14)
<223> OTHER INFORMATION: A modified amino acid in which the side chain
      has been replaced by a crosslink to the modified amino acid at
      position 18
```

```
<220> FEATURE:
<221> NAME/KEY: MOD_RES
<222> LOCATION: (18)..(18)
<223> OTHER INFORMATION: A modified amino acid in which the side chain
      has been replaced by a crosslink to the modified amino acid at
      position 14
<220> FEATURE:
<221> NAME/KEY: MOD_RES
<222> LOCATION: (19)..(19)
<223> OTHER INFORMATION: Nle

<400> SEQUENCE: 119

Xaa Glu Asp Ile Ile Arg Asn Ile Ala Arg His Leu Ala Xaa Val Glu
1               5                   10                  15

Asp Xaa Xaa Asp Arg Ser Ile Trp
            20

<210> SEQ ID NO 120
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 13
<220> FEATURE:
<221> NAME/KEY: MOD_RES
<222> LOCATION: (18)..(18)
<223> OTHER INFORMATION: Nle

<400> SEQUENCE: 120

Xaa Asp Ile Ile Arg Asn Ile Ala Arg His Leu Ala Xaa Val Gly Asp
1               5                   10                  15

Xaa Xaa Asp Arg Ser Ile
            20

<210> SEQ ID NO 121
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (13)..(13)
<223> OTHER INFORMATION: A modified amino acid in which the side chain
      has been replaced by a crosslink to the modified amino acid at
      position 17
<220> FEATURE:
<221> NAME/KEY: MOD_RES
<222> LOCATION: (17)..(17)
<223> OTHER INFORMATION: A modified amino acid in which the side chain
      has been replaced by a crosslink to the modified amino acid at
      position 13
```

```
<220> FEATURE:
<221> NAME/KEY: MOD_RES
<222> LOCATION: (18)..(18)
<223> OTHER INFORMATION: Nle

<400> SEQUENCE: 121

Xaa Asp Ile Ile Arg Asn Ile Ala Arg His Leu Ala Xaa Val Glu Asp
1               5                   10                  15

Xaa Xaa Asp Arg Ser Ile
            20

<210> SEQ ID NO 122
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (10)..(10)
<223> OTHER INFORMATION: A modified amino acid in which the side chain
      has been replaced by a crosslink to the modified amino acid at
      position 14
<220> FEATURE:
<221> NAME/KEY: MOD_RES
<222> LOCATION: (14)..(14)
<223> OTHER INFORMATION: A modified amino acid in which the side chain
      has been replaced by a crosslink to the modified amino acid at
      position 10

<400> SEQUENCE: 122

Xaa Ile Trp Ile Ala Gln Glu Leu Arg Xaa Ile Gly Asp Xaa Phe Asn
1               5                   10                  15

Ala Tyr Tyr Ala Arg Arg
            20

<210> SEQ ID NO 123
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Beta-Ala
<220> FEATURE:
<221> NAME/KEY: MOD_RES
<222> LOCATION: (15)..(15)
<223> OTHER INFORMATION: A modified amino acid in which the side chain
      has been replaced by a crosslink to the modified amino acid at
      position 19
<220> FEATURE:
<221> NAME/KEY: MOD_RES
<222> LOCATION: (16)..(16)
<223> OTHER INFORMATION: Nle
<220> FEATURE:
<221> NAME/KEY: MOD_RES
<222> LOCATION: (19)..(19)
<223> OTHER INFORMATION: A modified amino acid in which the side chain
      has been replaced by a crosslink to the modified amino acid at
      position 15

<400> SEQUENCE: 123

Xaa Asn Leu Trp Ala Ala Gln Arg Tyr Gly Arg Glu Leu Arg Xaa Xaa
1               5                   10                  15
```

```
Ser Asp Xaa Phe Val Asp Ser Phe Lys Lys
         20                  25
```